United States Patent
Wu et al.

(10) Patent No.: US 11,898,186 B1
(45) Date of Patent: Feb. 13, 2024

(54) COMPOSITIONS AND METHODS FOR PREPARING CAPPED MRNA

(71) Applicant: GENSCRIPT USA INC., Redmond, WA (US)

(72) Inventors: Cheng-Hsien Wu, Redmond, WA (US); Fengmei Pi, Redmond, WA (US); Robert Dempcy, Redmond, WA (US); Shambhavi Shubham, Redmond, WA (US); Kristine Bielecki, Redmond, WA (US); Aaron Ball, Redmond, WA (US)

(73) Assignee: GENSCRIPT USA INC., Redmond, VA (US)

( * ) Notice: Subject to any disclaimer, the term of this patent is extended or adjusted under 35 U.S.C. 154(b) by 0 days.

(21) Appl. No.: 18/069,123

(22) Filed: Dec. 20, 2022

Related U.S. Application Data

(60) Provisional application No. 63/371,132, filed on Aug. 11, 2022, provisional application No. 63/396,904, filed on Aug. 10, 2022.

(51) Int. Cl.
*A61K 31/7115* (2006.01)
*A61K 48/00* (2006.01)
(Continued)

(52) U.S. Cl.
CPC ............ *C12P 19/34* (2013.01); *C12N 9/1276* (2013.01); *C12N 9/16* (2013.01); *C12N 9/6472* (2013.01);
(Continued)

(58) Field of Classification Search
CPC .............................. C12P 19/34; C12N 9/1276; C12Y 207/07049
See application file for complete search history.

(56) References Cited

U.S. PATENT DOCUMENTS 10,465,190 B1  11/2019  Chen et al.
10,494,399 B2  12/2019  Hogrefe et al.
(Continued)

FOREIGN PATENT DOCUMENTS

EP       4149485 A1    3/2023
JP    2008500039 A    1/2008
(Continued)

OTHER PUBLICATIONS

Brunelle et al. (Methods in Enzymology, 2013, vol. 530: pp. 101-114).*
(Continued)

*Primary Examiner* — Terra C Gibbs
(74) *Attorney, Agent, or Firm* — McBee, Moore & Vanik IP, LLC

(57) ABSTRACT

A method for in vitro transcription of a DNA template into RNA includes providing a mixture containing a buffer substance, ribonucleoside triphosphates (NTPs), one or more magnesium salts in a concentration of from about 2 mM to about 60 mM, the DNA template, and a recombinant RNA polymerase, and incubating the reaction mixture at from about 25° C. to about 40° C. for from about 1 hour to about 12 hours thereby producing the RNA. A method for in vitro transcription includes providing a DNA template and a cap analogue that binds to −1 and/or +1 nucleotides of promoter for in vitro transcription, thus producing more full length mRNAs, allowing for more flexibility on the choice of first mRNA base, and providing +2 position open for custom sequence.

29 Claims, 27 Drawing Sheets

Specification includes a Sequence Listing.

(51) Int. Cl.
  C12P 19/34 (2006.01)
  C12N 9/12 (2006.01)
  C12N 9/16 (2006.01)
  C12N 9/64 (2006.01)
(52) U.S. Cl.
  CPC ............... *C12Y 207/07049* (2013.01); *C12Y 301/03002* (2013.01); *C12Y 304/22056* (2013.01)

(56) References Cited

U.S. PATENT DOCUMENTS

| | | | |
|---|---|---|---|
| 10,519,189 | B2 | 12/2019 | Hogrefe et al. |
| 10,913,768 | B2 | 2/2021 | Hogrefe et al. |
| 11,248,223 | B2 | 2/2022 | Yazdan et al. |
| 2008/0171361 | A1* | 7/2008 | Scheets ............ C12P 21/02 536/23.1 |
| 2018/0208957 | A1 | 7/2018 | Tilmann et al. |
| 2019/0049414 | A1 | 2/2019 | Aniela et al. |
| 2020/0066375 | A1 | 2/2020 | Lu et al. |
| 2022/0362372 | A1 | 11/2022 | Dormitzer et al. |
| 2023/0181481 | A1 | 6/2023 | White et al. |
| 2023/0183769 | A1 | 6/2023 | Rabe et al. |

FOREIGN PATENT DOCUMENTS

| | | | | |
|---|---|---|---|---|
| WO | 2005116250 | A2 | 12/2005 | |
| WO | 2019241684 | A1 | 12/2019 | |
| WO | WO-2020263985 | A1 * | 12/2020 | ......... A61K 31/7105 |
| WO | 2021058145 | A1 | 4/2021 | |
| WO | WO-2021156267 | A1 * | 8/2021 | ............ A61K 39/12 |
| WO | 2021231963 | A1 | 11/2021 | |
| WO | 2022162027 | A2 | 8/2022 | |
| WO | 2022173199 | A1 | 8/2022 | |
| WO | 2022234417 | A1 | 11/2022 | |
| WO | 2022256597 | A1 | 12/2022 | |
| WO | 2023019181 | A1 | 2/2023 | |
| WO | 2023057930 | A1 | 4/2023 | |

OTHER PUBLICATIONS

Warminski et al. (Bioconjugate Chem., 2017 vol. 28:1978-1992).*
Ishikawa, Masahido, Preparation of eukaryotic mRNA having differently methylated adenosine at the 5'terminus and the effect of the methl group in translation, 2009 Oxford University Press Symposium date: Sep. 27, 2009, Nucleic Acids Symposium Series No. 53, p. 129-130.
Bowater, Richard P., Transcription increases the deletion frequency of long CTG•CAG triplet repeats from plasmids in *Escherichia coli*, Nucleic Acids Research, vol. 25, Issue 14, Jul. 1, 1997, pp. 2861-2868.
Galloway, Allison, mRNA cap regulation in mammalian cell function and fate, Biochimica et Biophysica Acta (BBA)—Gene Regulatory Mechanismsvol. 1862, Issue 3, Mar. 2019, pp. 270-279.
D. Stueber, H. Bujard, Transcription from efficient promoters can interfere with plasmid replication and diminish expression of plasmid specified genes. The EMBO Journal (1982)1:vol. 1, Issue 111, pp. 1399-1404, Nov. 1982.
Werner, Maria, 2'-O-ribose methylation of cap2 in human: function and evolution in a horizontally mobile family, Nucleic Acids Research, vol. 39, Issue 11, Jun. 1, 2011, pp. 4756-4768, Published: Feb. 9, 2011.
Sachs, Alan, Poly(A) tail metabolism and function in eucaryotes, The Journal of biological chemistry (Print). vol 268, No. 31, pp. 22955-22958. 1993.
Perry, R.P., RNA Processing Comes of Age, J Cell Biol.Journal List J Cell Biol v.91(3); pp. 28-38; Dec. 1, 1981.
Banerjee, AK, 5'-Terminal Cap Structure in Eucaryotic Messenger, Ribonucleic Acids, Microbiology Reviews, vol. 44, No. 2, p. 175-205, Jun. 1980.
Sikorski, Pawel J., The identity and methylation status of the first transcribed nucleotide in eukaryotic mRNA 5' cap modulates protein expression in living cells. Nucleic Acids Research, vol. 48, Issue 4, Feb. 28, 2020, pp. 1607-1626, Published: Jan. 27, 2020.
Cao, GJ. Identification of the gene for an *Escherichia coli* poly(A) polymerase. G J Cao and N SarkarAuthors Info & Affiliations . Proc. National Academy of Science USA vol. 89, pp. 10380-10384. Nov. 1, 1992.
Cao, Jicong. High-throughput 5' UTR engineering for enhanced protein production in non-viral gene therapies. Nature Communications vol. 12, Article No. 4138 (2021). Published: Jul. 6, 2021.
Iskakova, Madina B., et al. "Troubleshooting coupled in vitro transcription-translation system derived from *Escherichia coli* cells: synthesis of high-yield fully active proteins", Nucleic Acids Research, vol. 34, No. 19, e135, Oct. 2006.

* cited by examiner

```
                               SEQUENCE LISTING

Sequence total quantity: 22
SEQ ID NO: 1           moltype = DNA   length = 100
FEATURE                Location/Qualifiers
misc_feature           1..100
                       note = 5' UTR
source                 1..100
                       mol_type = other DNA
                       organism = synthetic construct
SEQUENCE: 1
cttgtctcgc tccggggaac gctcggaaac tcccggccgc cgccacccgc gtctgttctg   60
ttacacaagg gaagaaaagc cgctgccgca ctccgagtgt                        100

SEQ ID NO: 2           moltype = DNA   length = 114
FEATURE                Location/Qualifiers
misc_feature           1..114
                       note = 3' UTR
source                 1..114
                       mol_type = other DNA
                       organism = synthetic construct
SEQUENCE: 2
taagctggag cctcggtggc catgcttctt gcccttggg cctcccccca gcccctcctc    60
cccttcctgc acccgtaccc ccgtggtctt tgaataaagt ctgagtgggc ggca         114

SEQ ID NO: 3           moltype = DNA   length = 100
FEATURE                Location/Qualifiers
misc_feature           1..100
                       note = 5' UTR
source                 1..100
                       mol_type = other DNA
                       organism = synthetic construct
SEQUENCE: 3
cactcgcgct gccatcactc ttccgccgtc ttcgccgcca tcctcggcgc gactcgcttc   60
tttcggttct accaggtaga gtccgccgcc atcctccacc                        100

SEQ ID NO: 4           moltype = DNA   length = 106
FEATURE                Location/Qualifiers
misc_feature           1..106
                       note = 3' UTR
source                 1..106
                       mol_type = other DNA
                       organism = synthetic construct
SEQUENCE: 4
ttaattaagc tgccttctgc ggggcttgcc ttctggccat gcccttcttc tctcccttgc   60
acctgtacct cttggtcttt gaataaagcc tgagtaggaa gtctag                 106

SEQ ID NO: 5           moltype = DNA   length = 54
FEATURE                Location/Qualifiers
misc_feature           1..54
                       note = 5' UTR
source                 1..54
                       mol_type = other DNA
                       organism = synthetic construct
SEQUENCE: 5
gagaataaac tagtattctt ctggtcccca cagactcaga gagaacccgc cacc         54

SEQ ID NO: 6           moltype = DNA   length = 75
FEATURE                Location/Qualifiers
misc_feature           1..75
                       note = 3' UTR
source                 1..75
                       mol_type = other DNA
                       organism = synthetic construct
SEQUENCE: 6
atttctatta aaggttcctt tgttccctaa gtccaactac taaactgggg gatattatga   60
agggccttga gcatc                                                   75

SEQ ID NO: 7           moltype = DNA   length = 64
FEATURE                Location/Qualifiers
misc_feature           1..64
                       note = 5' UTR
source                 1..64
                       mol_type = other DNA
```

```
                              organism = synthetic construct
SEQUENCE: 7
atctgaatgg agcagccaag cttgacactc taaacccctg gacccttctt ttttgcccttt    60
ggct                                                                  64

SEQ ID NO: 8           moltype = DNA   length = 295
FEATURE                Location/Qualifiers
misc_feature           1..295
                       note = 3' UTR
source                 1..295
                       mol_type = other DNA
                       organism = synthetic construct
SEQUENCE: 8
ctcgagctgg tactgcatgc acgcaatgct agctgcccct ttcccgtcct gggtaccccg     60
agtctccccc gacctcgggt cccaggtatg ctcccacctc cacctgcccc actcaccacc   120
tctgctagtt ccagacacct cccaagcacg cagcaatgca gctcaaaacg cttagcctag   180
ccacaccccc acgggaaaca gcagtgatta acctttagca ataaacgaaa gtttaactaa   240
gctatactaa ccccagggtt ggtcaatttc gtgccagcca caccctggag ctagc        295

SEQ ID NO: 9           moltype = DNA   length = 38
FEATURE                Location/Qualifiers
misc_feature           1..38
                       note = 5' UTR
source                 1..38
                       mol_type = other DNA
                       organism = synthetic construct
SEQUENCE: 9
aaataagaga gaaagaagaa gtaagaagaa atataaga                             38

SEQ ID NO: 10          moltype = DNA   length = 20
FEATURE                Location/Qualifiers
misc_feature           1..20
                       note = promoter
source                 1..20
                       mol_type = other DNA
                       organism = synthetic construct
SEQUENCE: 10
taatacgact cactataggg                                                 20

SEQ ID NO: 11          moltype = DNA   length = 19
FEATURE                Location/Qualifiers
misc_feature           1..19
                       note = promoter
source                 1..19
                       mol_type = other DNA
                       organism = synthetic construct
SEQUENCE: 11
taatacgact cactatagg                                                  19

SEQ ID NO: 12          moltype = DNA   length = 20
FEATURE                Location/Qualifiers
misc_feature           1..20
                       note = promoter
source                 1..20
                       mol_type = other DNA
                       organism = synthetic construct
SEQUENCE: 12
taatacgact cactataagg                                                 20

SEQ ID NO: 13          moltype = DNA   length = 20
FEATURE                Location/Qualifiers
misc_feature           1..20
                       note = promoter
source                 1..20
                       mol_type = other DNA
                       organism = synthetic construct
SEQUENCE: 13
taatacgact cactatagat                                                 20

SEQ ID NO: 14          moltype = DNA   length = 19
FEATURE                Location/Qualifiers
misc_feature           1..19
                       note = promoter
source                 1..19
                       mol_type = other DNA
                       organism = synthetic construct
SEQUENCE: 14
taatacgact cactataga                                                  19
```

```
SEQ ID NO: 15              moltype = DNA  length = 20
FEATURE                    Location/Qualifiers
source                     1..20
                           mol_type = other DNA
                           organism = synthetic construct
SEQUENCE: 15
taatacgact cactattagg                                                       20

SEQ ID NO: 16              moltype = DNA  length = 20
FEATURE                    Location/Qualifiers
variation                  18
                           note = A or G
variation                  19
                           note = A or G
variation                  20
                           note = A or T or G or C
source                     1..20
                           mol_type = other DNA
                           organism = synthetic construct
SEQUENCE: 16
taatacgact cactatannn                                                       20

SEQ ID NO: 17              moltype = DNA  length = 31
FEATURE                    Location/Qualifiers
misc_feature               1..31
                           note = Poly A forward primer
source                     1..31
                           mol_type = other DNA
                           organism = synthetic construct
SEQUENCE: 17
gcttaggaaa ttaatacgac tcactataag g                                          31

SEQ ID NO: 18              moltype = DNA  length = 122
FEATURE                    Location/Qualifiers
misc_feature               1..122
                           note = Poly A reverse primer
source                     1..122
                           mol_type = other DNA
                           organism = synthetic construct
SEQUENCE: 18
tttttttttt tttttttttt tttttttttt tttttttttt tttttttttt tttttttttt           60
tttttttttt tttttttttt tttttttttt tttttttttt gccgcccact cagactttat          120
tc                                                                         122

SEQ ID NO: 19              moltype = DNA  length = 44
FEATURE                    Location/Qualifiers
modified_base              1..2
                           mod_base = OTHER
                           note = phosphorothioate backbone modification
modified_base              2..3
                           mod_base = OTHER
                           note = phosphorothioate backbone modification
modified_base              3..4
                           mod_base = OTHER
                           note = phosphorothioate backbone modification
modified_base              41..42
                           mod_base = OTHER
                           note = phosphorothioate backbone modification
modified_base              42..43
                           mod_base = OTHER
                           note = phosphorothioate backbone modification
modified_base              43..44
                           mod_base = OTHER
                           note = phosphorothioate backbone modification
source                     1..44
                           mol_type = other DNA
                           organism = synthetic construct
SEQUENCE: 19
cactgcttac tggcttatcg aaattaatac gactcactat agga                            44

SEQ ID NO: 20              moltype = DNA  length = 130
FEATURE                    Location/Qualifiers
primer_bind                1..130
                           note = Poly A reverse primer
modified_base              1..2
                           mod_base = OTHER
                           note = phosphorothioate background modification
modified_base              2..3
                           mod_base = OTHER
```

```
modified_base              note = phosphorothioate background modification
                           2
                           mod_base = um
modified_base              3..4
                           mod_base = OTHER
                           note = phosphorothioate backbone modification
modified_base              127..128
                           mod_base = OTHER
                           note = phosphorothioate backbone modification
modified_base              128..129
                           mod_base = OTHER
                           note = Phosphorothioate backbone modification
modified_base              129..130
                           mod_base = OTHER
                           note = phosphorothioate backbone modification
source                     1..130
                           mol_type = other DNA
                           organism = synthetic construct
SEQUENCE: 20
tnttttttt tttttttttt tttttttttt tttttttttt tttttttttt tttttttttt    60
tttttttttt tttttttttt tttttttttt tttttttttt gccgcccact cagactttat  120
tcaaagacca                                                          130

SEQ ID NO: 21              moltype = DNA  length = 23
FEATURE                    Location/Qualifiers
misc_feature               1..23
                           note = promoter
source                     1..23
                           mol_type = other DNA
                           organism = synthetic construct
SEQUENCE: 21
taatacgact cactataggg aga                                            23

SEQ ID NO: 22              moltype = DNA  length = 23
FEATURE                    Location/Qualifiers
misc_feature               1..23
                           note = promoter
source                     1..23
                           mol_type = other DNA
                           organism = synthetic construct
SEQUENCE: 22
tctccctata gtgagtcgta tta                                            23
```

COMPOSITIONS AND METHODS FOR PREPARING CAPPED MRNA

RELATED APPLICATIONS

This application claims priority to U.S. Provisional Application Nos. 63/371,132, filed 11 Aug. 2022, and 63/396,904, filed 10 Aug. 2022. Each of these applications is incorporated by reference in its entirety for all purposes.

REFERENCE TO SEQUENCE LISTING SUBMITTED AS A COMPLIANT ASCII TEXT

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_3000076-005002_ST26.xml" created on Mar. 22, 2023, and 36,911 bytes in size) is submitted concurrently with the instant application, and the entire contents of the Sequence Listing are incorporated herein by reference.

BACKGROUND

The present disclosure relates generally to methods and compositions for in vitro transcription.

mRNA is a well-defined molecule with structure of 5' Cap, 5' end untranslated region (UTR), open reading frame sequence coding for a gene(s) of interest, and 3' end UTR, and poly A tail. Preparation of capped mRNA through in vitro synthesis may have significant importance for both fundamental scientific research and new therapeutics development. Several factors go into generating an mRNA that may have high expression levels, stability, and functionality.

An mRNA molecule may be flanked with 5'end and 3'end untranslated regions (UTRs). A 5'-UTR serves as the entry site for ribosomes to initiate translation, and a 3' UTR plays an important role in translation termination and post-translational modification, which may influence the expression and half-life of mRNA. A poly A tail of mRNA may make the RNA molecule more stable and prevent mRNA degradation. Additionally, a poly A tail may allow the mature messenger RNA to be exported from nucleus and translated into a protein by ribosomes in the cytoplasm. See, e.g., Sachs A and Wahle E, "Poly(A) tail metabolism and function in eucaryotes", *J Biol Chem*, (1993 Nov. 5); 268(31):22955-8, incorporated herein by reference in its entirety.

An mRNA cap is a highly methylated modification at the 5' end of mRNA, which may protect mRNA from degradation, recruit complexes involved in mRNA processing, and mark cellular mRNA to avoid recognition by immune system. In mammals, the predominant 5' cap structure is an inverted 7-methylguanosine nucleotide bound linked by a 5'-5' triphosphate bond to the first transcribed nucleotide. The 7-methylguanosine is methylated at its 7 carbon position, and may be referred to as $^{m7}G$ or $^7mG$. This cap structure may be expressed as $5'^{m7}GpppN_1(pN)_x$, where N is any nucleotide and x is 0 or any number. In Cap 0 structure, the first nucleotide has a 2' hydroxy group in its ribose sugar, while in Cap 1 structure, the first nucleotide has a 2'-o-methyl modification in the ribose, and this structure may comprise, from 5' end to 3' end, $^{m7}G^{5'}pppN_1^{2'-OMe}(pN)_x$, where N is any nucleotide and x may be any integer. Further, in Cap 2 structure, the 2' hydroxy group of the first and second ribose to the $m^7G$ are methylated. This structure may comprise, from 5' end to 3' end, $^{m7}G^{5'}pppN_1^{2'-OMepN}{}_2^{2'-OMe}(pN)_x$, where N is any nucleotide and x may be any integer. See, e.g., Perry R P, "RNA processing comes of age", *J Cell Biol.* (1981 December); 91(3 Pt 2):28s-38s, incorporated herein by reference in its entirety.

Capping may improve properties of the mRNA, such as, but not limited to, its stability and its translational efficiency. See, e.g., Banerjee A K, "5'-terminal cap structure in eucaryotic messenger ribonucleic acids", *Microbiol Rev.* (1980 June); 44(2):175-205, incorporated herein by reference in its entirety. In vivo, each capping process may be carried out by enzymes. See, e.g., Perry. These processes may be time-consuming, inefficient, and expensive to perform in vitro.

Preparation of capped mRNA through in vitro synthesis may have significant importance for both fundamental scientific research, development of pharmacologic, and development of therapeutics. Several factors may contribute to the generation of mRNA that may have high expression levels, stability, and functionality. There is a need for an efficient in vitro transcriptional method that would allow for more efficient production of capped mRNA that may have high expression levels, stability, functionality, or a combination thereof.

BRIEF SUMMARY

In an aspect, the present disclosure relates to a method for in vitro transcription of a DNA template into RNA, including providing (1) a DNA template comprises a promoter operably linked to a nucleic acid comprising a 5' untranslated region (5' UTR), an open reading frame (ORF) encoding the RNA of interest, a 3' UTR, and a poly A region, and (2) a cap analogue comprises the structure of

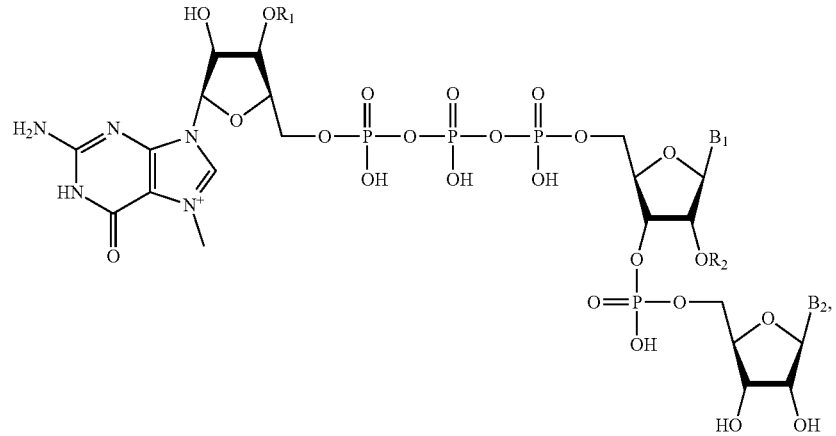

in which $R_1$ and $R_2$ may be each $CH_3$ or H; and $B_1$ and $B_2$ may be each A, U, G, or C, in which the promoter may contain a sequence of TAATACGACTCACTATAX$_1$X$_2$X$_3$ (SEQ ID NO: 16), in which A at position 17 is −1 nucleotide and $X_1$ at position 18 is +1 nucleotide, when $X_1$ is G, $X_2$ and $X_3$ are each A, T, G, or C, then $B_1$ is A and $B_2$ is G, when $X_1$ is A, $X_2$ and $X_3$ are each A, T, G, or C, then $B_1$ is A and $B_2$ is A, when $X_1$ is C, $X_2$ and $X_3$ are each A, T, G, or C, then $B_1$ is A and $B_2$ is C, and when $X_1$ is T, $X_2$ and $X_3$ are each A, T, G, or C, then $B_1$ is A and $B_2$ is U, in which the cap analogue binds to −1 and +1 nucleotides of the promoter, and incubating the DNA template and the cap analogue in a reaction mixture, in which the incubating may include incubating the reaction mixture at from about 15° C. to about 35° C. for from about 1 hour to about 12 hours, thereby producing the RNA.

In another aspect, the promoter may contain a sequence selected from SEQ ID NO: 10, 11, 13, and 14.

In another aspect, the 5' UTR and the 3' UTR may be respectively SEQ ID NO: 1 and 2, 1 and 4, 1 and 6, 3 and 2, 3 and 4, 3 and 6, 3 and 8, 5 and 2, 5 and 4, 5 and 6, 7 and 2, 7 and 4, 7 and 6, 7 and 8, 9 and 2, 9 and 4, 9 and 6, or 9 and 8.

In another aspect, the 5' UTR and the 3' UTR may be respectively SEQ ID NO: 1 and 2, 1 and 4, 3 and 2, 1 and 6, 7 and 4, 9 and 2, or 3 and 6.

In another aspect, the poly A region may contain from about 60 to about 200 As, from about 60 to about 190 As, from about 60 to about 180 As, from about 60 to about 170 As, from about 60 to about 160 As, from about 60 to about 150 As, from about 60 to about 140 As, from about 60 to about 130 As, from about 60 to about 120 As, from about 60 to about 110 As, from about 60 to about 100 As, from about 70 to about 190 As, from about 80 to about 180 As, from about 90 to about 170 As, from about 100 to about 160 As, from about 100 to about 150 As, from about 100 to about 140 As, from about 100 to about 130 As, from about 100 to about 120 As, about 100 As, about 110 As, about 120 As, about 130 As, about 140 As, or about 150 As.

In another aspect, the cap analogue may be selected from the group consisting of m$^7$GpppApA, m$^7$GpppApC, m$^7$GpppApG, m$^7$GpppApU, m$^7$G$_{3'Ome}$pppApA, m$^7$G$_{3'Ome}$pppApC, m$^7$G$_{3'Ome}$pppApG, m$^7$G$_{3'Ome}$pppApU, m$^7$G$_{3'Ome}$pppA$_{2'Ome}$pA, m$^7$G$_{3'Ome}$pppA$_{2'Ome}$pC, m$^7$G$_{3'Ome}$pppA$_{2'Ome}$pG, m$^7$G$_{3'Ome}$pppA$_{2'Ome}$pU, m$^7$GpppA$_{2'Ome}$pA, m$^7$GpppA$_{2'Ome}$pC, m$^7$GpppA$_{2'Ome}$pG, and m$^7$GpppA$_{2'Ome}$pU.

In another aspect, the reaction mixture may contain a buffer substance in a concentration of from about 45 mM to about 55 mM, an RNase inhibitor in a concentration of from about 0.01 U/µl to about 0.03 U/µl, NTPs in a concentration of from about 3 mM to about 5 mM, the cap analogue in a concentration of from about 6 mM to about 8 mM, one or more magnesium salts in a concentration of from about 20 mM to about 30 mM, a polyamine in a concentration of from about 1.5 mM to about 2.5 mM, the DNA template in a concentration of from about 0.01 µg/µl to about 0.05 µg/µl, a pyrophosphatase in a concentration of from about 0.1 mU/µl to about 0.5 mU/µl, and an RNA polymerase in a concentration of from about 0.01 µg/µl to about 0.05 µg/µl.

In another aspect, the RNA polymerase may be selected from wild type T7 RNA polymerase or a variant thereof.

In another aspect, the incubating may include incubating the reaction mixture at from about 18° C. to about 31° C.

In another aspect, the incubating may include incubating the reaction mixture at about 30° C. for about 4 hours.

In another aspect, the DNA template may further contain at least one transcriptional terminator located upstream and/or downstream of the open reading frame (ORF).

In an aspect, the present disclosure relates to a method for in vitro transcription of a DNA template into RNA, including providing a mixture comprising ribonucleoside triphosphates (NTPs), the DNA template, and a RNA polymerase e.g. a recombinant RNA polymerase, and incubating the reaction mixture at from about 15° C. to about 35° C., optionally from about 18° C. to about 31° C., for an appropriate time preferably from about 1 hour to about 12 hours, thereby producing the RNA. Preferably, the mixture further comprises a buffer substance and one or more magnesium salts. The mixture can optionally further comprise a cap analogue.

In an aspect, the present disclosure relates to a method for in vitro transcription of a DNA template into RNA, including providing a mixture comprising a buffer substance, ribonucleoside triphosphates (NTPs), one or more magnesium salts in a concentration of from about 2 mM to about 60 mM, the DNA template, and a recombinant RNA polymerase, and incubating the reaction mixture at from about 15° C. to about 35° C., optionally from about 18° C. to about 31° C., for from about 1 hour to about 12 hours, thereby producing the RNA.

In another aspect, the buffer substance may be Tris base, HEPES, or Tris-HCl.

In another aspect, the concentration of the buffer substance may be from about 1 mM to about 100 mM, from about 1 mM to about 90 mM, from about 1 mM to about 80 mM, from about 1 mM to about 70 mM, from about 1 mM to about 60 mM, from about 1 mM to about 50 mM, from about 1 mM to about 40 mM, from about 1 mM to about 30 mM, from about 1 mM to about 20 mM, from about 1 mM to about 10 mM, from about 1 mM to about 5 mM, from about 10 mM to about 20 mM, from about 10 mM to about 30 mM, from about 10 mM to about 40 mM, from about 10 mM to about 50 mM, from about 20 mM to about 50 mM, from about 30 mM to about 50 mM, from about 40 mM to about 50 mM, from about 45 mM to about 50 mM, from about 45 mM to about 55 mM, from about 15 mM to about 45 mM, from about 15 mM to about 35 mM, from about 15 mM to about 30 mM, or from about 15 mM to about 25 mM.

In another aspect, the concentration of the NTPs may be from about 1 mM to about 50 mM, from about 1 mM to about 40 mM, from about 1 mM to about 30 mM, from about 1 mM to about 20 mM, from about 1 mM to about 10 mM, from about 1 mM to about 5 mM, from about 2 mM to about 10 mM, from about 3 mM to about 10 mM, from about 3 mM to about 9 mM, from about 3 mM to about 8 mM, from about 3 mM to about 7 mM, from about 3 mM to about 6 mM, from about 3 mM to about 5 mM, from about 3 mM to about 4 mM, from about 4 mM to about 10 mM, from about 5 mM to about 10 mM, from about 6 mM to about 10 mM, from about 7 mM to about 10 mM, from about 8 mM to about 10 mM, or from about 9 mM to about 10 mM.

In another aspect, the concentration of the one or more magnesium salts may be from about 2 mM to about 50 mM, from about 2 mM to about 40 mM, from about 2 mM to about 30 mM, from about 2 mM to about 40 mM, from about 2 mM to about 30 mM, from about 2 mM to about 20 mM, from about 2 mM to about 10 mM, from about 2 mM to about 5 mM, from about 5 mM to about 50 mM, from about 10 mM to about 45 mM, from about 15 mM to about 40 mM, from about 20 mM to about 35 mM, from about 20 mM to about 30 mM, from about 20 mM to about 25 mM, from about 22 mM to about 28 mM, or from about 25 mM to about 30 mM.

In another aspect, the concentration of the DNA template may be from about 0.001 µg/µl to about 2 µg/µl, from about 0.001 µg/µl to about 1.5 µg/µl, from about 0.001 µg/µl to about 1 µg/µl, from about 0.01 µg/µl to about 2 µg/µl, from about 0.01 µg/µl to about 1.5 µg/µl, from about 0.01 µg/µl to about 1 µg/µl, from about 0.01 µg/µl to about 0.5 µg/µl, from about 0.01 µg/µl to about 0.1 µg/µl, from about 0.01 µg/µl to about 0.05 µg/µl, from about 0.02 µg/µl to about 0.04 µg/µl, from about 0.02 µg/µl to about 0.1 µg/µl, from about 0.03 µg/µl to about 0.1 µg/µl, from about 0.04 µg/µl to about 0.1 µg/µl, from about 0.05 µg/µl to about 0.1 µg/µl, from about 0.06 µg/µl to about 0.1 µg/µl, from about 0.07 µg/µl to about 0.1 µg/µl, from about 0.08 µg/µl to about 0.1 µg/µl, or from about 0.09 µg/µl to about 0.1 µg/µl.

In another aspect, the concentration of the recombinant RNA polymerase may be from about 0.001 µg/µl to about 2 µg/µl, from about 0.001 µg/µl to about 1.5 µg/µl, from about 0.001 µg/µl to about 1 µg/µl, from about 0.01 µg/µl to about 1 µg/µl, from about 0.01 µg/µl to about 0.5 µg/µl, from about 0.01 µg/µl to about 0.3 µg/µl, from about 0.01 µg/µl to about 0.1 µg/µl, from about 0.01 µg/µl to about 0.05 µg/µl, from about 0.1 µg/µl to about 1 µg/µl, from about 0.1 µg/µl to about 0.9 µg/µl, from about 0.1 µg/µl to about 0.8 µg/µl, from about 0.1 µg/µl to about 0.7 µg/µl, from about 0.1 µg/µl to about 0.6 µg/µl, from about 0.1 µg/µl to about 0.5 µg/µl, from about 0.1 µg/µl to about 0.4 µg/µl, from about 0.1 µg/µl to about 0.3 µg/µl, or from about 0.1 µg/µl to about 0.2 µg/µl.

In another aspect, the mixture may further contain an antioxidant.

In another aspect, the antioxidant may be dithiothreitol (DTT) in a concentration of from about 1 mM to about 50 mM, from about 2 mM to about 50 mM, from about 3 mM to about 50 mM, from about 4 mM to about 50 mM, from about 5 mM to about 50 mM, from about 6 mM to about 50 mM, from about 7 mM to about 50 mM, from about 8 mM to about 50 mM, from about 9 mM to about 50 mM, from about 10 mM to about 50 mM, from about 10 mM to about 40 mM, from about 15 mM to about 30 mM, from about 15 mM to about 25 mM, from about 15 mM to about 20 mM, from about 20 mM to about 50 mM, from about 30 mM to about 50 mM, or from about 40 mM to about 50 mM.

In another aspect, the mixture may further contain an RNase inhibitor in a concentration of from about 0.001 U/µl to about 5 U/µl, from about 0.001 U/µl to about 4 U/µl, from about 0.001 U/µl to about 3 U/µl, from about 0.001 U/µl to about 2 U/µl, from about 0.001 U/µl to about 1 U/µl, from about 0.01 U/µl to about 5 U/µl, from about 0.01 U/µl to about 4 U/µl, from about 0.01 U/µl to about 3 U/µl, from about 0.01 U/µl to about 2 U/µl, from about 0.01 U/µl to about 1 U/µl, from about 0.01 U/µl to about 0.5 U/µl, from about 0.01 U/µl to about 0.1 U/µl, from about 0.01 U/µl to about 0.05 U/µl, from about 0.01 U/µl to about 0.04 U/µl, from about 0.01 U/µl to about 0.03 U/µl, from about 0.01 U/µl to about 0.02 U/µl, from about 0.1 U/µl to about 5 U/µl, from about 0.1 U/µl to about 4 U/µl, from about 0.1 U/µl to about 3 U/µl, from about 0.1 U/µl to about 2 U/µl, from about 0.1 U/µl to about 1 U/µl, from about 0.5 U/µl to about 5 U/µl, from about 0.5 U/µl to about 4 U/µl, from about 0.5 U/µl to about 3 U/µl, from about 0.5 U/µl to about 2 U/µl, from about 0.5 U/µl to about 1 U/µl, from about 1 U/µl to about 5 U/µl, from about 2 U/µl to about 5 U/µl, from about 3 U/µl to about 5 U/µl, or from about 4 U/µl to about 5 U/µl.

In another aspect, the mixture may further contain a cap analogue in a concentration of from about 0.5 mM to about 50 mM, from about 0.5 mM to about 40 mM, from about 0.5 mM to about 30 mM, from about 0.5 mM to about 20 mM, from about 0.5 mM to about 10 mM, from about 0.5 mM to about 5 mM, from about 1 mM to about 10 mM, from about 2 mM to about 10 mM, from about 3 mM to about 10 mM, from about 3 mM to about 9 mM, from about 3 mM to about 8 mM, from about 3 mM to about 7 mM, from about 3 mM to about 6 mM, from about 3 mM to about 5 mM, from about 3 mM to about 4 mM, from about 4 mM to about 10 mM, from about 5 mM to about 10 mM, from about 6 mM to about 10 mM, from about 6 mM to about 9 mM, from about 6 mM to about 8 mM, from about 6 mM to about 7 mM, from about 7 mM to about 10 mM, from about 8 mM to about 10 mM, or from about 9 mM to about 10 mM.

In another aspect, the mixture may further contain a polyamine.

In another aspect, the polyamine may be spermine, spermidine, or a combination thereof.

In another aspect, the concentration of the polyamine may be from about 0.1 mM to about 5 mM, from about 0.2 mM to about 4.9 mM, from about 0.2 mM to about 4.8 mM, from about 0.2 mM to about 4.7 mM, from about 0.2 mM to about 4.6 mM, from about 0.2 mM to about 4.5 mM, from about 0.2 mM to about 4.4 mM, from about 0.2 mM to about 4.3 mM, from about 0.2 mM to about 4.2 mM, from about 0.2 mM to about 4.1 mM, from about 0.2 mM to about 4 mM, from about 0.2 mM to about 3.5 mM, from about 0.2 mM to about 3 mM, from about 0.2 mM to about 2.5 mM, from about 0.5 mM to about 2.5 mM, from about 1.0 mM to about 2.5 mM, from about 1.5 mM to about 2.5 mM, from about 0.2 mM to about 2 mM, from about 0.2 mM to about 1.5 mM, from about 0.2 mM to about 1 mM, from about 0.2 mM to about 0.9 mM, from about 0.2 mM to about 0.8 mM, from about 0.2 mM to about 0.7 mM, from about 0.2 mM to about 0.6 mM, from about 0.2 mM to about 0.5 mM, from about 0.2 mM to about 0.4 mM, or from about 0.2 mM to about 0.3 mM.

In another aspect, the mixture may further contain a pyrophosphatase in a concentration of from about 0.01 mU/µl to about 2 mU/µl, from about 0.01 mU/µl to about 1.5 mU/µl, from about 0.01 mU/µl to about 1 mU/µl, from about 0.1 mU/µl to about 2 mU/µl, from about 0.1 mU/µl to about 1.5 mU/µl, from about 0.1 mU/µl to about 1 mU/µl, from about 0.1 mU/µl to about 0.9 mU/µl, from about 0.1 mU/µl to about 0.8 mU/µl, from about 0.1 mU/µl to about 0.7 mU/µl, from about 0.1 mU/µl to about 0.6 mU/µl, from about 0.1 mU/µl to about 0.5 mU/µl, from about 0.1 mU/µl to about 0.4 mU/µl, from about 0.1 mU/µl to about 0.3 mU/µl, or from about 0.1 mU/µl to about 0.2 mU/µl.

In another aspect, the incubating the reaction mixture may be performed at from about 15° C. to about 35° C., from about 16° C. to about 35° C., from about 17° C. to about 35° C., from about 18° C. to about 35° C., from about 18° C. to about 34° C., from about 18° C. to about 33° C., from about 18° C. to about 32° C., from about 18° C. to about 31° C., from about 18° C. to about 30° C., from about 18° C. to about 29° C., from about 18° C. to about 28° C., from about 18° C. to about 27° C., from about 18° C. to about 26° C., from about 18° C. to about 25° C., from about 18° C. to about 24° C., from about 18° C. to about 23° C., from about 18° C. to about 22° C., from about 18° C. to about 21° C., from about 18° C. to about 20° C., from about 18° C. to about 19° C., from about 25° C. to about 26° C., from about 25° C. to about 27° C., from about 25° C. to about 28° C., from about 25° C. to about 29° C., from about 25° C. to about 30° C., from about 25° C. to about 31° C., from about 21° C. to about 22° C., from about 21° C. to about 23° C., from about 21° C. to about 24° C., or from about 21° C. to about 25° C.

In another aspect, the incubating the reaction mixture may be performed for from about 1 hour to about 12 hours, from about 1 hour to about 11 hours, from about 1 hour to about 10 hours, from about 1 hour to about 9 hours, from about 1 hour to about 8 hours, from about 1 hour to about 7 hours, from about 1 hour to about 6 hours, from about 1 hour to about 5 hours, from about 1 hour to about 4 hours, from about 1 hour to about 3 hours, from about 1 hour to about 2 hours, from about 2 hours to about 12 hours, from about 3 hours to about 12 hours, from about 4 hours to about 12 hours, from about 5 hours to about 12 hours, from about 6 hours to about 12 hours, from about 7 hours to about 12 hours, from about 8 hours to about 12 hours, from about 9 hours to about 12 hours, from about 10 hours to about 12 hours, or from about 11 hours to about 12 hours.

In another aspect, the incubating the reaction mixture may be performed at about 25° C. for from about 1 hour to about 5 hours, from about 1.5 hours to about 4.5 hours, from about 2 hours to about 4 hours, from about 2.5 hours to about 3.5 hours, or from about 2.5 hours to about 3 hours.

In another aspect, the incubating the reaction mixture may be performed at about 31° C. for from about 1 hour to about 5 hours, from about 1 hour to about 4.5 hours, from about 1 hour to about 4 hours, from about 1 hour to about 3.5 hours, from about 1 hour to about 3 hours, from about 1 hour to about 2.5 hours, from about 1 hour to about 2 hours, from about 1 hour to about 1.5 hours, from about 0.5 hour to about 1 hour, or from about 0.5 hour to about 1.5 hours.

In another aspect, the DNA template may include a promoter operably linked to a nucleic acid comprising a 5' untranslated region (5' UTR), an open reading frame (ORF) encoding the RNA of interest, a 3' UTR, and a poly A region, in which the promoter may contain a sequence of TAATACGACTCACTATAX$_1$X$_2$X$_3$ (SEQ ID NO: 16), in which X$_1$ is A or G, X$_2$ is A or G, and X$_3$ is A, T, G, or C, in which the 5' UTR may be selected from SEQ ID NO: 1, 3, 5, or 9, and the 3' UTR may be selected from SEQ ID NO: 2, 4, 6, or 8, in which the poly A region comprises at least 60 adenine bases (As).

In another aspect, the promoter may contain a sequence selected from SEQ ID NO: 10-15.

In another aspect, the cap analogue may bind to −1 and/or +1 nucleotide of the promoter.

In an aspect, the present disclosure relates to a reaction mixture for in vitro transcription of a DNA template into RNA, containing a buffer substance in a concentration of from about 45 mM to about 55 mM, an RNase inhibitor in a concentration of from about 0.01 U/µl to about 0.03 U/µl, NTPs in a concentration of from about 3 mM to about 5 mM, a cap analogue in a concentration of from about 6 mM to about 8 mM, one or more magnesium salts in a concentration of from about 20 mM to about 30 mM, a polyamine in a concentration of from about 1.5 mM to about 2.5 mM, a DNA template in a concentration of from about 0.01 µg/µl to about 0.05 µg/µl, a pyrophosphatase in a concentration of from about 0.1 mU/µl to about 0.5 mU/µl, and an RNA polymerase in a concentration of from about 0.01 µg/µl to about 0.05 µg/µl.

In another aspect, the one or more magnesium salts may be MgCl$_2$ and/or magnesium acetate (Mg(C$_2$H$_3$O$_2$)$_2$) (MgOAc).

In an aspect, the present disclosure relates to a method for in vitro transcription of a DNA template into RNA, including providing the reaction mixture of the present disclosure, and incubating the reaction mixture at from about 15° C. to about 35° C. for from about 1 hour to about 12 hours, thereby producing the RNA.

DETAILED DESCRIPTION

Figure 1A:
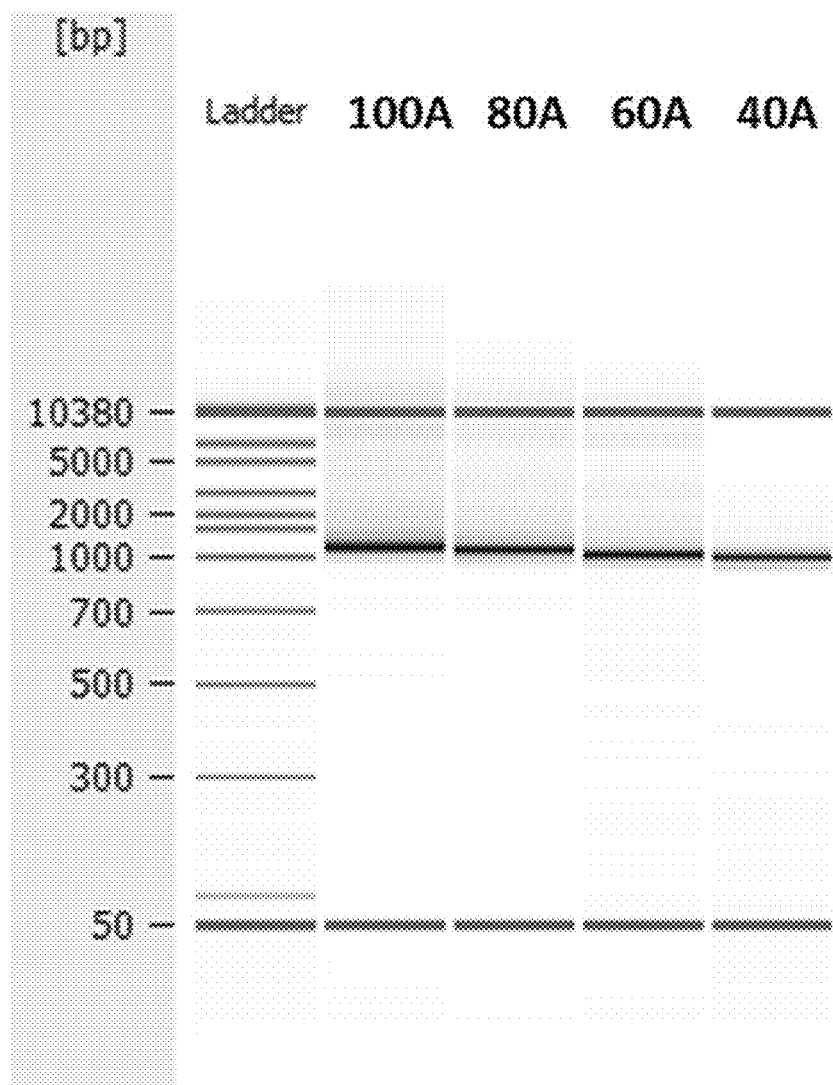
FIG. 1A shows poly-A tails of different lengths were added to DNA template in accordance with one embodiment of the present disclosure.

Provided herein are methods and compositions for in vitro synthesis of mRNA. mRNA may also comprise one or more cap, and methods and compositions for in vitro synthesis of capped mRNA are provided. mRNA may also comprise a poly-A tail, and methods and compositions for in vitro synthesis of mRNA having a poly-A tail are provided. Aspects of the disclosed methods and compositions may be used singly or in any combination. The disclosed methods and compositions may improve efficiency of mRNA synthesis and may provide mRNA with improved properties.

Advantages of the present disclosure may include, for example, improved yield of mRNA, improved purity of mRNA, improved capping efficiency, and improved uniformity of length and/or distribution of poly-A tails. Improvements in time- and/or cost-efficiency may also be realized.

The disclosed methods and compositions may be used singly or in any combination to perform in vitro synthesis of mRNA of different sizes, such as, but not limited to, mRNAs ranging from about 100 b to about 20 Kb, from about 200 b to about 19 Kb, from about 300 b to about 18 Kb, from about 400 b to about 17 Kb, from about 500 b to about 16 Kb, from about 600 b to about 15 Kb, from about 700 b to about 14 Kb, from about 800 b to about 13 Kb, from about 900 b to about 12 Kb, from about 1 Kb to about 11 Kb, from about 1 Kb to about 10 Kb, from about 1 Kb to about 9 Kb, from about 1 Kb to about 8 Kb, from about 1 Kb to about 7 Kb, from about 1 Kb to about 6 Kb, from about 1 Kb to about 5 Kb, from about 1 Kb to about 4 Kb, from about 1 Kb to about 3 Kb, from about 1 Kb to about 2 Kb, from about 50 b to about 200 b, from about 60 b to about 190 b, from about 70 b to about 180 b, from about 80 b to about 160 b, from about 90 b to about 100 b, from about 90 b to about 110 b, from about 90 b to about 120 b, from about 90 b to about 130 b, from about 90 b to about 140 b, from about 90 b to about 150 b, from about 100 b to about 140 b, from about 110 b to about 130 b, or from about 110 b to about 120 b.

mRNA synthesized using the disclosed compositions and/or methods may have may applications, including, but not limited to, uses in fundamental scientific research, uses in development of pharmacologics, uses in development of diagnostics, uses in development of therapeutics, uses as pharmacologics, uses as diagnostics, uses as therapeutics, or any combination thereof.

Methods for RNA in vitro transcription are known in the art (see for example Geall et al. (2013) *Semin. Immunol.* 25(2): 152-159; Brunelle et al. (2013) *Methods Enzymol.* 530: 101-14). Reagents used in said methods may include: a linear DNA template with a promoter sequence that has a high binding affinity for its respective RNA polymerase; ribonucleoside triphosphates (NTPs) for the four bases (adenine, cytosine, guanine and uracil); a cap analogue (e.g., m7G(5')ppp(5')G (m7G)); other modified nucleotides; DNA-dependent RNA polymerase (e.g., T7, T3 or SP6 RNA polymerase); ribonuclease (RNase) inhibitor to inactivate any contaminating Rnase; pyrophosphatase to degrade pyrophosphate, which inhibits transcription; $MgCl_2$ and/or MgOAc, which supplies $Mg^{2+}$ as a cofactor for the RNA polymerase; antioxidants (e.g. DTT); polyamines, such as spermidine; and a buffer to maintain a suitable pH value.

Common buffer systems used in RNA in vitro transcription may include 4-(2-hydroxy-ethyl)-1-piperazineethanesulfonic acid (HEPES) and tris(hydroxymethyl)aminomethane (Tris). The pH value of the buffer may be commonly adjusted to a pH value of 6 to 8.5. Some commonly used transcription buffers may contain 80 mM HEPES/KOH, pH 7.5 and 40 mM Tris/HCl, pH 7.5.

The transcription buffer may also contain a magnesium salt, such as $MgCl_2$ and/or MgOAc commonly in a range between 5-50 mM. Magnesium ions ($Mg^{2+}$) may be an essential component in an RNA in vitro transcription buffer system because free $Mg^{2+}$ may function as cofactor in the catalytic center of the RNA polymerase and may be critical for the RNA polymerization reaction. In diffuse binding, fully hydrated Mg ions may also interact with the RNA product via nonspecific long-range electrostatic interactions.

RNA in vitro transcription reactions may be performed as batch reactions in which all components are combined and then incubated to allow the synthesis of RNA molecules until the reaction terminates. In addition, fed-batch reactions were developed to increase the efficiency of the RNA in vitro transcription reaction (Kern et al. (1997) *Biotechnol. Prog.* 13: 747-756; Kern et al. (1999) *Biotechnol. Prog.* 15: 174-184). In a fed-batch system, all components are combined, but then additional amounts of some of the reagents are added over time (e.g., NTPs, $MgCl_2$ and/or MgOAc) to maintain constant reaction conditions.

For the sake of clarity and readability the following definitions are provided. Any technical feature mentioned in these definitions may be read on each and every embodiment of the invention. Additional definitions and explanations may be specifically provided in the context of these embodiments.

In vitro transcription: The terms "in vitro transcription" or "RNA in vitro transcription" may relate to a process wherein RNA is synthesized in a cell-free system (in vitro). DNA, particularly plasmid DNA, is used as template for the generation of RNA transcripts. RNA may be obtained by DNA-dependent in vitro transcription of an appropriate DNA template, which according to the present disclosure, may be preferably a linearized plasmid DNA template. The promoter for controlling in vitro transcription can be any promoter for any DNA-dependent RNA polymerase. Particular non-limiting examples of DNA-dependent RNA polymerases are the T7, T3, and SP6 RNA polymerases. A DNA template for in vitro RNA transcription may be obtained, for example, by cloning of a nucleic acid, in particular cDNA corresponding to the respective RNA to be in vitro transcribed, and introducing it into an appropriate vector for in vitro transcription, for example, into plasmid DNA. In a preferred embodiment of the present disclosure, DNA template may be linearized with a suitable restriction enzyme before it is transcribed in vitro. The cDNA may be obtained by reverse transcription of mRNA or chemical synthesis. Moreover, the DNA template for in vitro RNA synthesis may also be obtained by gene synthesis.

For example, reagents used in in vitro transcription may include:

1) a linearized DNA template with a promoter sequence that has a high binding affinity for its respective RNA polymerase such as bacteriophage-encoded RNA polymerases;
2) ribonucleoside triphosphates (NTPs) for the four bases (adenine, cytosine, guanine and uracil);
3) optionally a cap analogue as defined below (e.g. m7G(5')ppp(5')A (m7G));
4) a DNA-dependent RNA polymerase capable of binding to the promoter sequence within the linearized DNA template (e.g. T7, T3 or SP6 RNA polymerase);
5) optionally a ribonuclease (Rnase) inhibitor to inactivate any contaminating Rnase;
6) optionally a pyrophosphatase to degrade pyrophosphate, which may inhibit transcription;
7) $MgCl_2$ and/or magnesium acetate ($Mg(C_2H_3O_2)_2$) (MgOAc), which supplies $Mg^{2+}$ ions as a co-factor for the polymerase;
8) a buffer to maintain a suitable pH value, which can also contain antioxidants (e.g., DTT), amines, such as, betaine and/or polyamines, such as, spermidine at optimal concentrations.

In embodiments, in the method of RNA in vitro transcription according to the present disclosure, no reagents, which are only required for the in vitro translation of the transcribed RNA to protein, but not for RNA in vitro transcription are used. In particular, the mixture used for RNA in vitro transcription may not contain any proteinogenic amino acid or tRNA. Further, the mixture may not contain any proteinogenic amino acid, tRNA or a cell extract containing ribosomes.

The term "co-transcription" used herein refers to mRNA prepared as with a cap structure through one step in vitro transcription reaction using RNA polymerase, e.g., T7 RNA polymerase. In contrast, one or more traditional post transcriptional capping method may need to prepare an uncapped RNA through in vitro transcription (IVT) with RNA polymerase, and then add Cap using capping enzyme, e.g., vaccinia capping enzyme, with the aid of 2'-O-Methyltransferase to add methylation at the +1 base of the mRNA.

Nucleic acid: The term "nucleic acid" means any DNA- or RNA-molecule and is used synonymous with polynucleotide. Furthermore, modifications or derivatives of the nucleic acid as defined herein are explicitly included in the general term "nucleic acid." For example, peptide nucleic acid (PNA) is also included in the term "nucleic acid."

Nucleic acid template: The nucleic acid template provides the nucleic acid sequence that is transcribed into the RNA by the process of in vitro transcription and which therefore comprises a nucleic acid sequence which is complementary to the RNA sequence that is transcribed therefrom. In addition to the nucleic acid sequence, which is transcribed into the RNA, the nucleic acid template comprises a promoter to which the RNA polymerase used in the in vitro transcription process binds with high affinity.

Preferably, the nucleic acid template may be a linearized plasmid DNA template. The linear template DNA may be obtained by contacting plasmid DNA with a restriction enzyme under suitable conditions so that the restriction enzyme cuts the plasmid DNA at its recognition site(s) and disrupts the circular plasmid structure. The plasmid DNA is preferably cut immediately after the end of the sequence that is to be transcribed into RNA. Hence, the linear template DNA comprises a free 5' end and a free 3' end, which are not linked to each other. If the plasmid DNA contains only one recognition site for the restriction enzyme, the linear template DNA has the same number of nucleotides as the plasmid DNA. If the plasmid DNA contains more than one recognition site for the restriction enzyme, the linear template DNA has a smaller number of nucleotides than the plasmid DNA. The linear template DNA is then the fragment of the plasmid DNA that contains the elements necessary for in vitro transcription, which is a promotor element for RNA transcription and the template DNA element. The open reading frame (ORF) of the linear template DNA may determine the sequence of the transcribed RNA by the rules of base-pairing.

In other embodiments, nucleic acid template may be selected from a synthetic double stranded DNA construct, a single-stranded DNA template with a double-stranded DNA region comprising the promoter to which the RNA polymerase binds, a cyclic double-stranded DNA template with promoter and terminator sequences or a linear DNA template amplified by PCR or isothermal amplification.

According to a preferred embodiment of the present disclosure, the concentration of nucleic acid template comprised in the in vitro transcription mixture described herein may be in a range from about 1 to about 200 nM, from about 10 nM to about 150 nM, from about 20 nM to about 140 nM, from about 30 nM to about 130 nM, from about 40 nM to about 120 nM, from about 50 nM to about 110 nM, from about 60 nM to about 100 nM, from about 65 nM to about 90 nM, from about 65 nM to about 80 nM, from about 65 nM to about 75 nM, from about 65 nM to about 70 nM, from about 70 nM to about 75 nM, about 1 to about 40 nM, about 1 to about 30 nM, about 1 to about 20 nM, or about 1 to about 10 nM. Even more preferred the concentration of the nucleic acid template may be from about 10 to about 30 nM. Most preferred the concentration of the nucleic acid template may be about 40, 50, 60, 70, 80, 90, or 100 nM.

RNA, mRNA: RNA is the usual abbreviation for ribonucleic acid. It is a nucleic acid molecule, i.e., a polymer consisting of nucleotide monomers. These nucleotides are usually adenosine-monophosphate (AMP), uridine-monophosphate (UMP), guanosine-monophosphate (GMP) and cytidine-monophosphate (CMP) monomers or analogues thereof, which are connected to each other along a so-called backbone. The backbone is formed by phosphodiester bonds between the sugar, i.e., ribose, of a first and a phosphate moiety of a second, adjacent monomer. The specific order of the monomers, i.e., the order of the bases linked to the sugar/phosphate-backbone, is called the RNA sequence. Usually RNA may be obtainable by transcription of a DNA sequence, e.g., inside a cell. In eukaryotic cells, transcription is typically performed inside the nucleus or the mitochondria. In vivo, transcription of DNA usually results in so-called premature RNA which has to be processed into so-called messenger-RNA, usually abbreviated as mRNA. Processing of the premature RNA, e.g., in eukaryotic organisms, comprises a variety of different posttranscriptional-modifications, such as, splicing, 5'-capping, polyadenylation, export from the nucleus or the mitochondria and the like. The sum of these processes is also called maturation of RNA. The mature messenger RNA usually provides nucleotide sequence that may be translated into an amino acid sequence of a particular peptide or protein. Typically, a mature mRNA comprises a 5'-cap, optionally a 5' UTR, an open reading frame, optionally a 3'UTR, and a poly(A) sequence.

In addition to messenger RNA, several non-coding types of RNA exist, which may be involved in regulation of transcription and/or translation, and immunostimulation. The term "RNA" further encompasses RNA molecules, such as viral RNA, retroviral RNA and replicon RNA, small interfering RNA (siRNA), antisense RNA, CRISPR/Cas9 guide RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

Dicarboxylic acid or salt thereof: A dicarboxylic acid is an organic acid having two carboxyl groups (—COOH). The term includes linear saturated dicarboxylic acids having the general formula $HO_2C$—$(CH_2)_n$—$CO_2H$ such as oxalic acid, malonic acid, succinic acid, glutaric acid, adipic acid, pimelic acid, suberic acid, azelaic acid and sebacic acid. It also includes unsaturated dicarboxylic acids having at least one double bond such as maleic acid and fumaric acid as well as substituted dicarboxylic acids having at least one additional functional group such as malic acid, tartaric acid, cichoric acid and dimercaptosuccinic acid. The salt of the dicarboxylic acid comprises the dicarboxylic acid anion and a suitable cation such as $Na^+$, $K^+$, $Ca^{2+}$ or $Mg^{2+}$.

Tricarboxylic acid or salt thereof: A tricarboxylic acid is an organic acid having three carboxyl groups (—COOH). Examples of tricarboxylic acids include citric acid, isocitric acid, aconitic acid, trimesic acid, nitrilotriacetic acid and propane-1,2,3-tricarboxylic acid. In the buffer system and methods of the present invention preferably citric acid (3-carboxy-3-hydroxypentane-1,5-dioic acid) is used. The salt of the tricarboxylic acid comprises the tricarboxylic acid anion and a suitable cation, such as $Na^+$, $K^+$, $Ca^{2+}$ or $Mg^{2+}$. Preferably, sodium or magnesium citrate is used. If magnesium citrate is added to the RNA in vitro transcription reaction, it may be not necessary to add a magnesium salt to the reaction, since the magnesium ions within the magnesium citrate may serve as the cofactor for the RNA polymerase. Hence, in this case the reaction mixture for RNA in vitro transcription comprises magnesium citrate, a buffer substance, ribonucleoside triphosphates, a nucleic acid template and RNA polymerase.

Buffer substance: A buffer substance is a weak acid or base used to maintain the acidity (pH) of a solution near a chosen value after the addition of another acid or base. Hence, the function of a buffer substance is to prevent a rapid change in pH when acids or bases are added to the solution. Suitable buffer substances for use in the present invention include Tris (2-amino-2-hydroxymethyl-propane-1,3-diol) and HEPES (2-[4-(2-hydroxyethyl)piperazin-1-yl] ethanesulfonic acid). The buffer substance may further comprise an acid or a base for adjusting the pH, such as HCl in case of Tris (Tris-HCl) and KOH in case of HEPES (HEPES-KOH). In a preferred embodiment of the present invention citric acid is used to adjust the pH of the buffer substance, preferably of Tris base, so that no other acid has to be added. In an alternative embodiment the pH of the buffer substance is adjusted with an acid or a base such as HCl and KOH and the salt of the dicarboxylic or tricarboxylic acid, preferably citrate, is present in the reaction mixture in addition to the pH-adjusted buffer substance.

The concentration of the buffer substance within the mixture for in vitro transcription described herein may be about 10 to about 100 mM, about 10 to about 80 mM, about 10 to about 50 mM, about 10 to about 40 mM, about 10 to about 30 mM or about 10 to about 20 mM. Preferably, the concentration of the buffer substance is 80 mM.

Preferably the buffer has a pH value from about 6 to about 8.5, from about 6.5 to about 8.0, from about 7.0 to about 7.5, even more preferred of about 7.5 or about 8.0.

Ribonucleoside triphosphates: The ribonucleoside triphosphates (NTPs) GTP, ATP, CTP and UTP are the monomers that are polymerized during the in vitro transcription process. They may be provided with a monovalent or divalent cation as counterion. Preferably the monovalent cation is selected from the group consisting of $Li^+$, $Na^+$, $K^+$, $NH_4^+$ or tris(hydroxymethyl)-aminomethane (Tris). Preferably, the divalent cation is selected from the group consisting of $Mg^{2+}$, $Ba^{2+}$ and $Mn^{2+}$. More preferably, the monovalent cation is $Na^+$ or tris(hydroxymethyl)-aminomethane (Tris).

According to a preferred embodiment of the invention, a part or all of at least one ribonucleoside triphosphate in the in vitro transcription reaction mixture is replaced with a modified nucleoside triphosphate as defined below.

Modified nucleoside triphosphate: The term "modified nucleoside triphosphate" as used herein refers to chemical modifications comprising backbone modifications as well as sugar modifications or base modifications. These modified nucleoside triphosphates are also termed herein as (nucleotide) analogues.

In this context, the modified nucleoside triphosphates as defined herein are nucleotide analogues/modifications, e.g., backbone modifications, sugar modifications or base modifications. A backbone modification in connection with the present invention is a modification, in which phosphates of the backbone of the nucleotides are chemically modified. A sugar modification in connection with the present invention is a chemical modification of the sugar of the nucleotides. Furthermore, a base modification in connection with the present invention is a chemical modification of the base moiety of the nucleotides. In this context nucleotide analogues or modifications are preferably selected from nucleotide analogues which are applicable for transcription and/or translation.

Sugar Modifications

The modified nucleosides and nucleotides, which may be used in the context of the present invention, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —$O(CH_2CH_2O)_nCH_2CH_2OR$; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g., $NH_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleotide can include nucleotides containing, for instance, arabinose as the sugar.

Backbone Modifications

The phosphate backbone may further be modified in the modified nucleosides and nucleotides. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications

The modified nucleosides and nucleotides, which may be used in the present disclosure, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications may be selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides may include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides may include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides may include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides may include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O—(I-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments the modified nucleotides may include nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-isocytidine, 6-Chloro-purine, N6-methyl-adenosine, α-thio-adenosine, 8-azidoadenosine, 7-deaza-adenosine.

Magnesium salt: A magnesium salt comprises a magnesium cation and a suitable anion, such as a chloride or an acetate anion. Preferably, the magnesium salt is magnesium chloride. In the in vitro transcription mixture(s) described herein. Preferably, the initial free $Mg^{2+}$ concentration may be from about 1 to about 100 mM, about 1 to about 75 mM, about 1 to about 50 mM, about 1 to about 25 mM, or about 1 to about 10 mM. Even more preferred the initial free $Mg^{2+}$ concentration is from about 5 to about 50 mM, about 10 to about 45 mM, about 15 to about 40 mM, or about 16 to about 37 mM, for example, about 15, 16, 17, 18, 19, 20, 21, 22, 23, 24, 25, 26, 27, 28, 29, 30, 31, 32, 33, 34, 35, 36, or 37 mM. The person skilled in the art may understand that the choice of the $Mg^{2+}$ concentration may be influenced by the initial total NTP concentration, meaning that a higher $Mg^{2+}$ concentration may need to be used, if a higher total NTP concentration is used in the in vitro transcription mixture. In some embodiments, the concentration of magnesium salt may be from about 2 mM to about 50 mM, from about 2 mM to about 40 mM, from about 2 mM to about 30 mM, from about 2 mM to about 40 mM, from about 2 mM to about 30 mM, from about 2 mM to about 20 mM, from about 2 mM to about 10 mM, from about 2 mM to about 5 mM, from about 5 mM to about 50 mM, from about 10 mM to about 45 mM, from about 15 mM to about 40 mM, from about 20 mM to about 35 mM, from about 20 mM to about 30 mM, from about 20 mM to about 25 mM, from about 22 mM to about 28 mM, or from about 25 mM to about 30 mM.

RNA polymerase: RNA polymerase is an enzyme that catalyses transcription of DNA template into RNA. Suitable RNA polymerases for use in the present disclosure may include T7, T3, SP6 and E. coli RNA polymerase. Preferably, T7 RNA polymerase may be used. Also preferably, the RNA polymerase for use in the present disclosure may be recombinant RNA polymerase, meaning that it is added to the RNA in vitro transcription reaction as a single component and not as part of a cell extract that contains other components in addition to the RNA polymerase. A skilled person knows that the choice of the RNA polymerase depends on the promoter present in the DNA template, which has to be bound by the suitable RNA polymerase. Preferably, the concentration of the RNA polymerase in the in vitro transcription mixture(s) described herein may be from about 0.001 µg/µl to about 2 µg/µl, from about 0.001 µg/µl to about 1.5 µg/µl, from about 0.001 µg/µl to about 1 µg/µl, from about 0.01 µg/µl to about 1 µg/µl, from about 0.01 µg/µl to about 0.5 µg/µl, from about 0.01 µg/µl to about 0.5 µg/µl, from about 0.01 µg/µl to about 0.1 µg/µl, from about 0.01 µg/µl to about 0.05 µg/µl, from about 0.1 µg/µl to about 1 µg/µl, from about 0.1 µg/µl to about 0.9 µg/µl, from about 0.1 µg/µl to about 0.8 µg/µl, from about 0.1 µg/µl to about 0.7 µg/µl, from about 0.1 µg/µl to about 0.6 µg/µl, from about 0.1 µg/µl to about 0.5 µg/µl, from about 0.1 µg/µl to about 0.4 µg/µl, from about 0.1 µg/µl to about 0.3 µg/µl, or from about 0.1 µg/µl to about 0.2 µg/µl. A person skilled in the art can understand that the choice of RNA polymerase concentration may be influenced by the concentration of DNA template.

Pyrophosphatase: A pyrophosphatase is an acid anhydride hydrolase that hydrolyses diphosphate bonds. In the in vitro transcription reaction, it may serve to hydrolyze the bonds within the diphosphate released upon incorporation of the ribonucleoside triphosphates into the nascent RNA chain. Preferably, the concentration of the pyrophosphatase in the in vitro transcription mixture(s) described herein may be from about 1 to about 100 units/ml, from about 10 units/ml to about 90 units/ml, from about 20 units/ml to about 80 units/ml, from about 30 units/ml to about 70 units/ml, from about 40 units/ml to about 60 units/ml, from about 45 units/ml to about 55 units/ml, from about 45 units/ml to about 50 units/ml, from about 50 units/ml to about 55 units/ml, from about 10 units/ml to about 50 units/ml, from about 15 units/ml to about 40 units/ml, from about 20 units/ml to about 30 units/ml, from about 20 units/ml to about 25 units/ml, from about 25 units/ml to about 30 units/ml, about 1 to about 15 units/ml, about 1 to about 10 units/ml, about 1 to about 5 units/ml, or about 1 to about 2.5 units/ml. Even more preferred the concentration of the pyrophosphatase may be about 50 unit/ml or may be about 25 units/ml.

5'-Cap structure: A 5' cap is typically a modified nucleotide, particularly a guanine nucleotide, added to the 5' end of an RNA molecule. Preferably, 5' cap may be added using a 5'-5'-triphosphate linkage. A 5' cap may be methylated, e.g., m7GpppN, wherein N is the terminal 5' nucleotide of the nucleic acid carrying the 5' cap, typically the 5'-end of an RNA. The naturally occurring 5' cap may include m7GpppN.

Further examples of 5' cap structures may include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety.

Particularly preferred 5' cap structures may be CAP1 (methylation of the ribose of the adjacent nucleotide of m7G).

A 5' cap structure may be formed by a cap analogue.

Cap analogue: A cap analogue refers to a non-extendable di-nucleotide or tri-nucleotide that has cap functionality which means that it facilitates translation or localization, and/or prevents degradation of the RNA molecule when incorporated at the 5' end of the RNA molecule. Capped mRNA without 5' end triphosphate structure reduces its immunogenicity side effect. Non-extendable means that the cap analogue will be incorporated only at the 5' terminus because it does not have a 5' triphosphate and therefore cannot be extended in the 3' direction by a template-dependent RNA polymerase.

Cap analogues include, but are not limited to, a chemical structure selected from the group consisting of m7GpppG, m7GpppA, m7GpppC; unmethylated cap analogues (e.g., GpppG); dimethylated cap analogue (e.g., m2,7GpppG), trimethylated cap analogue (e.g., m2,2,7GpppG), dimethylated symmetrical cap analogues (e.g., m7Gpppm7G), or anti reverse cap analogues (e.g., ARCA; m7,2'OmeGpppG, m7,2'dGpppG, m7,3'OmeGpppG, m7,3'dGpppG and their tetraphosphate derivatives) (Stepinski et al., 2001. RNA 7(10):1486-95, the content of which is hereby incorporated by reference by its entirety).

Further cap analogues have been described previously (U.S. Pat. Nos. 7,074,596, 8,304,529, 8,153,773, 8,519,110, 9,295,717, and 9,388,420, the contents of which are hereby incorporated by reference by their entireties). The synthesis of N7-(4-chlorophenoxyethyl) substituted dinucleotide cap analogues has been described recently (Kore et al., 2013. *Bioorg. Med. Chem.* 21(15):4570-4).

Particularly preferred cap analogues may be G[5']ppp[5']G, m$^7$G[5']ppp[5']G, m3$^{2,2,7}$G[5']ppp[5']G, m2$^{7,3'-O}$G[5']ppp[5']G (3'-ARCA), m2$^{7,2'-O}$GpppG (2'-ARCA), m2$^{7,2'-O}$GppspG D1 (p3-S-ARCA D1), m2$^{7,2'-O}$GppspG D2 (p3-S-ARCA D2), m$^7$GpppmAG, m$^7$GpppmAmG, m$^7$GpppmAmGG, m$^7$GpppmA, m$^7$mGpppmA, m$^7$Gpppm$^7$mAG, and m$^7$mGpppm$^7$mAG.

In some embodiments, cap analogues may be Cap 0, Cap 1, or Cap 2 analogues.

In some embodiments, cap analogues may include Cap [I] with the structure of:

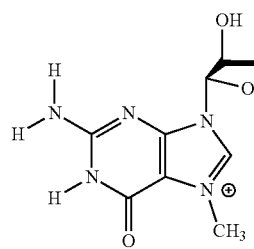 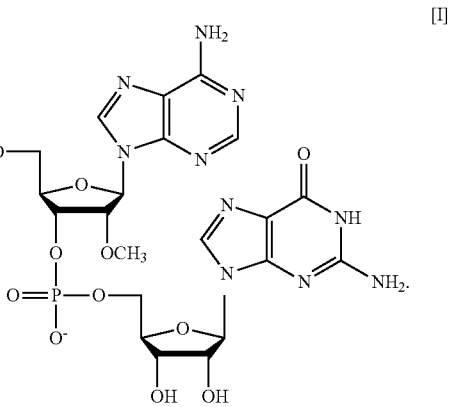

[I]

Preferably, cap analogue may be added with an initial concentration in the range of about 1 to about 20 mM, about 1 to about 17.5 mM, about 1 to about 15 mM, about 1 to about 12.5 mM, about 1 to about 10 mM, about 1 to about 7.5 mM, about 1 to about 5 mM or about 1 to about 2.5 mM. Even more preferred the cap analogue may be added with an initial concentration of about 5 to about 20 mM, about 7.5 to about 20 mM, about 10 to about 20 mM or about 12.5 to about 20 mM. In some embodiments, cap analogue may be in a concentration of from about 0.5 mM to about 50 mM, from about 0.5 mM to about 40 mM, from about 0.5 mM to about 30 mM, from about 0.5 mM to about 20 mM, from about 0.5 mM to about 10 mM, from about 0.5 mM to about 5 mM, from about 1 mM to about 10 mM, from about 2 mM to about 10 mM, from about 3 mM to about 10 mM, from about 3 mM to about 9 mM, from about 3 mM to about 8 mM, from about 3 mM to about 7 mM, from about 3 mM to about 6 mM, from about 3 mM to about 5 mM, from about 3 mM to about 4 mM, from about 4 mM to about 10 mM, from about 5 mM to about 10 mM, from about 6 mM to about 10 mM, from about 6 mM to about 9 mM, from about 6 mM to about 8 mM, from about 6 mM to about 7 mM, from about 7 mM to about 10 mM, from about 8 mM to about 10 mM, or from about 9 mM to about 10 mM.

In some embodiments, cap analogues may be chemically synthesized using known methods, such as, but not limited to phosphorylation, oxidation with amidite and nucleoside as starting material to form a dimer fragment, then followed preparing a GDP imidazolide fragment through chemical synthesis, then a final coupling reaction.

Ribonuclease inhibitor: A ribonuclease inhibitor inhibits the action of a ribonuclease, which degrades RNA. Preferably, the concentration of the ribonuclease inhibitor in the in vitro transcription mixture(s) described herein may be from about 1 to about 500 units/ml, about 1 to about 400 units/ml, about 1 to about 300 units/ml, about 1 to about 200 units/ml, or about 1 to about 100 units/ml. Even more preferred the concentration of the ribonuclease inhibitor may be about 100 to about 300 units/ml, for example, 100 units/ml, 150 units/ml, 200 units/ml, 250 units/ml, or 300 units/ml.

Antioxidant: An antioxidant inhibits the oxidation of other molecules. Suitable antioxidants for use in the present disclosure may include, but are not limited to, DTT (dithiothreitol), TCEP (tris(2-carboxyethyl)phosphine), NAC (N-acetylcysteine), beta-mercaptoethanol, glutathione, cysteine and cystine. Preferably, DTT may be used in in vitro transcription reaction.

The concentration of the antioxidant, preferably of DTT, in the in vitro transcription mixture(s) described herein may be about 1 to about 50 mM, about 5 to about 48 mM, about 8 to about 47 mM, about 10 to about 46 mM, about 15 to about 45 mM, about 18 to about 44 mM, about 20 to about 43 mM, about 23 to about 42 mM, about 25 to about 41 mM or about 28 to about 40 mM. Preferably, the concentration may be about 40 mM.

Amine: Preferably, the amine to be used in the present invention may be betaine (trimethylglycine). The concentration of the amine, preferably of betaine, may be about 10 mM to about 2M, preferably it may be about 0.7 M to about 1.3 M.

Polyamine: Preferably, the polyamine may be selected from the group consisting of spermine and spermidine. Preferably the concentration of the polyamine may be from about 1 to about 25 mM, about 1 to about 20 mM, about 1 to about 15 mM, about 1 to about 10 mM, about 1 to about 5 mM, or about 1 to about 2.5 mM. Even more preferred the concentration of the polyamine may be about 2 mM. Most preferred may be a concentration of about 2 mM of spermidine.

Dnase: Dnases are enzymes which hydrolyze DNA by catalyzing the hydrolytic cleavage of phosphodiester linkages in the DNA backbone. Suitable Dnases may be isolated from bovine pancreas and may be available from various suppliers such as Sigma-Aldrich, New England Biolabs, Qiagen and ThermoFisher. Preferably, Dnase may be free of any RNAse activity. In the method of the present disclosure, treatment with Dnase may be performed after the RNA in vitro transcription reaction by adding Dnase to reaction mixture used for RNA in vitro transcription. Preferably, a suitable amount of calcium chloride may be added together with the Dnase to the RNA in vitro transcription mixture. The suitable amount of CaCl$_2$) may be from about 1 to about 5 mM, preferably from about 2 to about 4 mM and more preferably it may be about 3 mM. DNA may be treated with the Dnase for about 1 to about 5 hours, preferably for about 1.5 to about 3 hours and more preferably for about 2 hours. Dnase treatment may be preferably performed at a temperature of about 37° C. In one embodiment, about 3 mM CaCl$_2$) and about 200 U/ml Dnase I may be added to RNA in vitro transcription mixture and the resulting mixture may be incubated for about two hours at about 37° C. In another embodiment, about 3 mM CaCl$_2$) and about 400 U/ml Dnase I may be added to RNA in vitro transcription mixture and the resulting mixture may be incubated for about two hours at about 37° C. Dnase treatment can be stopped by adding EDTA or another chelating agent. Preferably, Dnase treatment may be stopped by adding EDTA to a final concentration of about 25 mM.

Embodiments of the present disclosure may provide a combined solution for in vitro synthesis of mRNA of different sizes ranging from, for example without limitation, about 1 Kb-20 Kb, such as 1 Kb-15 Kb, or 1 Kb-10 Kb, with high capping efficiency, uniform poly A tail, high yields and integrity in a time efficient manner. Embodiments of the present disclosure may include design of T7 promoter sequence in a DNA template to provide high affinity to cap analogue to transcribe a capped mRNA with T7 RNA polymerase in vitro. This DNA template promoter design may include a T7 Φ6.5 promoter followed by a sequence GG. This design can ensure efficient initiation of transcription to prepare a capped mRNA with high fidelity at 5' end by one step method. 5' end capping of mRNA One of the key factors that determines mRNA translation efficiency may be its 5' end capping. Typically, capping is performed using capping enzymes, and although the efficiency of the capping may be high, the process is time consuming and costly. There is therefore a need for an efficient co-transcriptional method that allows for quicker production of higher efficiency capped mRNA. This need was partially addressed by Ishikawa M., Ishikawa, et al., "Preparation of eukaryotic mRNA having differently methylated adenosine at the 5'-terminus and the effect of the methyl group in translation", *Nucleic Acids Symposium Series*, Volume 53, Issue 1, September-October 2009, pages 129-130. Ishikawa demonstrated the use of trinucleotide cap analogues of m7GpppA*pG structure (wherein A* is adenosine or methylated adenosine derivative) to prepare capped mRNA through one step in vitro transcription. By using these molecules, Ishikawa obtained a reporter 5'capped mRNAs carrying A, A$^m$, $^{m6}$A, or $^{m6}$Am as the first transcribed nucleotide and studied their translational properties in rabbit reticulocyte system. Another study also confirmed the co-transcriptional capping of the mRNA using cap analogue. Sikorski, P. J., et al., 2020, "The identity and methylation status of the first transcribed nucleotide in eukaryotic mRNA 5' cap modulates protein expression in living cells", *Nucleic acids research*, 48(4), pp. 1607-1626. Although these methods show higher efficiency of transcriptional capping, the efficiency of capping was still around 95-96% efficiency, or, depending on the cap molecule, lower efficiency than that. Thus, there is still a need for an efficient co-transcriptional method that would allow for more time- and/or cost-efficient production of higher quality capped mRNA.

In embodiments, methods and/or compositions that increase capping efficiency may be provided. In embodiments, methods and/or compositions that increase the capping efficiency to greater than about 96% efficiency, greater than about 96.5% efficiency, greater than about 97% efficiency, greater than about 97.5% efficiency, greater than about 98% efficiency, greater than about 98.5% efficiency, greater than about 99% efficiency, greater than about 99.5% efficiency may be provided as measured by a method of cutting mRNA with Rnase H, followed with measure the capping efficiency with LC-MS.

Figure 10A:
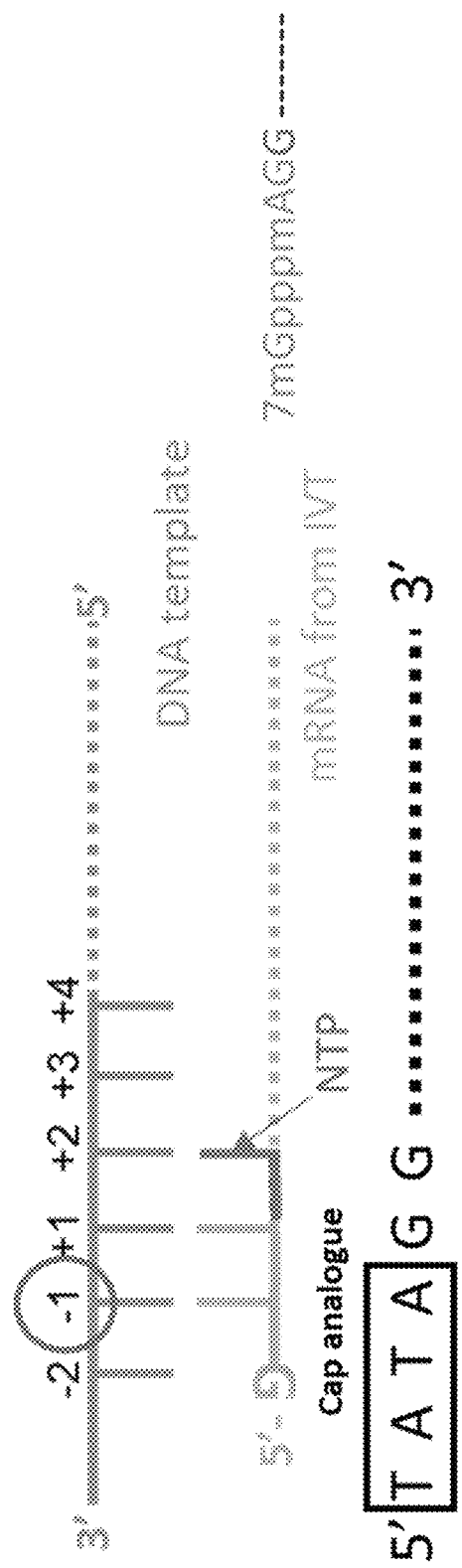
FIG. 10A shows use of cap analogues to initiate in vitro transcription at −1 position in accordance with one embodiment of the present disclosure.

In embodiments, cap analogues can initiate in vitro transcription to synthesize a capped mRNA in one pot reaction. In embodiments, the first base of methyl-A after the inverted G cap may bind to the −1 position of the DNA template, and the second base of G may bind to +1 position of the DNA template, forming a complex with RNA polymerase to recruit the next ribonucleoside triphosphate (NTP) to elongate the RNA during the transcription process. For example, as shown in FIG. 10A, when Cap [I] ($^{m7}$G5pppA$^{2'-Ome}$G), is utilized in the IVT, the first base of methyl-A after inverted G cap binds to −1 position of the DNA template, the second base of G binds to +1 position of the DNA template, forming the complex with T7 RNA polymerase to recruit the next NTP to elongate the RNA during the transcription process.

In embodiments, a composition comprising one or more cap analogue, as described herein, is provided. In embodiments, a method utilizing one or more cap analogue, as described herein, is provided. In embodiments, cap analogues as described herein may be used in conjunction with compositions and/or methods described herein and/or in conjunction with traditional compositions and/or methods. In embodiments, methods and/or compositions described herein may increase mRNA capping efficiency to greater than about 96% efficiency, greater than about 96.5% efficiency, greater than about 97% efficiency, greater than about 97.5% efficiency, greater than about 98% efficiency, greater than about 98.5% efficiency, greater than about 99% efficiency, greater than about 99.5% efficiency, or up to about 100% efficiency.

Promoters

The promoter design in a DNA template may be important for DNA dependent RNA polymerase to initiate in vitro transcription. In embodiments, where a T7 RNA polymerase (a single subunit polymerase derived from the T7 bacteriophage) may be used, the DNA template promoter design may include a T7 Φ6.5 promoter followed with a sequence GG, GA or AGG. In embodiments, this design may enable the highly efficient initiation of transcription to prepare a mRNA with high fidelity at 5'end, by one step method.

In embodiments, the promoters may have a sequence of TAATACGACTCACTATAX$_1$X$_2$X$_3$ (SEQ ID NO: 16), wherein X$_1$ is A or G, X$_2$ is A or G, and X$_3$ is A, T, G, or C.

In embodiments, where a T7 RNA polymerase may be used, at least one promoter sequences in Table 1 may be used to initiate in vitro transcription. The promoters can be added into the plasmid vector through gene synthesis or sub-cloning.

TABLE 1

| SEQ ID NO | Sequence |
|---|---|
| 10 | TAATACGACTCACTATAGGG |
| 11 | TAATACGACTCACTATAGG |
| 12 | TAATACGACTCACTATAAGG |
| 13 | TAATACGACTCACTATAGAT |

TABLE 1-continued

| SEQ ID NO | Sequence |
| --- | --- |
| 14 | TAATACGACTCACTATAGA |
| 15 | TAATACGACTCACTATTAGG |

In embodiments, at least one of SEQ ID NO: 10, SEQ ID NO: 11, SEQ ID NO: 12, SEQ ID NO: 13, SEQ ID NO: 14, or SEQ ID NO: 15 may be used to initiate in vitro transcription.

In embodiments, a composition comprising one or more promoter, as described herein, is provided. In embodiments, a vector comprising one or more promoter, as described herein, is provided. In embodiments, a method utilizing one or more promoter, as described herein, is provided. In embodiments, a compositions comprising mRNA comprising one or more promoter, as described herein, is provided. In embodiments, a vector comprising mRNA comprising one or more promoter, as described herein, is provided. In embodiments, a method utilizing mRNA comprising one or more promoter, as described herein, is provided.

In some embodiments, in vitro transcription may start at −1 position, which may help to form a more favorable complex with T7 RNA polymerase and in turn to produce more full length RNAs. Application of using −1 and +1 position of starting site for in vitro transcription allows for more flexibility on the choice of first mRNA base (not including cap base) and leave +2 position open for custom sequence as described in Table 1 for mRNA production. Current general practice for incorporating cap molecule during in vitro transcription uses +1 position for initiation of the mRNA synthesis, which requires the template has the exact sequence of AG or AT following T7 promoter sequence of TATA box. Embodiments of the present disclosure may include a method of using DNA template with regular T7 promoter sequences, which has GG following TATA box of T7 promoter, which does not require specific mutagenesis on DNA template for preparing Cap1 mRNA co-transcriptionally.

In some embodiment, a method for in vitro transcription of a DNA template into RNA, may include providing (1) a DNA template comprises a promoter operably linked to a nucleic acid containing a 5' untranslated region (5' UTR), an open reading frame (ORF) encoding the RNA of interest, a 3' UTR, and a poly A region, and (2) a cap analogue containing the structure of

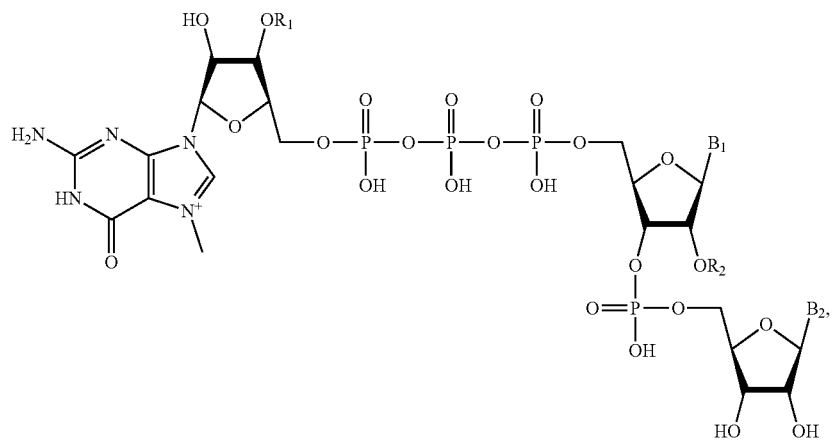

in which $R_1$ and $R_2$ may be each $CH_3$ or H; and $B_1$ and $B_2$ may be each A, U, G, or C, in which the promoter may contain a sequence of TAATACGACTCACTATAX$_1$X$_2$X$_3$ (SEQ ID NO: 16), in which A at position 17 is −1 nucleotide and X$_1$ at position 18 is +1 nucleotide, when $X_1$ is G, $X_2$ and $X_3$ are each A, T, G, or C, then $B_1$ is A and $B_2$ is G, when $X_1$ is A, $X_2$ and $X_3$ are each A, T, G, or C, then $B_1$ is A and $B_2$ is A, when $X_1$ is C, $X_2$ and $X_3$ are each A, T, G, or C, then $B_1$ is A and $B_2$ is C, and when $X_1$ is T, $X_2$ and $X_3$ are each A, T, G, or C, then $B_1$ is A and $B_2$ is U, in which the cap analogue binds to −1 and +1 nucleotides of the promoter, and incubating the DNA template and the cap analogue in a reaction mixture, in which the incubating may include incubating the reaction mixture at from about 15° C. to about 35° C. for from about 1 hour to about 12 hours, thereby producing the RNA.

The promoter may contain a sequence selected from SEQ ID NO: 10, 11, 13, and 14.

In some embodiment, a method for in vitro transcription of a DNA template into RNA, may include providing (1) a DNA template comprises a promoter operably linked to a nucleic acid containing a 5' untranslated region (5' UTR), an open reading frame (ORF) encoding the RNA of interest, a 3' UTR, and a poly A region, and (2) a cap analogue, in which the cap analogue binds to −1 and +1 nucleotides of the promoter, and incubating the DNA template and the cap analogue in a reaction mixture, in which the incubating may include incubating the reaction mixture at from about 15° C. to about 35° C., preferably from about 18° C. to about 31° C., for an appropriate time preferably from about 1 hour to about 12 hours, thereby producing the RNA.

In some embodiment, a method for in vitro transcription of a DNA template into RNA, may include providing (1) a DNA template comprises a promoter operably linked to a nucleic acid containing a 5' untranslated region (5' UTR), an open reading frame (ORF) encoding the RNA of interest, a 3' UTR, and a poly A region, and (2) a cap analogue, in which the cap analogue binds to −1 and +1 nucleotides of the promoter, and incubating the DNA template and the cap analogue in a reaction mixture, thereby producing the RNA.

In some embodiment, the reaction mixture comprises NTPs and an RNA polymerase. In some embodiment, the reaction mixture may further comprise one or more of the following: a buffer substance, an Rnase inhibitor, a magnesium salt, a polyamine, and a pyrophosphatase.

In some embodiment, the reaction mixture comprises: a buffer substance in a concentration of from about 45 mM to about 55 mM, an Rnase inhibitor in a concentration of from about 0.01 U/µl to about 0.03 U/µl, NTPs in a concentration of from about 3 mM to about 5 mM, the cap analogue in a concentration of from about 6 mM to about 8 mM, one or more magnesium salts in a concentration of from about 20 mM to about 30 mM, a polyamine in a concentration of from about 1.5 mM to about 2.5 mM, the DNA template in a concentration of from about 0.01 µg/µl to about 0.05 µg/µl, a pyrophosphatase in a concentration of from about 0.1 mU/µl to about 0.5 mU/µl, and an RNA polymerase in a concentration of from about 0.01 µg/µl to about 0.05 µg/µl.

5' UTRs and 3' UTRs mRNA molecule may be flanked with 5' end and 3' end untranslated regions (UTR). 5'-UTR may be recognized by ribosome to allow for initiation of translation, and 3'UTR may contain regulatory sequences that can influence the expression and half-life of the mRNA. Several different combinations of 5' and 3' UTR can enable high expression efficiency of mRNA when expressed in mammalian cells.

Cao, et al. (Cao, et al., "High-throughput 5'UTR engineering for enhanced protein production in non-viral gene therapies", *Nature Communications*, (2021) 12:4138, pages 1-10, incorporated herein by reference in its entirety) has reported a method of generating artificial 5'UTRs through a high-throughput screening process.

In embodiments, the combination of artificial selected 5' UTR, and human hemoglobin or mouse hemoglobin 3' UTR can be used to generate a construct for highly efficient expressing mRNA sequences. The combination thereof may be selected and used to construct a vector for in vitro transcription (IVT). That may be used to generate mRNA with highly efficient protein expression capability. In embodiments, one or more UTR set forth in Table 5 (see below, in Example 1) is used. In embodiments, one or more UTR set forth in Table 5 may be used in any combination. In embodiments, the UTRs may be used in pairs, as set forth in Table 5, with the members of pairs being in the same row. In embodiments, SEQ ID NO. 1 is paired with SEQ ID NO. 2, SEQ ID NO. 3 is paired with SEQ ID NO. 2, SEQ ID NO. 1 is paired with SEQ ID NO. 4, SEQ ID NO. 1 is paired with SEQ ID NO. 6, SEQ ID NO. 3 is paired with SEQ ID NO. 6, and/or SEQ ID NO. 9 is paired with SEQ ID NO. 2. In embodiments, use of one or more of the UTRs set forth in Table 5 may enable high expression efficiency of mRNA when expressed in mammalian cells. In embodiments, use of one or more pairs of the UTRs set forth in Table 5 may enable high expression efficiency of mRNA when expressed in mammalian cells.

In embodiments, the T7 promoter sequences, UTRs may be added to the open reading frame coding sequences through gene synthesis, which may be then sub-cloned into the plasmid vector to generate large scale plasmid DNA for in vitro transcription application. A composition comprising one or more UTR, as described herein, is provided. In embodiments, a vector comprising one or more UTR, as described herein, is provided. In embodiments, a method utilizing one or more UTR, as described herein, is provided. In embodiments, a compositions comprising mRNA comprising one or more UTR, as described herein, is provided. In embodiments, a vector comprising mRNA comprising one or more UTR, as described herein, is provided. In embodiments, a method utilizing mRNA comprising one or more UTR, as described herein, is provided.

Poly A Tails

Poly-A tail quality (such as length and uniformity of length and distribution) may directly impact mRNA expression efficiency. Traditional methods for adding poly A tail to a mRNA product in vitro use poly A polymerase. See, e.g., Cao, G. J. and Sarkar, N., "Identification of the gene for an *Escherichia coli* poly(A) polymerase", *Proc. Natl. Acad. Sci. USA*, (1992) 89(21), 10380-10384, incorporated herein by reference in its entirety. However, such methods usually generate a product with a broad distribution of poly A tail lengths, with only about 70% of mRNA being tailed.

In addition to capping and poly-A tail length and distribution, mRNA purity and integrity may be important factors that influence the properties of mRNA, such as, but not limited to, its stability and/or expression efficiency. Purification, promoter sequence, 5' and/or 3' UTR sequence(s), and/or transcription conditions may contribute to generating a high quality mRNA.

A traditional method for adding poly A tail to a mRNA product in vitro uses poly A polymerase as described in, for example, Cao et al. (*Proc. Natl. Acad. Sci. USA*. 89, 10380-10384). But this method may generate poly A products with broad distribution of poly A tail length, e.g., with only about 70% of mRNA polyadenylated. Embodiments of the present disclosure include methods of efficiently adding poly A tail via Polymerase Chain Reaction (PCR) to the DNA template, thus, to generate more uniformly poly A tailed products for efficient mRNA expression, it will provide benefit of engineering the template tail design by single step PCR reaction rather than going through traditional lengthy cloning and plasmid purification steps. Embodiments of the present disclosure may also provide for longer poly-A tails than provided by some traditional methods.

In embodiments, methods and/or compositions may include provision of capped analogues, methods of providing and/or improving length and/or distribution of poly-A tails, provision of effective promoters, provision of effective UTRs, such as pairs of UTRs, provision of effective transcription conditions, provision of an effective transcription system, provision of effective purification, or any combination thereof.

In embodiments, methods and/or compositions that increase the uniformity of length and/or distribution of poly-A tails among the transcribed mRNA molecules may be provided. In embodiments, methods and/or compositions may produce a population of mRNAs wherein greater than about 70% are tailed, wherein at least about 71% are tailed, wherein at least about 72% are tailed, wherein at least about 73% are tailed, wherein at least about 74% are tailed, wherein at least about 75% are tailed, wherein at least about 76% are tailed, wherein at least about 77% are tailed, wherein at least about 78% are tailed, wherein at least about 79% are tailed, wherein at least about 80% are tailed, wherein at least about 85% are tailed, wherein at least about 90% are tailed, wherein at least about 95% are tailed, wherein at least about 99% are tailed.

In embodiments, methods and/or compositions may produce a population of mRNAs wherein the lengths (the number of adenines) of the poly-A tails vary by at most about 70 to about 130 adenines between the mRNA molecules, by at most about 60 to about 120 adenines between the mRNA molecules, by at most about 50 to about 100 adenines between the mRNA molecules, by at most about 40 to about 90 adenines between the mRNA molecules, by at most about 50 to about 80 adenines between the mRNA molecules, by at most about 40 to about 70 adenines between the mRNA molecules, by at most about 30 to about 50 adenines between the mRNA molecules, or by at most about 20 to about 40 adenines between the mRNA molecules. The poly A tail length of mRNA may be measured by a method to digest the mRNA with Rnase T1, followed by purifying and recovering the poly A fragment with oligo-dT magnetic beads, and then test the poly A fragment length by Bioanalyzer capillary gel electrophoresis.

In embodiments, a poly-A tail is added to a DNA template before transcription. In embodiments, a method of adding a poly-A tail to a DNA template prior to transcription may be provided. In embodiments, a poly-A tail is added to a DNA template via Polymerase Chain Reaction (PCR), which is a new way of adding poly A tail comparing to traditional method by gene synthesis to insert into the plasmid vector. In embodiments, addition of a poly-A tail to the DNA template may result in the generation of a more uniformly poly-A-tailed mRNA product, a product with longer poly-A tails, or both, each or both of which may result in more efficient mRNA expression.

In embodiments, a composition comprising mRNA comprising a poly-A tail added by PCR, as described herein, is provided. In embodiments, a vector comprising a poly-A tail added to the vector by PCR, as described herein, is provided. In embodiments, a pVAX1 or pUC57 vector comprising ampicillin resistant gene, T7 promoter sequences, 5' UTR and 3' UTR sequences, mRNA comprising a poly-A tail (e.g., 100A) added by PCR, as described herein, is provided. In embodiments, a method utilizing mRNA comprising a poly-A tail added by PCR, as described herein, is provided.

In embodiments, disclosed methods and/or compositions may produce a population of mRNAs wherein greater than about 70% are tailed, wherein at least about 71% are tailed, wherein at least about 72% are tailed, wherein at least about 73% are tailed, wherein at least about 74% are tailed, wherein at least about 75% are tailed, wherein at least about 76% are tailed, wherein at least about 77% are tailed, wherein at least about 78% are tailed, wherein at least about 79% are tailed, wherein at least about 80% are tailed, wherein at least about 85% are tailed, wherein at least about 90% are tailed, wherein at least about 95% are tailed, wherein at least about 99% are tailed, wherein about 100% are tailed.

In embodiments, disclosed methods and/or compositions may produce a population of mRNAs wherein the lengths (the number of adenines) of the poly-A tails vary by at most about 70 to about 130 adenines between the mRNA molecules, by at most about 60 to about 120 adenines between the mRNA molecules, by at most about 50 to about 100 adenines between the mRNA molecules, by at most about 40 to about 90 adenines between the mRNA molecules, by at most about 50 to about 80 adenines between the mRNA molecules, by at most about 40 to about 70 adenines between the mRNA molecules, by at most about 30 to about 50 adenines between the mRNA molecules, or by at most about 20 to about 40 adenines between the mRNA molecules.

Bacterial studies have demonstrated that the sequence of repeats, e.g., CTG.CAG, as well as the mode and level of plasmid replication and transcription may play a role in expansion and deletion of repeats. The frequency of deletion of cloned repeats may increase up to 20-fold upon induction of the lacZ promoter, which drives transcription of inserts in pUC19 (Bowater et al., 1997. Transcription increases the deletion frequency of long CTG-CAG triplet repeats from plasmids in *Escherichia coli. Nucleic Acids Res* 25: 2861-2868; the content of which is hereby incorporated by reference in its entirety). Common vectors may be typically maintained at high copy number and may induce transcription and translation of antibiotic resistance gene, indicator gene (such as blue/white screening gene) and inserted fragments, causing instability of certain classes of DNA sequences. As an extreme repeat and extremely low GC ratio sequence, polyA sequences may be easily lost in the process of plasmid cloning and replication. If such a sequence occurs, unexpected transcription and translation affected by the inductive activity of upstream and downstream promoters may further increase instability of polyA sequences. In order to avoid the initiation activity of similar promoters in vectors for the inserted sequence, common strategies may include segmenting the inserted gene (if the inserted gene is significantly cytotoxic) or directional cloning of the ORF in the "reverse" orientation relative to transcription from the vector's promoter. However, these two strategies may be not suitable for gene cloning that contain polyA sequences. Segmentation can eliminate the genotoxicity of cloned genes after being expressed, but this strategy may not solve the problem of instability of polyA sequences because the process of transcription has not been eliminated, while the reverse insertion can only eliminate the influence of the promoter in a certain direction. Therefore, embodiments of the present disclosure may include modifying vectors by inserting transcriptional terminators at the upstream and downstream of the multiple cloning site, which can effectively interrupt the influence of the upstream and downstream promoters of the multiple cloning site on the inserted gene. This strategy effectively improves the stability of polyA sequences in the process of plasmid cloning and replication, especially for some extremely unstable polyA-containing cassette. The results show that, after adding transcriptional terminators to the upstream and downstream of the multiple cloning site, the positive rate of clones reached 25%-50% (almost 0 before adding terminator), and the number of A bases of polyA tails increased from 70-110 to about 120. In addition, after adding terminators upstream and downstream of the inserted cassette, the yield of plasmid also increased by 32.5%. Without being limited to a particular theory, this increase may be due to the insertion of a transcriptional terminator restores the activity of the origin of replication (Stueber et al., 1982. Transcription from efficient promoters can interfere with plasmid replication and diminish expression of plasmid specified genes. *EMBO J* 1: 1399-1404; the content of which is hereby incorporated by reference in its entirety). Using transcriptional terminators at the upstream and downstream of the multiple cloning site to facilitate the cloning of cytotoxic sequences or sequences of repeats, such as PolyA tails, has not been reported in the art.

A transcriptional termination sequence may be any nucleotide sequence, which when placed transcriptionally downstream of a nucleotide sequence encoding an open reading frame, causes the end of transcription of the open reading frame. Such sequences are known in the art and may be of prokaryotic, eukaryotic or phage origin. Examples of terminator sequences include, but are not limited to, PTH-terminator, pET-T7 terminator, T3-Tφ terminator, pBR322-P4 terminator, vesicular stomatitis virus terminator, rrnB-T1 terminator, rrnB-T2 terminator, lambda t0 terminator, rrnC terminator, Ttadc transcriptional terminator, and yeast-recognized termination sequences, such as Matα (α-factor) transcription terminator, native α-factor transcription termination sequence, ADR1 transcription termination sequence, ADH2 transcription termination sequence, and GAPD transcription termination sequence. A non-exhaustive listing of transcriptional terminator sequences may be found in the iGEM registry, which is available at: partsregistry.org/Terminators/Catalog. The first transcriptional terminator sequence of a series of 2, 3, 4, 5, 6, 7, or more may be placed directly 3' to the final nucleotide of a gene of interest (or open reading frame) or at a distance of at least 1-5, 5-10, 10-15, 15-20, 20-25, 25-30, 30-35, 35-40, 40-45, 45-50, 50-100, 100-150, 150-200, 200-300, 300-400, 400-500, 500-1,000 or more nucleotides 3' to the final nucleotide of a gene of interest (or open reading frame). The number of nucleotides between tandem transcriptional terminator sequences may be varied, for example, transcriptional terminator sequences may be separated by 0, 1, 2, 3, 4, 5, 6, 7, 8, 9, 10, 10-15, 15-20, 20-25, 25-30, 30-35, 35-40, 40-45, 45-50 or more nucleotides.

Vectors

In embodiments, a vector including one or more of (i) a poly-A tail, as described herein, (ii) one or more UTR, as described herein, (iii) one or more promoter, as described herein, or (iv) combinations thereof, is provided. In embodiments, the vector may have various uses, including, but not limited to, use for insertion of a target template nucleotide sequence. In embodiments, such a vector with a target template nucleotide sequence may be used for, as non-limiting examples, cloning or transcribing the target template nucleotide sequence. In embodiments, transcription may include in vitro transcription. In embodiments, transcription may be carried out using a T7 RNA polymerase. In embodiments, a vector may be a plasmid or a viral vector, for example but without limitation, pVAX1 and/or pUC57.

mRNA purity

The integrity of mRNA may affect cellular expression; therefore it may be important to begin translation with high integrity mRNA. The conditions used for transcription may affect the quality of mRNA produced. Some transcription conditions can lead to higher truncated products.

The integrity of the mRNA may be one of the critical factors that affects cellular expression, therefore it may be paramount to begin with high integrity mRNA. There are two aspects to the mRNA integrity. Typically, RNA is prone to quicker degradation than DNA due its chemical instability, therefore the storage conditions impact the quality of the RNA. Additionally, transcription conditions can also lead to higher truncated products and therefore the optimal buffer conditions can be determined empirically to have higher integrity over a wide range of mRNA sizes and also have higher yields.

Conditions used for purification may affect the quality of mRNA produced. For example, Trinucleotide cap analogues of $^{m7}$GpppA*pG residues in the finished mRNA product could compete with capped mRNA for recruiting ribosome, thus inhibiting the mRNA translation efficiency in cells. Purification after in vitro transcription may be an important step in acquiring final purified mRNA product.

The present disclosure further provides a solution to obtain pure mRNA product with minimum contaminant cap analogues, free NTPs, and other proteins, which could interfere and compromise the mRNA product's performance. mRNA purity refers to full length mRNA species ratio in the crude transcribed mRNA product, which may be quantified by the full length peak ratio in capillary gel electrophoresis.

In embodiments, purification as described herein may produce highly pure mRNA product with minimum contaminant analogues, free NTPs, and/or other proteins which could interfere with and/or compromise the mRNA product's stability and/or translation efficiency. In embodiments, a purification method includes using a silica membrane column to bind nucleic acid, then washing with about 60% to about 80% ethanol in water, preferably about 70% to about 80% ethanol in water, followed by elution in water.

Other conventional purification methods with LiCl precipitation, or affinity based magnetic beads purification can be applied for the same purpose. In embodiments, the purification methods as described herein may be used in conjunction with compositions and/or methods described herein and/or in conjunction with traditional compositions and/or methods.

In embodiments, methods and/or compositions that increase purity of transcribed mRNA may be provided. In embodiments, methods and/or compositions that result in obtained mRNA with about 79% or greater purity; mRNA with about 79.5% or greater purity; mRNA with about 80% or greater purity; mRNA with about 80.5% or greater purity; mRNA with about 81% or greater purity; mRNA with about 81.5% or greater purity; mRNA with about 82% or greater purity; mRNA with about 82.5% or greater purity; mRNA with about 83% or greater purity; mRNA with about 83.5% or greater purity; mRNA with about 84% or greater purity; mRNA with about 84.5% or greater purity; mRNA with about 85% or greater purity; mRNA with about 85.5% or greater purity; mRNA with about 86% or greater purity; mRNA with about 86.5% or greater purity; mRNA with about 87% or greater purity; mRNA with about 87.5% or greater purity; mRNA with about 88% or greater purity; mRNA with about 88.5% or greater purity; mRNA with about 89% or greater purity; mRNA with about 89.5% or greater purity; mRNA with about 90% or greater purity; mRNA with about 91% or greater purity; mRNA with about 92% or greater purity; mRNA with about 93% or greater purity; mRNA with about 94% or greater purity; mRNA with about 95% or greater purity; mRNA with about 96% or greater purity; mRNA with about 97% or greater purity; mRNA with about 98% or greater purity; mRNA with about 99% or greater purity; or mRNA with about 100% purity may be provided. The mRNA purity may be measured by capillary gel electrophoresis using Bio analyzer equipment, the target peak area ratio (target length±15%) may be calculated for its purity measurement.

Figure 11A:
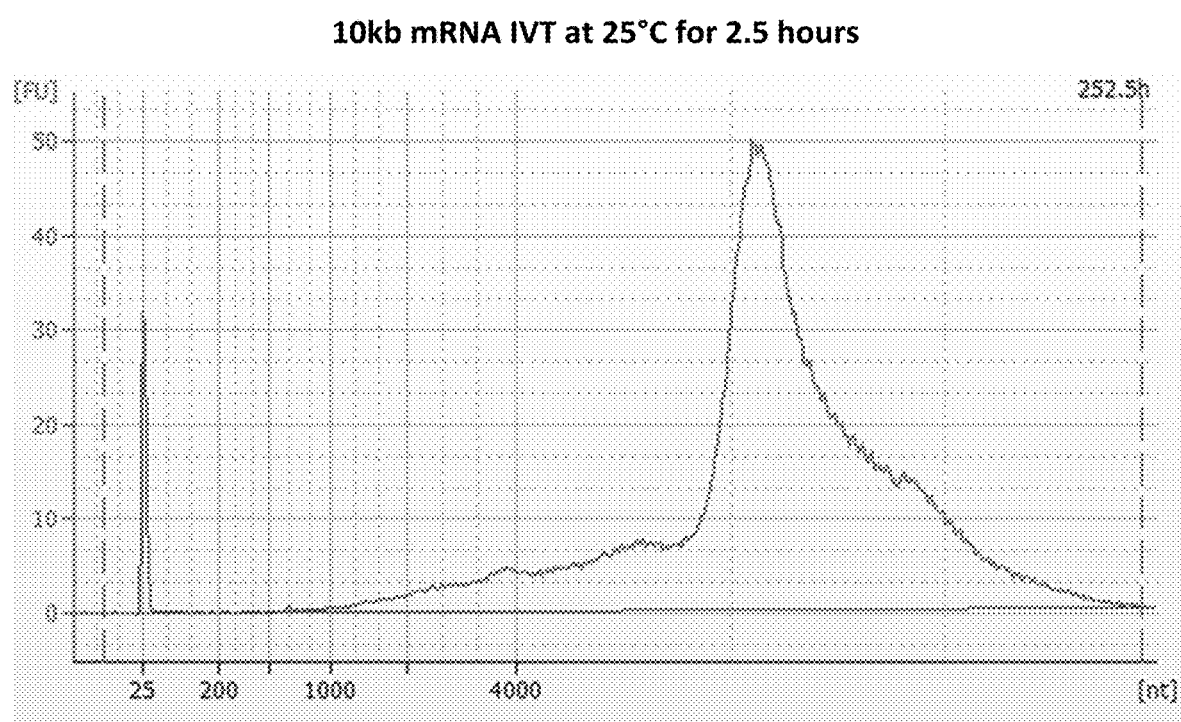
FIG. 11A shows purity of 10 kb mRNA prepared by the methods in accordance with one embodiment of the present disclosure.
Figure 11B:
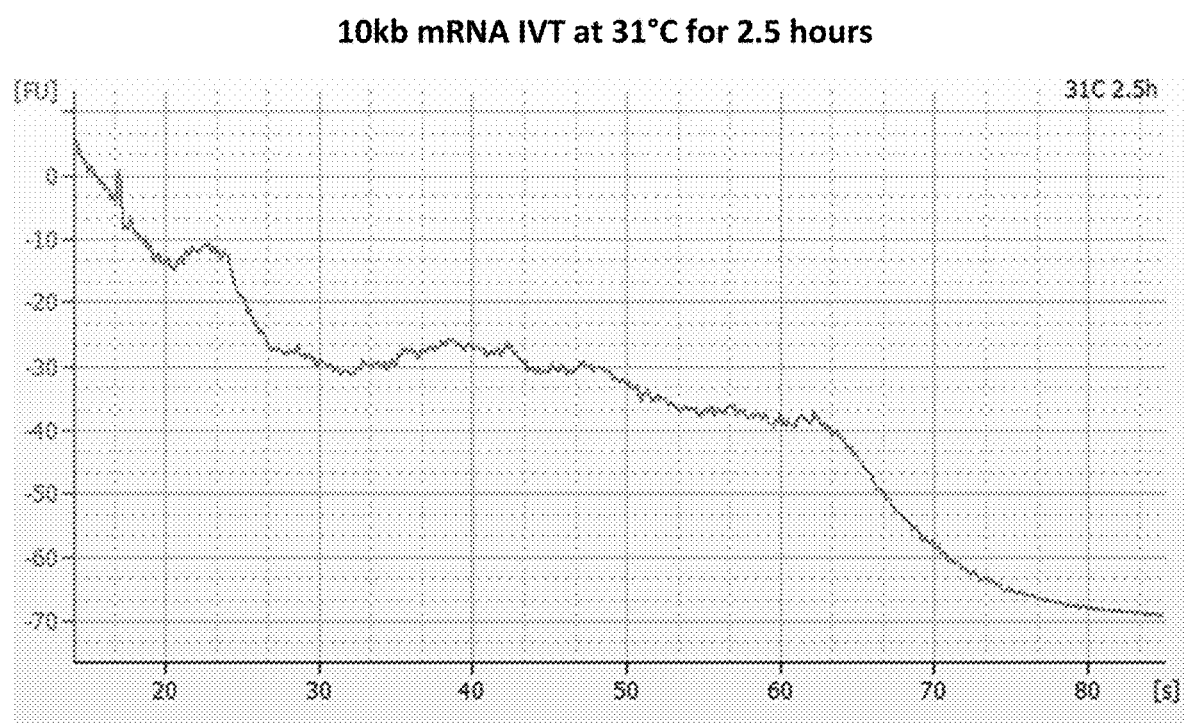
FIG. 11B shows purity of 10 kb mRNA prepared by the methods in accordance with another embodiment of the present disclosure.
Figure 11C:
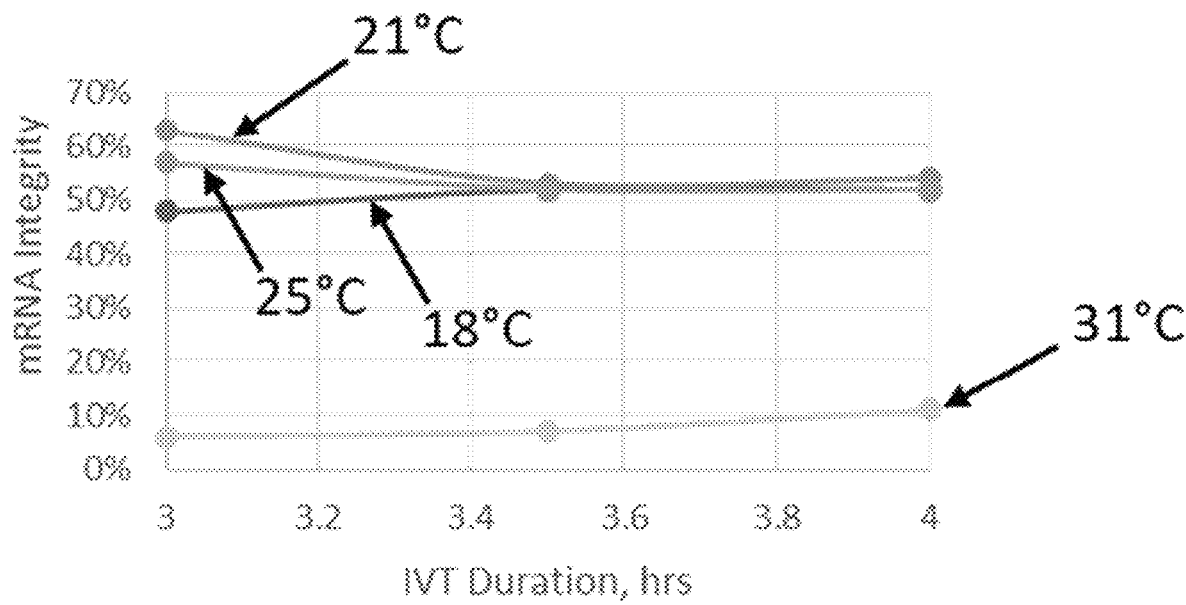
FIG. 11C shows integrity of 10 kb mRNA prepared by the methods in accordance with one embodiment of the present disclosure.
Figure 11D:
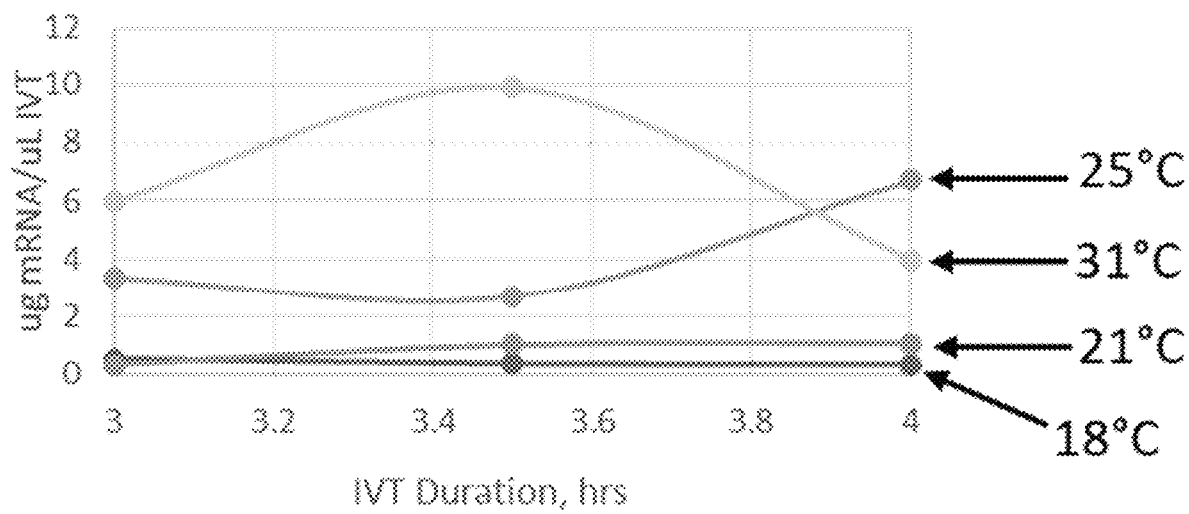
FIG. 11D shows yield of 10 kb mRNA prepared by the methods in accordance with one embodiment of the present disclosure.

In embodiments, methods and/or compositions that increase the purity or integrity of transcribed mRNA may be provided. Obtaining high quality long mRNA from in vitro transcription is a great challenge since long mRNAs tends to degrade more easily. This invention found that temperature and in vitro transcription reaction duration are key factors affecting produced long mRNA quality. As shown from FIG. 11A, in vitro transcription performed at 25° C. for 2.5 hrs resulted in a 10 kb mRNA product of purity around 57% as determined by bioanalyzer, while the same IVT reaction performed at 31° C. for 2.5 hrs resulted in a 10 kb mRNA of purity around 2% since a majority of mRNA products were truncated (FIG. 11B). The yield and purity of mRNA produced by IVT reaction performed at temperatures 18° C., 21° C., 25° C., and 31° C. were studies and the purity and the yield of mRNA results are shown in FIG. 11C and FIG. 11D, respectively. As low as 18° C., long mRNA can be transcribed with T7 polymerase using the disclosed methods.

T7 RNA Polymerase-Mediated Transcription

In eukaryotes, transcription of messenger RNAs (mRNAs) is done by RNA polymerase II. This is a complicated multi-subunit enzyme with complex regulation. To carry out large scale transcription in vitro, researchers commonly use single subunit phage polymerases derived from T7, T3, SP6, K1-5, K1E, K1F or K11 bacteriophages. This family of polymerases uses simple, minimal promoter sequences of ~17 nucleotides, which may not require accessory proteins and may have minimal constraints of the initiating nucleotide sequence. While this application focuses on T7 RNA Polymerase (T7 RNAP), one skilled in the art would understand that the present disclosure may be practiced with other RNA polymerases.

T7 RNA polymerase (RNAP) exists in at least two protein states. The first is referred to as the "abortive complex" and may be associated with transcriptional initiation. The second is a very processive conformation called the "elongation complex." In vitro transcription can be broken into six steps: 1) binding of RNA polymerase to promoter sequence, 2) initiation of transcription, 3) non-processive elongation termed abortive transcription, during which polymerase frequently releases DNA template and short abortive transcripts, 4) conversion of open complex to closed complex, 5) processive elongation, and 6) transcriptional termination. Significant amount of RNA produced during transcription may contain short abortive fragments of ~2-8 nucleotides in length (*Biochemistry* 19:3245-3253 (1980); *Nucleic Acids Res.* 9:31-45 (1981); *Nucleic Acids Res.* 15:8783-8798 (1987); *Biochemistry* 27:3966-3974 (1988), each of which is incorporated herein by reference in its entirety). After synthesis of about 10-14 bases, RNA polymerases may escape from abortive cycling, at the same time losing sequence-specific contacts with promoter DNA, and forming a processive elongation complex, in which RNA chain may be extended in a sequence-independent manner (*J. Mol. Biol.* 183:165-177(1985); *Proc. Natl. Acad. Sci. U.S.A.* 83:3614-3618(1986); *Mol. Cell Biol.* 7:3371-3379 (1987), each of which is incorporated herein by reference in its entirety).

promoters in the T7 genome can initiate with pppGpG (*J. Mol. Biol.* 370:256-268 (2007), incorporated by reference herein in its entirety). It has been shown that T7 RNAP can initiate from dinucleotide primers (*Biochemistry* 24:5716-5723 (1985), incorporated by reference herein in its entirety). Axelrod et al. showed that an uncapped GpA dinucleotide could initiate from +1 and +2 template nucleotides that were 2'-deoxycytidine and 2'-deoxythymidine, respectively ("CT" template). Their reaction conditions were 200 micromolar (µM) dimer and 100 µM ATP, CTP, GTP and UTP. Their reaction mixture also contained 100 µM 3' dATP, 3' dCTP 3' dUTP or 50 µM 3' dGTP. They observed only GpA initiated RNAs and not a mixture of GpA initiated RNAs and 5' triphosphate RNAs from GTP initiation. This is likely due to the reaction conditions employed. 100 µM GTP is well below the 2 mM Kd of T7 polymerase for the first initiating guanosine (*J. Mol. Biol.* (2007) 370, 256-268, incorporated by reference herein in its entirety). Since GTP competes for initiation with the initiating oligonucleotide, using a low GTP concentration favours GpA initiation but may result in low transcription yield (maximum calculated yield estimated to be <150 ug/mL of reaction). When initiating transcription on "CT" template with ApG, CpG, UpG or GpG, they observed formation of RNA transcripts with an additional untemplated 5' nucleotide (A, C, U or G, respectively).

Ishikawa et al. showed that capped initiating oligonucleotide trimers of the structure $^{m7}$GpppApG, $^{m7}$Gppp$^{m6}$ApG, $^{m7}$GpppA$_{2'Ome}$pG or $^{m7}$Gppp$^{m6}$A$_{2'Ome}$pG could initiate transcription on template with 2'-deoxycytidine residues at template positions +1 and +2 ("CC" template; *Nucleic Acids Symposium Series* No. 53: 129 (2009), incorporated by reference herein in its entirety). The authors state, "The different result from the case of using $^{m7}$G5'pppG may be

TABLE 2

```
Position in transcript              +1+2+3+4+5+6
                                     | | | | | |
Transcript sequence                 pppGGGAGA
                                         ↱
Promoter top strand     5'-TAATACGACTCACTATAGGGAGA ... -3'    SEQ. ID. NO: 21
Promoter bottom strand  3'-ATTATGCTGAGTGATATCCCTCT ... -5'    SEQ. ID. NO: 22
                                         ||||||
Position in template                +1+2+3+4+5+6
```

The consensus sequence for the most active Class III T7 promoters may encompass 17 bp of sequence upstream, and 6 bp downstream, of the transcription start site (*Cell* 16:815-25. (1979), incorporated by reference herein in its entirety). The position of the first transcribed nucleotide is commonly referred to as the +1 transcript nucleotide of the RNA, the second transcribed nucleotide as +2 transcript nucleotide and so on (Table 2). During transcription, two strands may be melted to form transcription bubble and the bottom strand of the duplex (shown 3' to 5' in Table 2) is the template for transcription. For transcript nucleotides +3 and beyond, the template strand may define the identity of the transcribed nucleotides primarily through Watson-Crick base pairing interactions. Here, the nucleotide encoding the first RNA transcript nucleotide is defined as the +1 nucleotide of the template. In the example shown in Table 2, the +1 transcript nucleotide is G and the +1 template nucleotide is C. Likewise the +4 transcript nucleotide is A and the +4 template nucleotide is T.

It is known that T7 RNAP can also initiate with short oligonucleotide primers. For example, it is known that 13 caused from base pairing between additional adenosine (N1) in $^{m7}$G5'pppN1 pG and 2'-deoxythymidine in T7 promoter at −1 position." This method clearly differs from the method described in the present disclosure where the +1 and +2 nucleotides of the initiating capped oligonucleotide trimer pair with the +1 and +2 of the template nucleotides. Ishikawa et al. used 6 mM initiating oligonucleotide trimer, 0.9 mM GTP and 7.5 mM each of ATP, CTP and UTP. The authors used a greater than 6 fold excess of the capped initiating oligonucleotide primer, the most expensive nucleotide component of transcription reaction, over competing GTP to drive the transcription reaction toward capped RNA over pppRNA, which increases the total cost of synthesized RNA. On the other hand, a low concentration of GTP (0.9 mM) limits the total yield of the RNA in transcription reaction (theoretically to less than 1.4 mg/mL). On the contrary the method described herein may not require restricting the concentration of any NTP to achieve both an efficient RNA capping and a higher yield of RNA (about 2 to 10 mg/mL) and thus allowing a production of high quality mRNA at a commercially useful cost.

T7 RNA Polymerases

In some embodiments, at least one modification of the T7 RNA polymerase may be selected from the group consisting of P266L, P270L, P270S, P270A, P270Y, Q744L, Q744P, Q744R, Y639F, H784A, E593G, Y639V, V685A, H784G, S430P, N433T, S633P, F849I and F880Y. In some embodiments, at least one modification includes Y639F and H784A. In some embodiments, at least one modification includes E593G, Y639V, V685A and H784G. In some embodiments, at least one modification includes S430P, N433T, S633P, F849I and F880Y. In some embodiments, at least one modification includes S430P, N433T, S633P, F849I, F880Y and P266L. In some embodiments, at least one modification includes S430P, N433T, S633P, F849I, F880Y, Y639F and H784A. In some embodiments, at least one modification includes S430P, N433T, S633P, F849I, F880Y, P266L, Y639F and H784A. In some embodiments, at least one modification includes S430P, N433T, S633P, F849I, F880Y, E593G, Y639V, V685A and H784G. In some embodiments, at least one modification includes S430P, N433T, S633P, F849I, F880Y, P266L, E593G, Y639V, V685A and H784G.

In some embodiments, at least one modification of the T7 RNA polymerase facilitates initiation-elongation transition. In some embodiments, at least one modification increases promoter clearance. In some embodiments, at least one modification increases stability and/or activity of the polymerase. In some embodiments, at least one modification at least one modification increases thermos stability of the polymerase. In some embodiments, at least one modification results in 2'-Ome incorporation.

Magnesium Ions in In Vitro Transcription

Figure 12A:
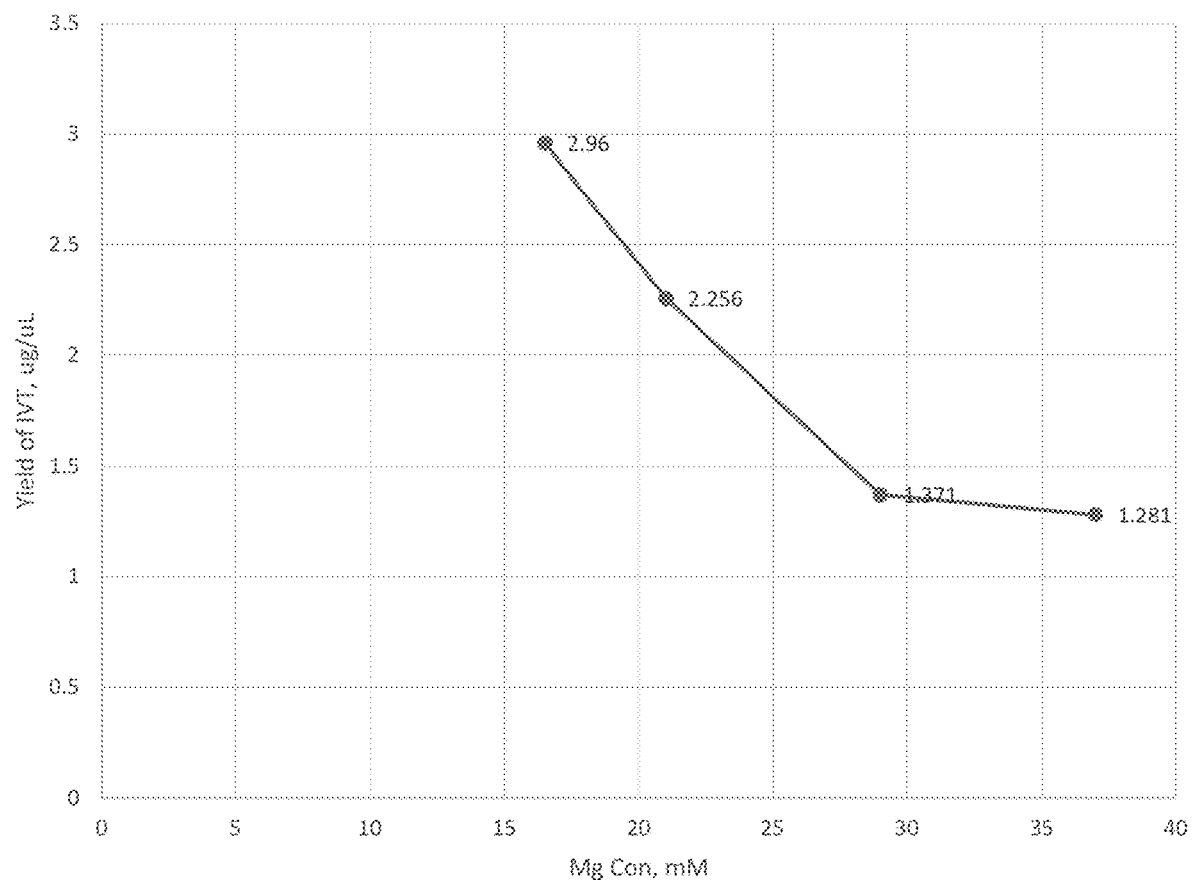
FIG. 12A shows the effect of magnesium on 1 kb mRNA yield in accordance with one embodiment of the present disclosure.
Figure 12B:
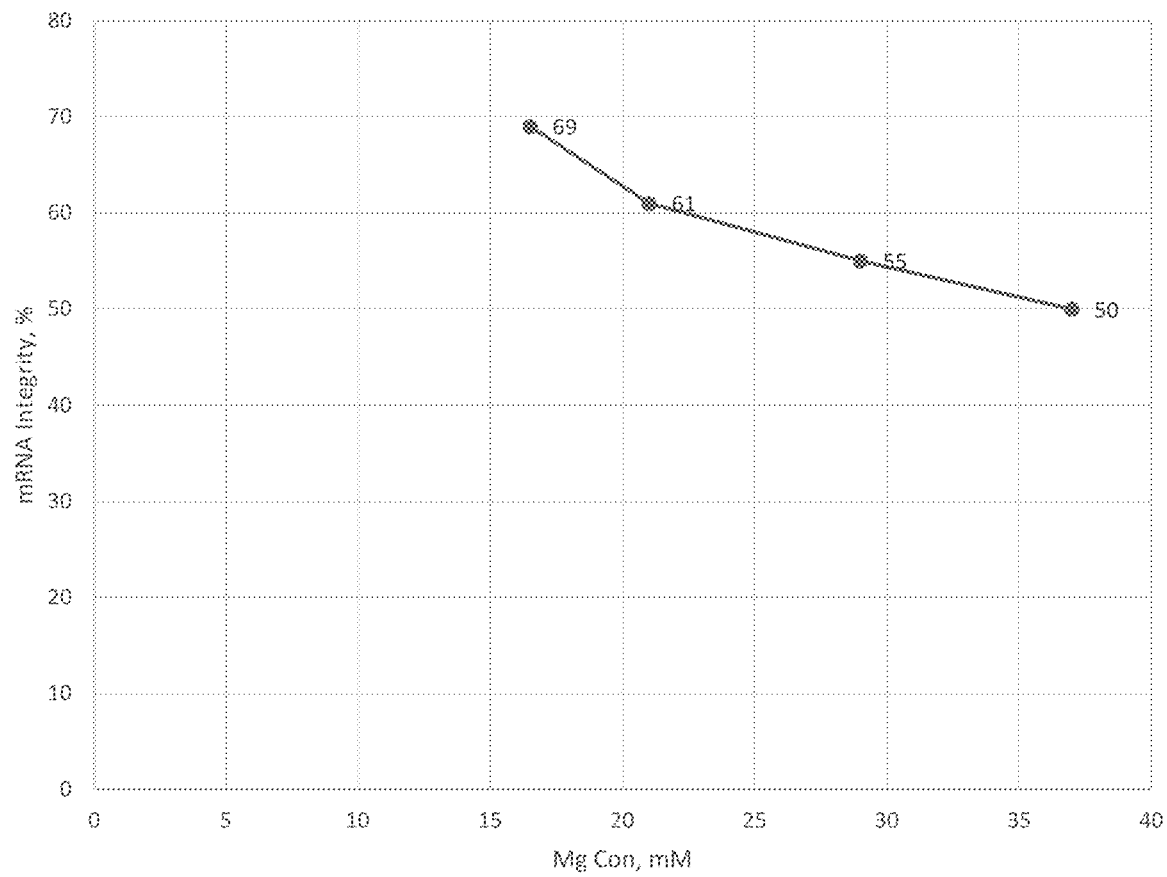
FIG. 12B shows the effect of magnesium on 1 kb mRNA integrity in accordance with one embodiment of the present disclosure.

Magnesium ions ($Mg^{2+}$) is an essential component in an RNA in vitro transcription buffer system to initiate the transcription with Cap analogues rather than GTP. Conventional buffer systems for RNA in vitro transcription (e.g., HEPES buffer, Tris-HCl buffer) may contain high concentrations of free magnesium ions, because free $Mg^{2+}$ ions may be required to guarantee a high activity of the RNA polymerase enzyme. During in vitro transcription process, $Mg^{2+}$ complexes with NTP during the reaction, keeping no extra free $Mg^{2+}$ ions present in buffer systems is important for ensuring high capping efficiency and high integrity of transcribed mRNA. Therefore, higher concentration of $Mg^{2+}$ can cause problems, especially in the context of high-yield/industrial-scale RNA production. Some of the problems associated with free $Mg^{2+}$ ions in the production of RNA may include magnesium-driven precipitates, which may lead to a drop in the free $Mg^{2+}$ concentration, resulting in depletion of magnesium ions from the RNA polymerase reaction center. A consequence of that would be a less efficient RNA in vitro transcription. To assess the impact of Mg concentration on mRNA IVT yield and integrity, IVT were performed in the presence of increasing Mg concentrations. By keeping final Mg concentration at 16.5 mM, 21 mM, 29 mM, and 37 mM, respectively, in the IVT reaction, the concentration of free $Mg^{2+}$ after complexing with NTPs and cap analogues were at −12 mM, −8 mM, 0 mM and +8 mM, respectively, in the IVT reaction system. The mRNA yield reduced when $Mg^{2+}$ concentration increased (FIG. 12A), and the mRNA integrities also reduced when $Mg^{2+}$ concentration increases in the IVT system (FIG. 12B).

EXAMPLES

Example 1

Construction of DNA Template
Encoding Poly A Tail in DNA Template

Poly A tail can be encoded in the DNA template by using appropriately tailed PCR primers. A forward primer and a reverse primer including poly-T sequence oligos were synthesized by methods known in the art. Primers used here were synthesized through solid phase oligo synthesis, such as, but not limited to, solid phase chemistry, then assembled in a PCR reaction using a reverse primer containing a poly-T sequence.

Forward Primer:
(SEQ ID NO: 17)
GCTTAGGAAATTAATACGACTCACTATAAGG

Reverse Primer:
(SEQ ID NO: 18)
tttttttttttttttttttttttttttttttttttttttttttttttt tttttttttttttttttttttttttttttttttttttttttttttttt gccgccactcagactttattc The reaction mixture was as set forth below in Table 3.

TABLE 3

| Reagent | Vol, µl |
| --- | --- |
| 5× PCR Buffer | 20 |
| 10 mM dNTPs | 3 |
| 10 µM Forward Primer | 1-3 |
| 10 µM Reverse Primer | 1-3 |
| DNA Plasmid, 4 ng/µl | 1~4 |
| DNA Polymerase | 2 |
| (1-10M) Betaine | 10 |
| Water | 56 |
| Total | 100 |

DNA templates containing T7 promoter (SEQ ID NO: 10), 5' UTR (SEQ ID NO: 9), Kozak sequence (GCCACC), eGFP coding sequence, and 5' UTR (SEQ ID NO: 2) were sub-cloned into pVAX vector, an poly-A tails were added to DNA template encoding enhanced green fluorescent protein (eGFP) in the DNA using (i) reverse primer (SEQ ID NO: 18) with different length of Ts, the length of resulted DNA templates with 100As, 80As, 60As and 40As were confirmed by DNA Bio analyzer (Agilent DNA 7500 kit) test (FIG. 1).

TABLE 4

| Reagent | Reaction of the present disclosure Vol (µl) | Reaction #1 Vol (µl) | Reaction #2 Vol (µl) | Reaction #3 Vol (µl) |
| --- | --- | --- | --- | --- |
| 5× PCR Buffer | 20 | 20 | 20 | 20 |
| 10 mM dNTPs | 3 | 3 | 3 | 3 |
| 10 µM Forward Primer | 1-3 | 1-3 | 1-3 | 1-3 |
| 10 µM Reverse Primer | 1-3 | 1-3 | 1-3 | 1-3 |
| DNA Plasmid, 4 ng/µl | 1-10 | 1-10 | 1-10 | 1-10 |
| DNA Polymerase | 2 (KAPA) | 2 (KAPA) | 2 (Super Fi2) | 2 (KAPA) |
| (1-10M) Betaine | 10 | 0 | 10 | 10 |
| Water | 56 | 56 | 56 | NA |
| $MgCl_2$ | 0 | 0 | 0 | 0.5 mM |
| Total | 100 | 100 | 100 | 100 |

Figure 1B:
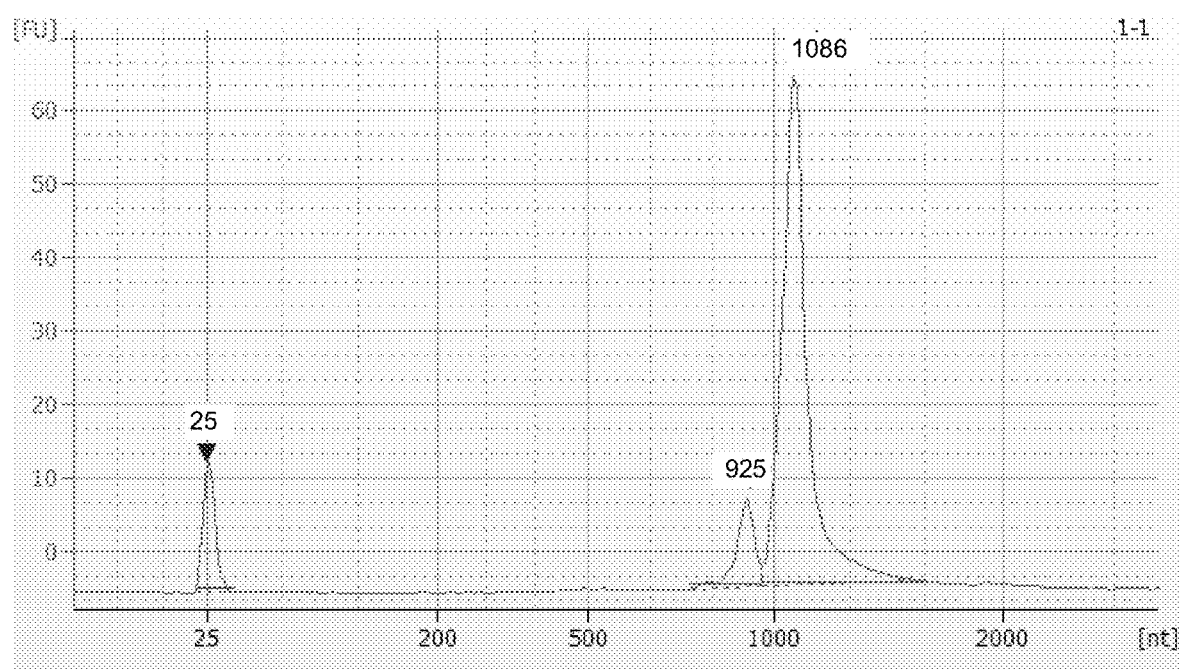
FIG. 1B shows that more than 90% of PCR product for eGFP template has 100A tails added by the disclosed PCR method in example 1 at an average length of 1086 bps.

KAPA = KAPA HiFi HotStart DNA Polymerase
Super Fi2 = Invitrogen Platinum SuperFi I I DNA Polymerase
NA = not available Reactions #1-#3 (Table 4) with regular PCR method failed to add poly A tail and resulted a DNA product at a length of 969 bps. In contrast, FIG. 1A shows that using the methods of the present disclosure, DNA with 1 OCA tail was generated with an average length of 1086 bps at a purity of ~90%. FIG. 1B shows that more than 90% of PCR product of eGFP template has 1 OCA tails at an average length of 1086 bps.

Cloning 5' UTR and 3' UTR into DNA Template

Different UTRs were cloned into a vector comprising an eGFP target DNA template during gene synthesis. Gene fragment containing 17 promoter (SEQ ID NO: 10), 5' UTR (SEQ ID NO: 9), Kozak sequence (GCACC), eGFP coding sequence, and 3' UTR (SEQ ID NO: 2) and were prepared by gene synthesis and then sub-cloned into vector pVAX for generating plasmid for mRNA preparation. The 5' UTR and 3' UTR pairs are shown in Table 5.

TABLE 5

| eGFP mRNA | 5'-UTR | 3'-UTR |
|---|---|---|
| #1 | CTTGTCTCGCTCCGGGGAACG CTCGGAAACTCCCGGCCGCCG CCACCCGCGTCTGTTCTGTTAC ACAAGGGAAGAAAAGCCGCTG CCGCACTCCGAGTGT (SEQ ID NO: 1) | TAAGCTGGAGCCTCGGTGGCCATGC TTCTTGCCCCTTGGGCCTCCCCCCA GCCCCTCCTCCCCTTCCTGCACCCG TACCCCCGTGGTCTTTGAATAAAGT CTGAGTGGGCGGCA (SEQ ID NO: 2) |
| #2 | CTTGTCTCGCTCCGGGGAACG CTCGGAAACTCCCGGCCGCCG CCACCCGCGTCTGTTCTGTTAC ACAAGGGAAGAAAAGCCGCTG CCGCACTCCGAGTGT (SEQ ID NO: 1) | TTAATTAAGCTGCCTTCTGCGGGGC TTGCCTTCTGGCCATGCCCTTCTTCT CTCCCTTGCACCTGTACCTCTTGGT CTTTGAATAAAGCCTGAGTAGGAAG TCTAG (SEQ ID NO: 4) |
| #3 | CTTGTCTCGCTCCGGGGAACG CTCGGAAACTCCCGGCCGCCG CCACCCGCGTCTGTTCTGTTAC ACAAGGGAAGAAAAGCCGCTG CCGCACTCCGAGTGT (SEQ ID NO: 1) | CTCGAGCTGGTACTGCATGCACGCA ATGCTAGCTGCCCCTTTCCCGTCCT GGGTACCCCGAGTCTCCCCCGACCT CGGGTCCCAGGTATGCTCCCACCTC CACCTGCCCCACTCACCACCTCTGC TAGTTCCAGACACCTCCCAAGCACG CAGCAATGCAGCTCAAAACGCTTAG CCTAGCCACACCCCCACGGGAAACA GCAGTGATTAACCTTTAGCAATAAAC GAAAGTTTAACTAAGCTATACTAACC CCAGGGTTGGTCAATTTCGTGCCAG CCACACCCTGGAGCTAGC (SEQ ID NO: 8) |
| #4 | CACTCGCGCTGCCATCACTCTT CCGCCGTCTTCGCCGCCATCCT CGGCGCGACTCGCTTCTTTCGG TTCTACCAGGTAGAGTCCGCCG CCATCCTCCACC (SEQ ID NO: 3) | TAAGCTGGAGCCTCGGTGGCCATGC TTCTTGCCCCTTGGGCCTCCCCCCA GCCCCTCCTCCCCTTCCTGCACCCG TACCCCCGTGGTCTTTGAATAAAGT CTGAGTGGGCGGCA (SEQ ID NO: 2) |
| #5 | GAGAATAAACTAGTATTCTTCTG GTCCCCACAGACTCAGAGAGAA CCCGCCACC (SEQ ID NO: 5) | CTCGAGCTGGTACTGCATGCACGCA ATGCTAGCTGCCCCTTTCCCGTCCT GGGTACCCCGAGTCTCCCCCGACCT CGGGTCCCAGGTATGCTCCCACCTC CACCTGCCCCACTCACCACCTCTGC TAGTTCCAGACACCTCCCAAGCACG CAGCAATGCAGCTCAAAACGCTTAG CCTAGCCACACCCCCACGGGAAACA GCAGTGATTAACCTTTAGCAATAAAC GAAAGTTTAACTAAGCTATACTAACC CCAGGGTTGGTCAATTTCGTGCCAG CCACACCCTGGAGCTAGC (SEQ ID NO: 8) |
| #6 | CTTGTCTCGCTCCGGGGAACG CTCGGAAACTCCCGGCCGCCG CCACCCGCGTCTGTTCTGTTAC ACAAGGGAAGAAAAGCCGCTG CCGCACTCCGAGTGT (SEQ ID NO: 1) | ATTTCTATTAAAGGTTCCTTTGTTCC CTAAGTCCAACTACTAAACTGGGGG ATATTATGAAGGGCCTTGAGCATC (SEQ ID NO: 6) |
| #7 | ATCTGAATGG AGCAGCCAAG CTTGACACTC TAAACCCCTG GACCCTTCTT TTTTGCCCTTGGCT (SEQ ID NO: 7) | TTAATTAAGCTGCCTTCTGCGGGGC TTGCCTTCTGGCCATGCCCTTCTTCT CTCCCTTGCACCTGTACCTCTTGGT CTTTGAATAAAGCCTGAGTAGGAAG TCTAG (SEQ ID NO: 4) |

TABLE 5-continued

| eGFP mRNA | 5'-UTR | 3'-UTR |
|---|---|---|
| #8 | AAATAAGAGAGAAAAGAAGAGT AAGAAGAAATATAAGA (SEQ ID NO: 9) | TAAGCTGGAGCCTCGGTGGCCATGC TTCTTGCCCCTTGGGCCTCCCCCA GCCCCTCCTCCCCTTCCTGCACCCG TACCCCCGTGGTCTTTGAATAAAGT CTGAGTGGGCGGCA (SEQ ID NO: 2) |

Figure 2A:
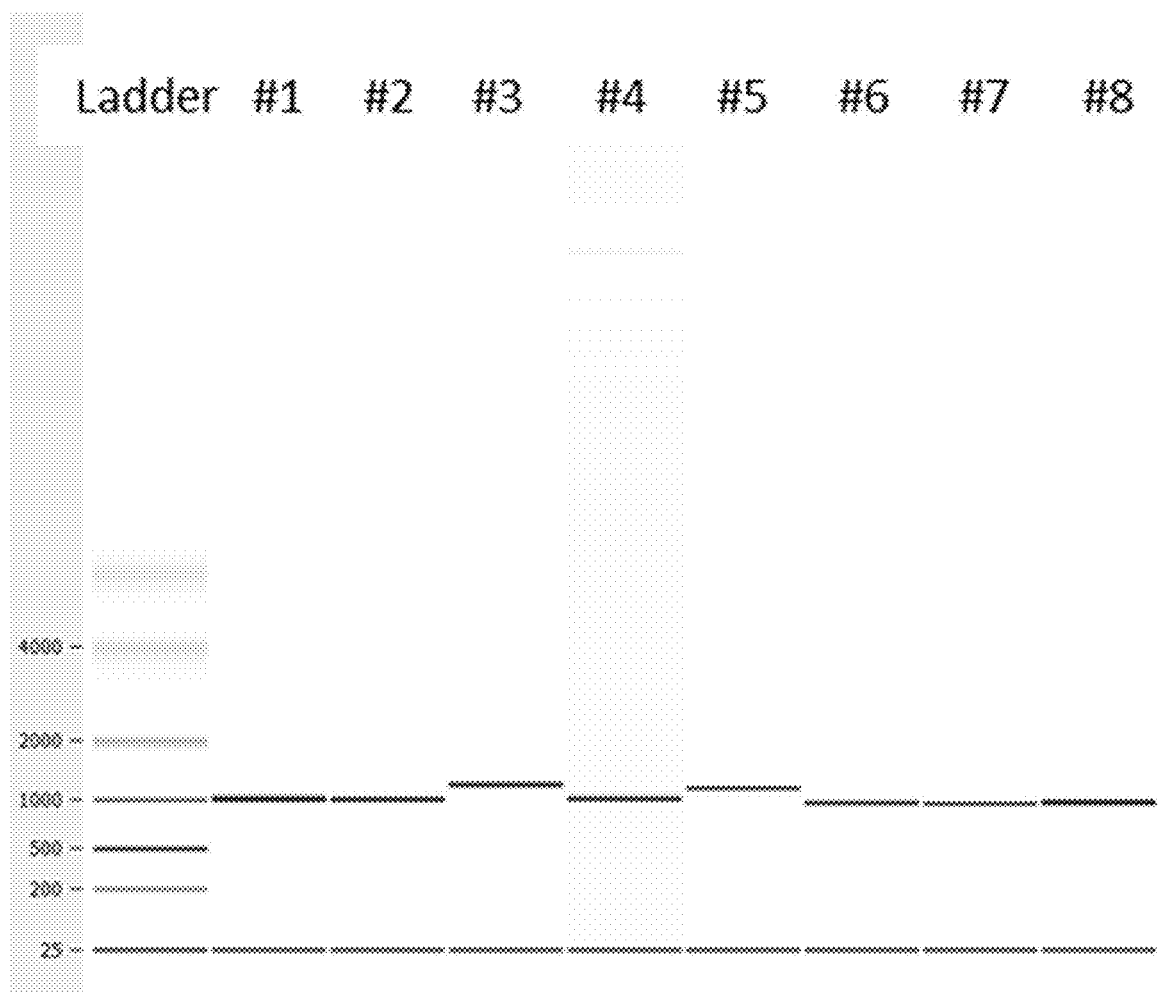
FIG. 2A shows the quality of mRNA prepared by the methods in accordance with one embodiment of the present disclosure.
Figure 2B:
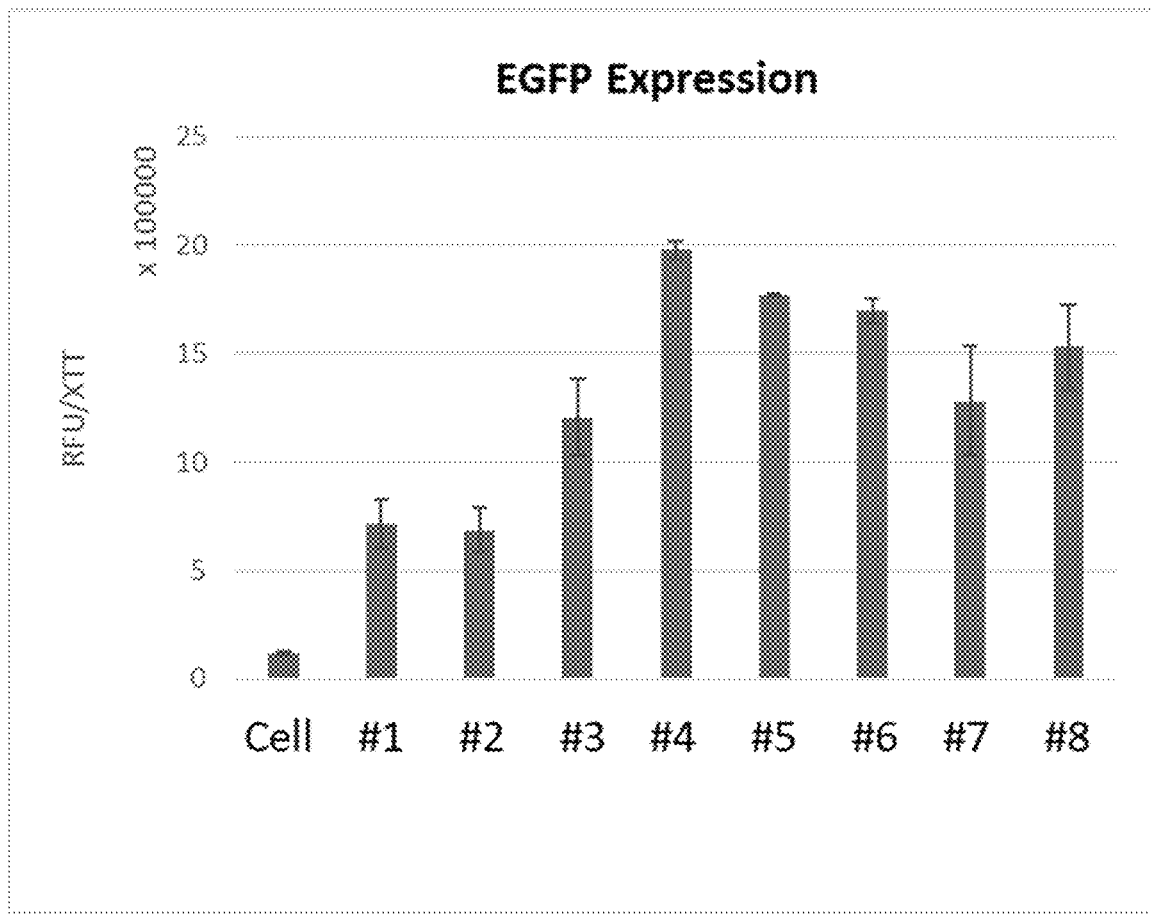
FIG. 2B shows the expression of mRNA prepared by the methods in accordance with one embodiment of the present disclosure.

The plasmids were linearized by restriction enzyme, and then purified to prepare linear plasmid for in vitro transcription to prepare mRNA. mRNAs were prepared by aforementioned co-transcriptional method with Cap [I], then purified by silica membrane column. mRNA quality was tested by Bioanalyzer with Agilent RNA Nano6000 kit (FIG. 2A).

eGFP mRNAs with different UTRs were tested for its expression efficiency on A549 cells. 1 µg of mRNA were transfected with lipofectamine 2000 into each well of A549 cells in 96 well plate, tested in triplicates, and the expression of eGFP level was measured by plate reader for its fluorescence intensity, normalized by cell numbers measured by CyQUANT™ XTT Cell Viability assay. FIG. 2B shows the expression level of mRNA with different UTR combinations. UTR combinations in mRNA #4 (SEQ ID NO: 3 and 2), #5 (SEQ ID NO: 5 and 8), #6 (SEQ ID NO: 1 and 6), and #8 (SEQ ID NO: 9 and 2) yielded higher EGFP expression levels than others, e.g., #1 (SEQ ID NO: 1 and 2), #2 (SEQ ID NO: 1 and 4), #3 (SEQ ID NO: 1 and 8), and #7 (SEQ ID NO: 7 and 4).

Example 2

Construction of DNA Template
Encoding Poly A Tail in DNA Template

High purity of Poly A tail can be encoded in the DNA template by using appropriately chemical modified tailed PCR primers coupled with T7 exonuclease digestion. A phosphorothioate modified forward primer and a reverse primer including poly-T sequence oligos were synthesized by solid phase chemistry with modified phosphoramidites. Modified primers were used to assemble a PCR reaction to generate DNA template for in vitro transcription. The PCR products were further digested with T7 exonuclease (NEB) to remove any truncated DNA product to generate a high purity template for downstream mRNA preparation.

Forward Primer:
(SEQ ID NO: 19)
C*A*C*TGCTTACTGGCTTATCGAAATTAATACGACTCACTATA*G*G*A Reverse Primer:
(SEQ ID NO: 20)
T*mU*T*[T]$_{96}$TGCCGCCCACTCAGACTTTATTCAAAGA*C*C*A
Note:
*indicate phosphorothioate backbone modification, mU indicate 2'-omethyl-Uridine.

The reaction mixture was as set forth below in Table 6.

TABLE 6

(Reaction #4)

| Reagent | Vol, µl |
|---|---|
| 5× PCR Buffer | 20 |
| 10 mM dNTPs | 3 |

TABLE 6-continued (Reaction #4)

| Reagent | Vol, µl |
|---|---|
| 10 µM Forward Primer | 1-3 |
| 10 µM Reverse Primer | 1-3 |
| DNA Plasmid, 10 ng/µl | 1~4 |
| DNA Polymerase | 2 |
| (1-10M) Betaine | 10 |
| Water | 56 |
| Total | 100 |

Reactions #4 (Table 6) with touch up PCR method was used to generate DNA template with uniform polyA tail for downstream application. The touch up PCR was performed with annealing temperature at 62° C. for 5 cycles followed with an annealing temperature of 68° C. for 20 cycles using KAPA HiFi DNA polymerase (Roche). Generated PCR product were purified with DNA Selection magnetic beads (Yeasen) following standard protocol and further digested with T7 exonuclease in NEB buffer 4 at 25° C. for 30 minutes to remove all the impurities.

Example 3

Effects of Promoters on Capping Efficiency

To test the effect of promoters on capping efficiency, plasmids containing different promoters, as listed in Table 1, 5' UTR (SEQ ID NO: 9), eGFP ORF, 3' UTR (SEQ ID NO: 2), and 100 As were prepared by mutagenesis with pVAX vector, the plasmids were purified with maxi-prep and then linearized by restriction enzyme after poly A sequence to generate template for mRNA preparation.

mRNAs were prepared using the linearized plasmid as template, T7 polymerase and Cap [I] AG, N1-Methyl-pseudoUTP by in vitro transcription method disclosed herein. The prepared mRNAs were purified by silica membrane column. Then, capping efficiency for each mRNA was tested. For testing its capping efficiency, a 24-mer probe with 4 DNA nucleotides at the 5' end, and 20 nt of RNA reverse complementary to the 5' end sequence of mRNA, and a 3' end biotin modification was synthesized from Integrate DNA Technologies (IDT), and used to hybridize with the prepared mRNA, which was further digested with Rnase H to cut at the DNA/RNA hybrid position to release the 24-mer of 5' end mRNA, which was further purified with streptavidin magnetic beads and analyzed by LC-MS. Condition for UPLC is 5% B hold 0-0.5 min, 6-20% B over 5 min, Clarity Oligo-xt 2.1×50 mm, 2.6 µm column, 60 C, B=65/35 ACN/water, A=1% HFIP buffer, 0.4 mL/min. Orbitrap Velos Pro Mass Spectrum equipment was used for mass analysis.

Figure 10B:
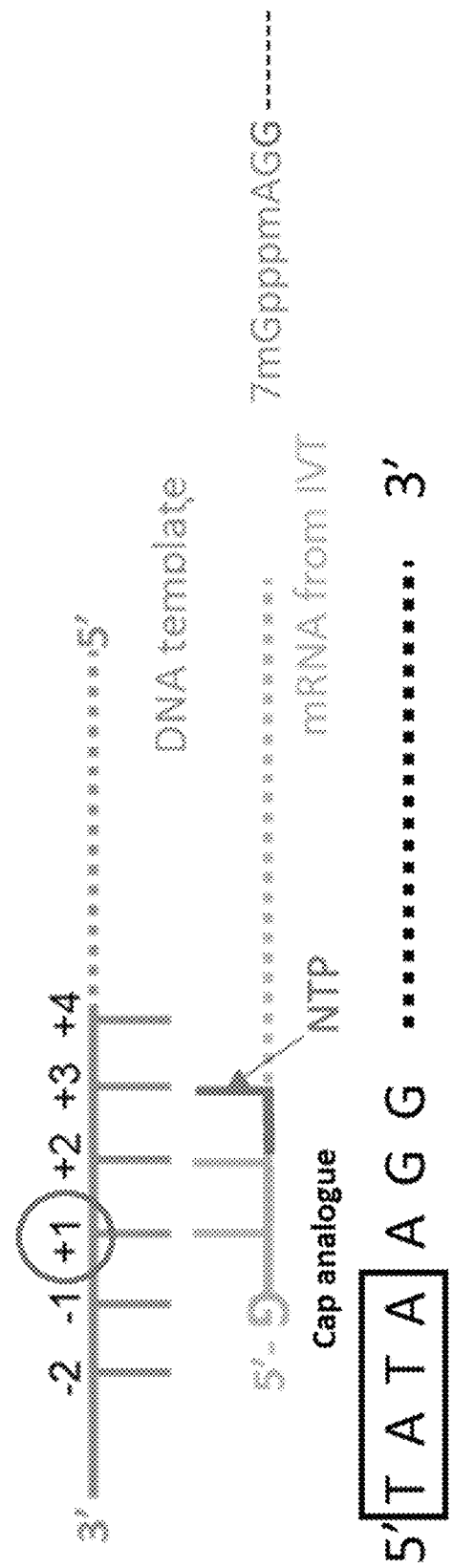
FIG. 10B shows use of cap analogues to initiate in vitro transcription at +1 position in accordance with one embodiment of the present disclosure.
Figure 10C:
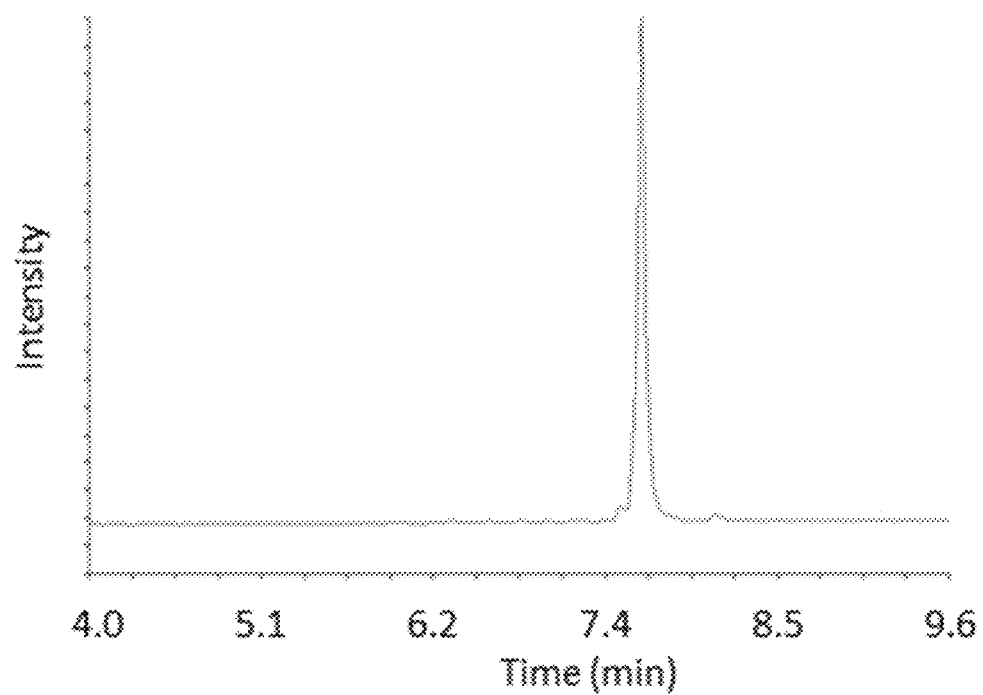
FIG. 10C shows capping efficiency of mRNA prepared by the methods in accordance with one embodiment of the present disclosure.
Figure 10D:
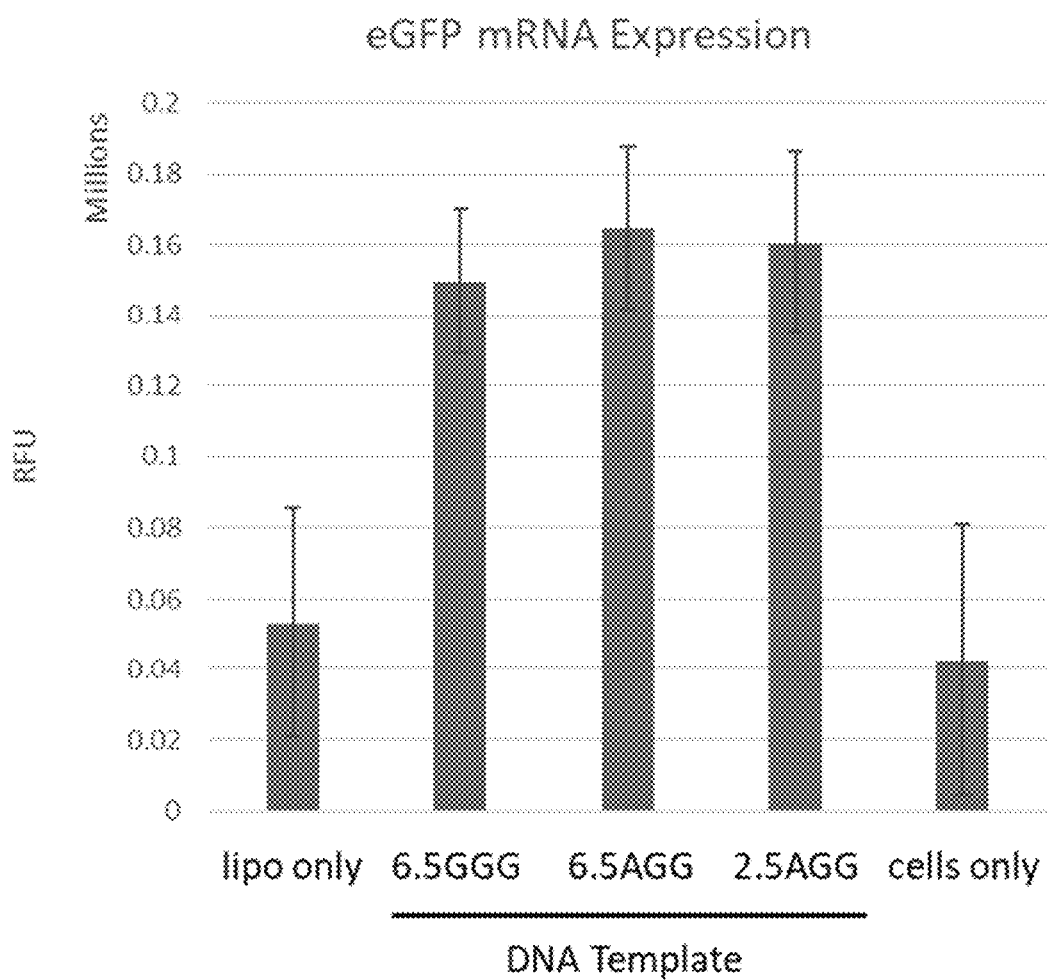
FIG. 10D shows expression levels of eGFP mRNA prepared by the methods in accordance with one embodiment of the present disclosure. IVT reaction through co-transcription with Cap 1 analogue initiated at −1 position with T7GGG promoter had similar mRNA expression intensity comparing to initiating mRNA IVT with cap 1 analogue initiating transcription at +1 position as T7AGG.

FIG. 10A shows an exemplary schematic illustration of using a Cap [I] 3-mer nucleotide, e.g., 7mGpppmAG, to initiate an in vitro transcription at the −1 position of the promoter to prepare capped mRNA, e.g., G is at the +1 position of the promoter. For clarity, the TATA sequence upstream from the +1 position is boxed. Thus, 7mGppp-mAG binds to the −1 and the +1 positions to initiate an in vitro transcription. FIG. 10B shows an exemplary schematic illustration of using a Cap [I] 3-mer nucleotide, e.g., 7mGpppmAG, to initiate an in vitro transcription at the +1 position to prepare capped mRNA, e.g., A is at the +1 position and G is at the +2 position. Thus, 7mGpppmAG binds to the +1 and the +2 positions to initiate an in vitro transcription. FIG. 10C shows an LC-MS data for testing the capping efficiency of exemplary mRNA prepared with cap analogues and disclosed in vitro transcription method. FIG. 10D shows mRNA prepared using the disclosed method of in vitro transcription using template 6.5GGG (SEQ ID NO: 10) starting IVT from −1 position, or using template 6.5AGG (SEQ ID NO: 12) starting IVT from +1 position, or using template 2.5AGG (SEQ ID NO: 15) starting IVT from +1 position generated capped eGFP mRNA with similar expression efficiency in A549 cells.

The capping efficiency was calculated by the ratio of fragment with target capped molecular weight versus total fragments in LC-MS analysis. Capping efficiency test results for the promoters with Cap [I]-AG is listed in Table 7 below:

TABLE 7

| SEQ ID NO: | Promoter | Cap Analogues | Capping Efficiency |
|---|---|---|---|
| 10 | TAATACGACTCACTATAGGG | Cap [I] | 98.80% |
| 11 | TAATACGACTCACTATAGG | Cap [I] | 93.47% |
| 12 | TAATACGACTCACTATAAGG | Cap [I] | 92.18% |
| 13 | TAATACGACTCACTATAGAT | Cap [I] | 97.73% |
| 14 | TAATACGACTCACTATAGA | Cap [I] | 93.61% |
| 15 | TAATACGACTCACTATTAGG | Cap [I] | 93.17% |

Table 7 shows that ORF driven by promoter (SEQ ID NO: 10) yielded eGFP mRNA with higher capping efficiency of Cap [I] than that driven by the other promoters.

Higher organisms usually have a more extensively methylated cap structure, while yeast mRNAs mainly contain a Cap0 structure. 2'-o-methylation at the $2^{nd}$ base after triphosphate bond is called Cap2 structure. About half of polyA tailed mRNA molecules in human is found to have a Cap2 structure. Cap1 and Cap2 methylation in U2 snRNA are essential for its spliceosome formation and related splicing activity (Werner Maria, Purta Elzbieta, et al, *Nucleic Acid Research,* 2011, Vol 30 No. 11, P4756-4768; the content of which is hereby incorporated by reference by its entirety). New cap analogues were evaluated as capped analogues for preparing capped mRNA through one step in vitro transcription reaction. Cap [11] were added into the IVT reaction system following the method disclosed herein, with modified T7 polymerase P266L mentioned above. The resulted mRNA was purified with silica membrane column and tested for capping efficiency using RNase H digestion coupled with LC-MS method.

Example 4

Determination of Poly A Tail Length

Poly A tail length can be determined by using a method of digesting the mRNA samples with RNase T1, which can cut after G base of RNA, then purifying the digested fragments and recovering the poly A tail fragment with oligo dT magnetic beads, eluting the purified poly A fragment after denaturing with high temperature water or denaturing reagent, followed by analyzing the poly A tail length by BioAnalyzer or other capillary electrophoresis, or LC-MS.

mRNA tail length was tested using RNase T1 digestion coupled with bioanalyzer for poly A fragment length analysis. Briefly, mRNA was digested with RNase T1, which will cut mRNA after every base of rG, and then purify the poly A fragment with oligo-dT magnetic beads. The purified poly A fragment will be subjected to analysis with bioanalyzer using small RNA Kit.

Figure 3:
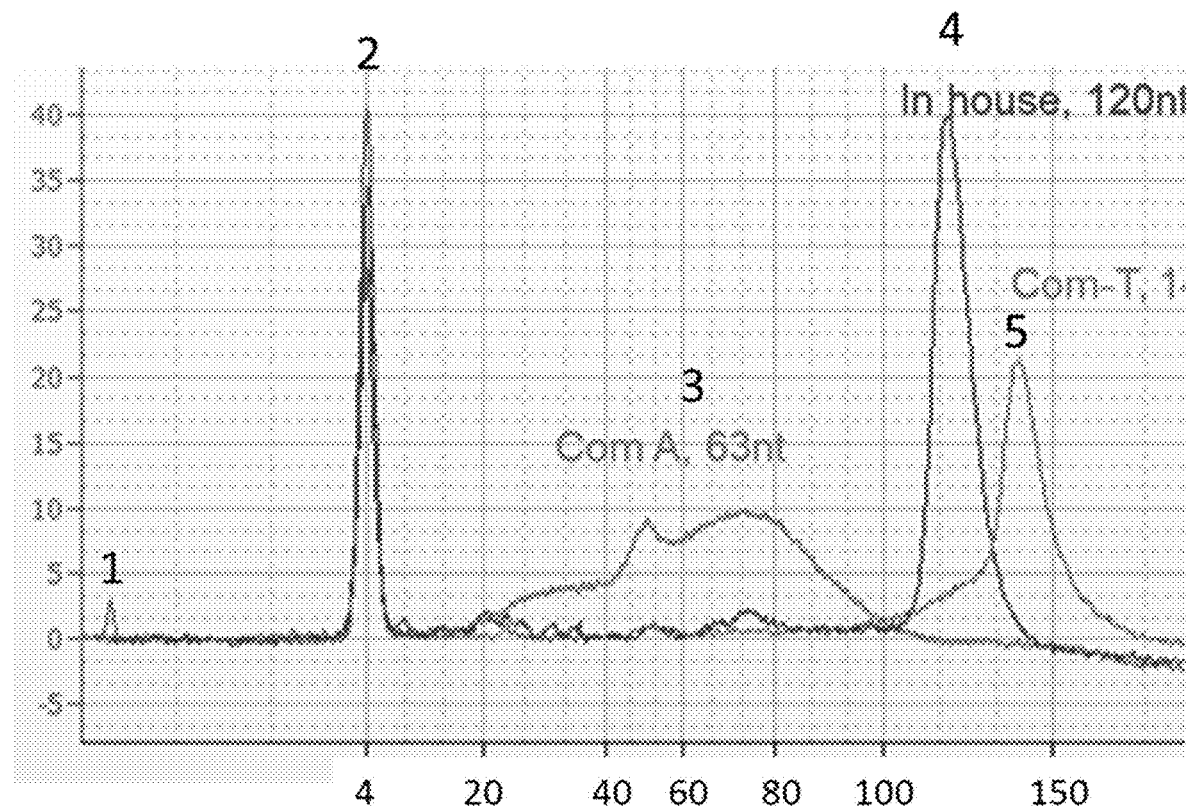
FIG. 3 shows poly A fragment length analysis in accordance with one embodiment of the present disclosure.
Figure 4:
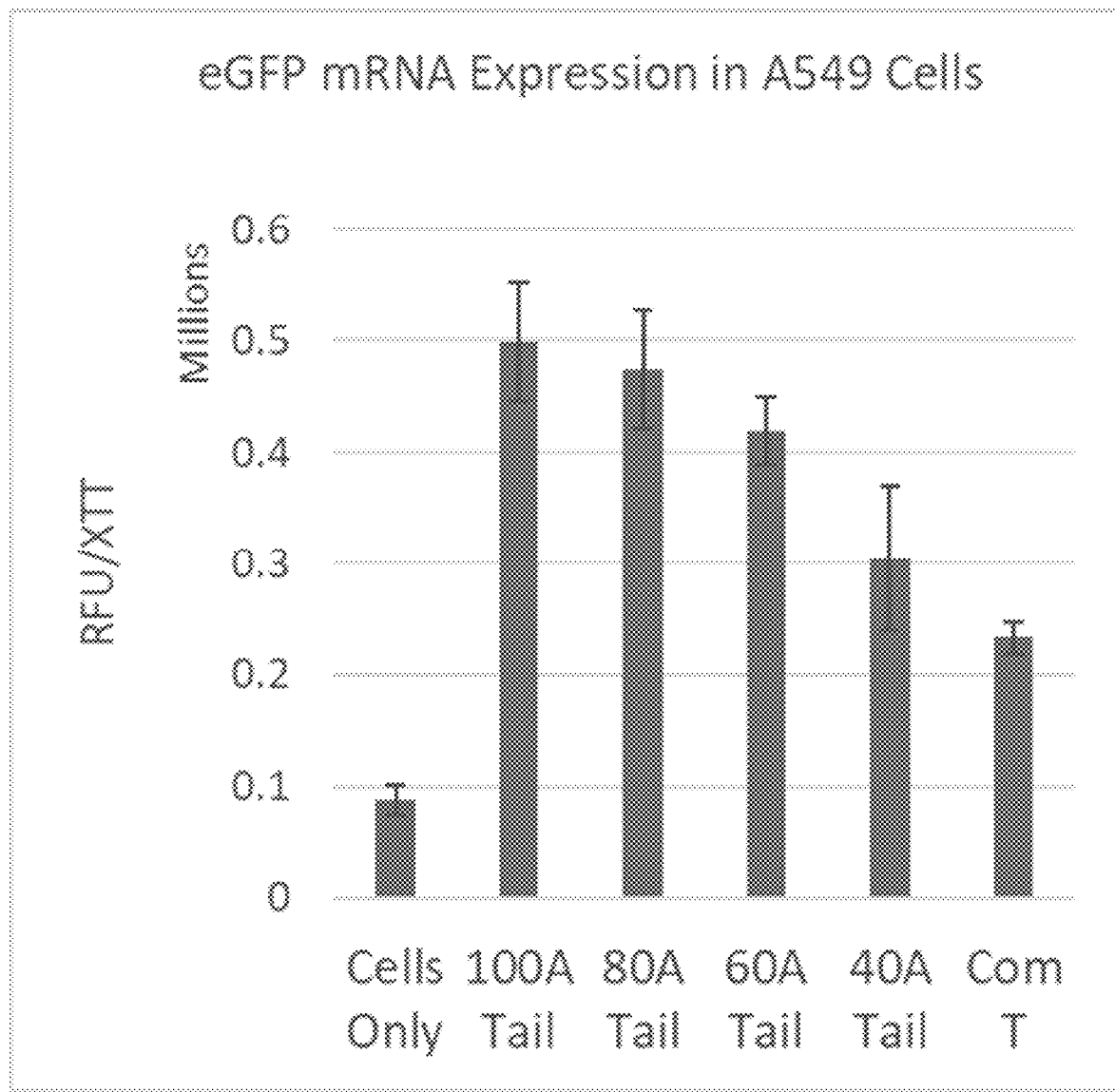
FIG. 4 shows effect of poly A tail lengths on mRNA expression in accordance with one embodiment of the present disclosure.
Figure 5A:
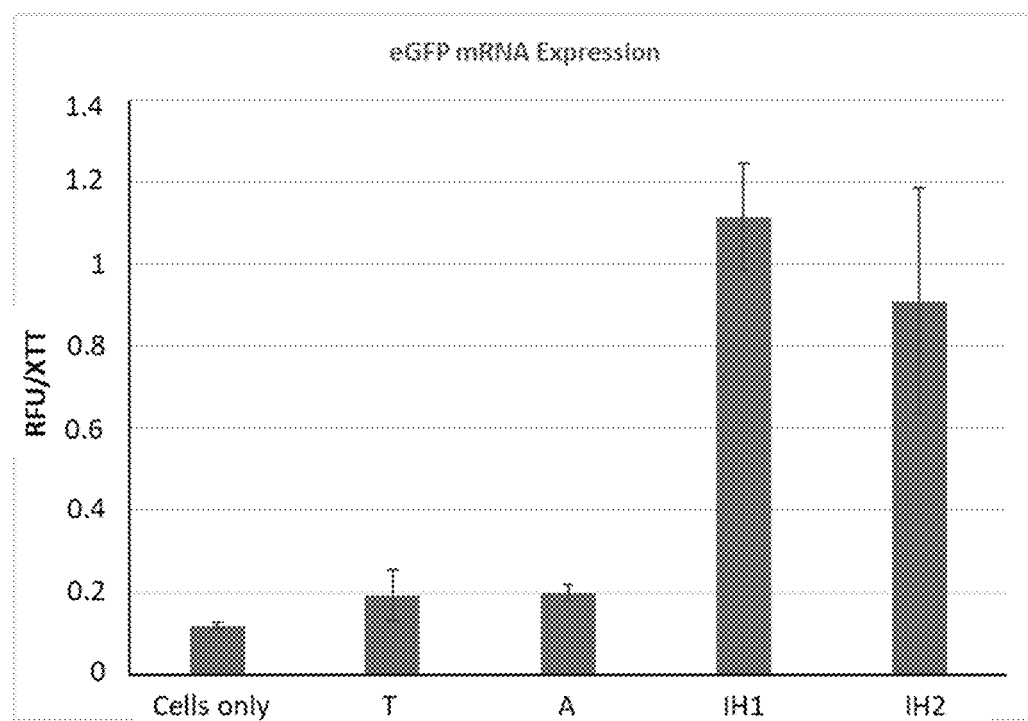
FIG. 5A shows comparison of expression levels of eGFP mRNA prepared by various methods in accordance with one embodiment of the present disclosure, eGFP expression relative intensity was measured by fluorescent plat reader.
Figure 5B:
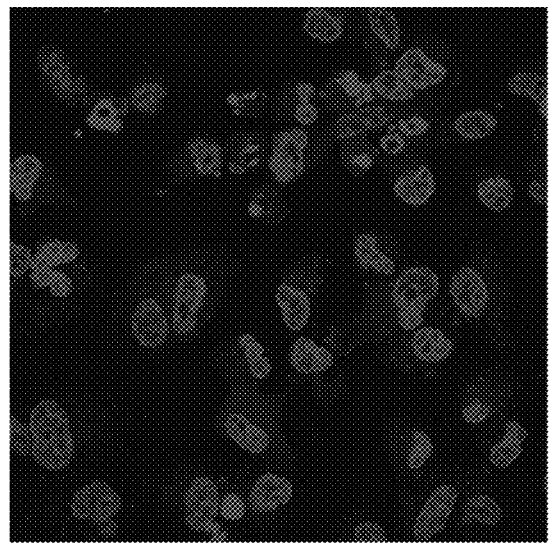
FIG. 5B shows the relative eGFP expression intensity in cells as measured by confocal microscopy.
Figure 5B:
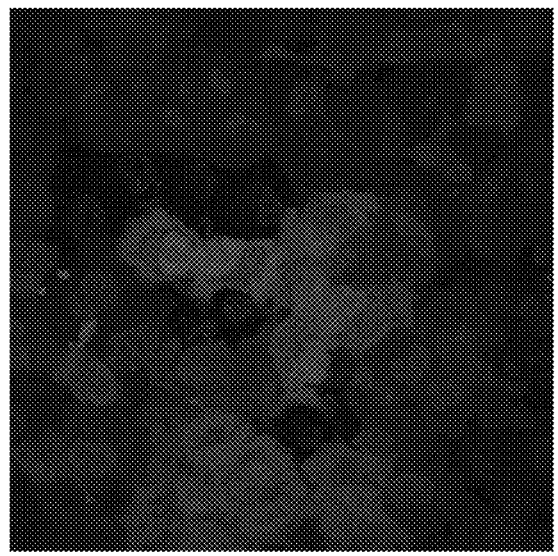
Figure 5B:
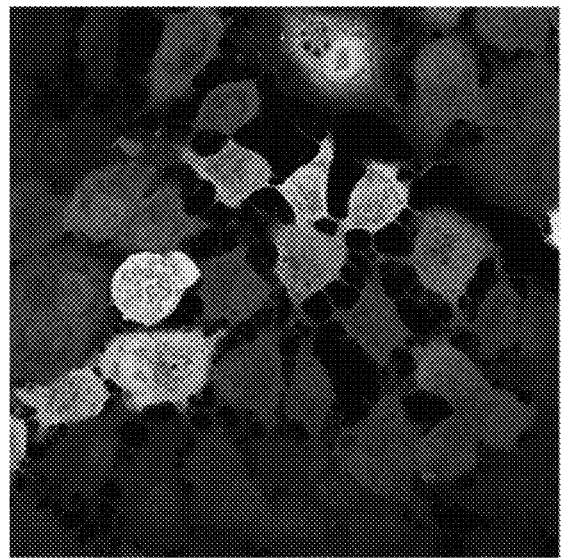

PolyA tail length is a critical quality attribute for mRNA, the result from FIG. 4 suggested that mRNA with longer polyA tails had better mRNA translation/expression efficiency in cells. In general, mRNA with longer than 80A could expect good protein translation. FIG. 3 shows mRNA sample polyA tail length analysis result by bioanalyzer. Peak 3: poly A tail of mRNA acquired from Company A, which is a typical distribution of poly A tail generated by poly A polymerase resulting in a broad range of length distribution from 20 to 100 nts with an average poly A tail length of 63 nts; Peak 4: poly A tail of mRNA generated using the PCR-based method disclosed herein resulting in a signature of uniform distribution around the size of 120±20 nts and a sharp distribution; and Peak 5: poly A tail of mRNA generated using the method of Company T resulting in an average tail length of 140 nt but broader distribution. The results show that using poly A tails generated by PCR-based methods described in Example 1 resulted in generating high quality DNA template with uniform polyA length distribution, which further contributed to high quality mRNA with uniformly distributed poly A tail. The mRNA translation or expression efficiency as shown in FIGS. 5A and 5B suggested in house (IH) eGFP mRNA has stronger expression than Company T (T), and eGFP from company A (A) had the lowest expression. Peak 1 is a noise peak. Peak 2 (FIG. 3) shows lower marker in the small RNA bioanalyzer kit which is an internal size control at the length of 4 nt added in each sample run for analysis alignment.

Effects of Poly A Tail Length on Gene Expression eGFP mRNA with different length of poly A tails were prepared through aforementioned co-transcription capping method with Cap [I], UTP were 100% substituted with N1-methyl-pseudoUTP, the resulted mRNA were purified with silica membrane purification method for cell expression assay. A549 cells were plated on 96 well plate one day before experiment, 0.5 µg of mRNA were transfected into each well with lipofectamine 2000, cells only was non-treated background control, groups of EGFP-mRNA-100A, EGFP-mRNA-80A, EGFP-mRNA-60A, EGFP-mRNA-40A or eGFP mRNA prepared in house using the disclosed method here were tested in triplicate. The expression level of eGFP protein was measured by plate reader the second day, normalized with live cell numbers tested by CyQUANT™ XTT Cell Viability.

FIG. 4 shows expression level of eGFP in A549 cells increased as the length of the poly-A tail of mRNAs increased. mRNAs with minimum of 60As were readily expressed and translated.

Example 5

In Vitro Transcription

Both linearized DNA plasmid and PCR product can be used as DNA template for preparing mRNA by in vitro transcription. To test in vitro transcription conditions, plasmid vector containing T7 promoter (SEQ ID NO: 11), 5'-UTR (SEQ ID NO: 9), eGFP coding sequences, 3'-UTR (SEQ ID NO: 2), and poly A tail (100A) was linearized by BspQ1, or Bbs1 restriction enzyme, and purified with ethanol precipitation. The linearized plasmid was transcribed with T7 RNA polymerase (M3Q), cap analogues (Cap [I]), 1 Ox transcription buffer, NTPs, and RNase Inhibitor to prepare capped mRNA.

TABLE 8

| Component | Condition | Units |
| --- | --- | --- |
| Buffer Type | Hepes, pH 8.0 | NA |
| Buffer Concentration | 50 | mM |
| DTT | 20 | mM |
| RNase Inhibitor | 0.02 | U/μL |
| NTPs | 4 | mM |
| Cap Analogue | 7 | mM |
| MgOAc | 25 | mM |
| Spermidine | 2 | mM |
| DNA* | 0.03 | μg/μL |
| Inorganic pyrophosphatase | 0.3 | mU/μL |
| RNA Polymerase | 1.5 | U/μL |
| Incubation temperature | 30 | °C. |
| Incubation time | 4 | hours |

*eGFP DNA tempalte, luciferase DNA template, or espCas9 DNA template.

Cap analogues may be any capped analogues described herein. HEPES buffer was 400 mM HEPES in water, pH 7.5; Iris buffer was 400 mM Tris-HCl buffer at pH 7.5. RNA polymerase can be wild type 17 RNA polymerase or 17 RNA polymerase with mutations to enhance stability and/or the ability to incorporate Cap [II] analogues. In vitro transcription can be set up DNase free, RNase free plastic tubes ranging from 0.2 mL to 15 mL at a defined temperature with or without shaking.

Figure 9A:
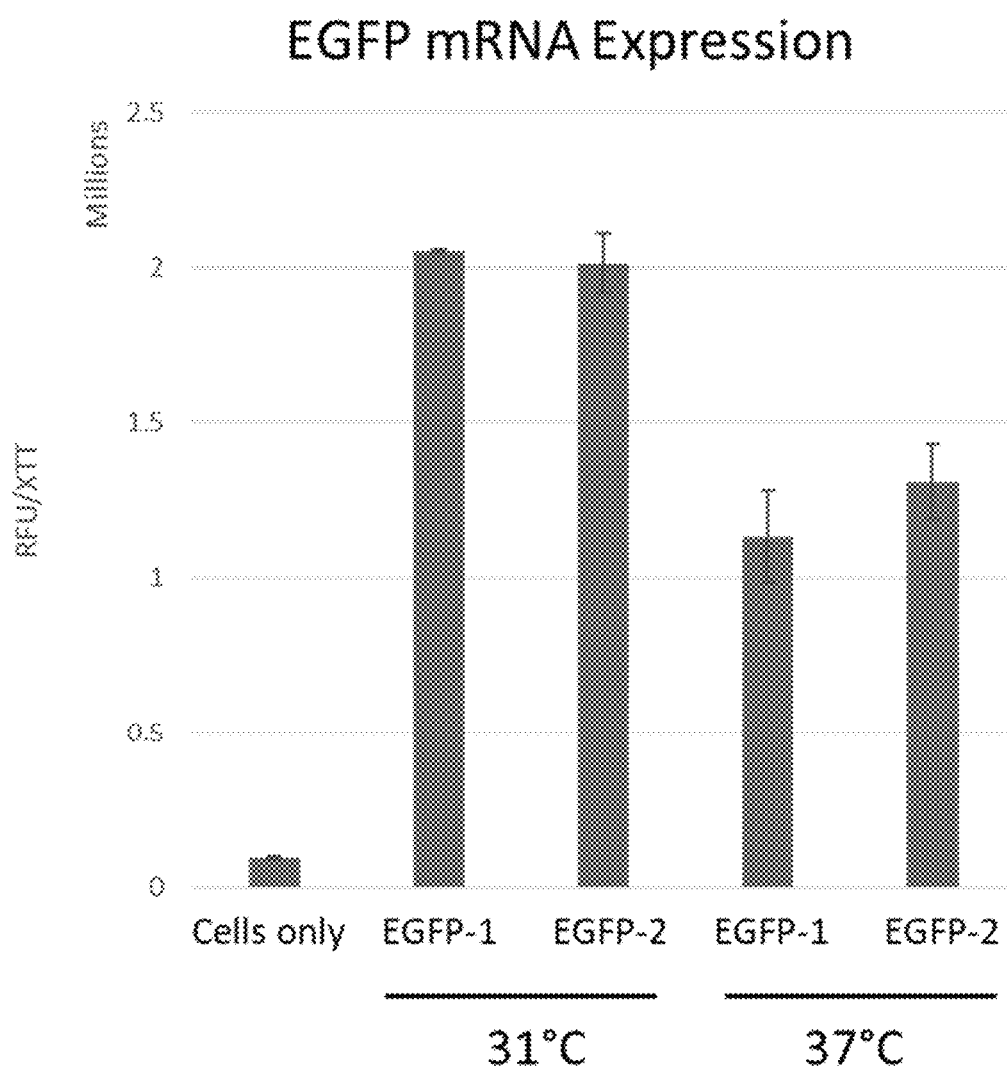
FIG. 9A shows the eGFP mRNA expression efficiency measured by fluorescent plate reader, mRNAs were prepared by in vitro transcription at different reaction temperature, 31° C. or 37° C.
Figure 9B:
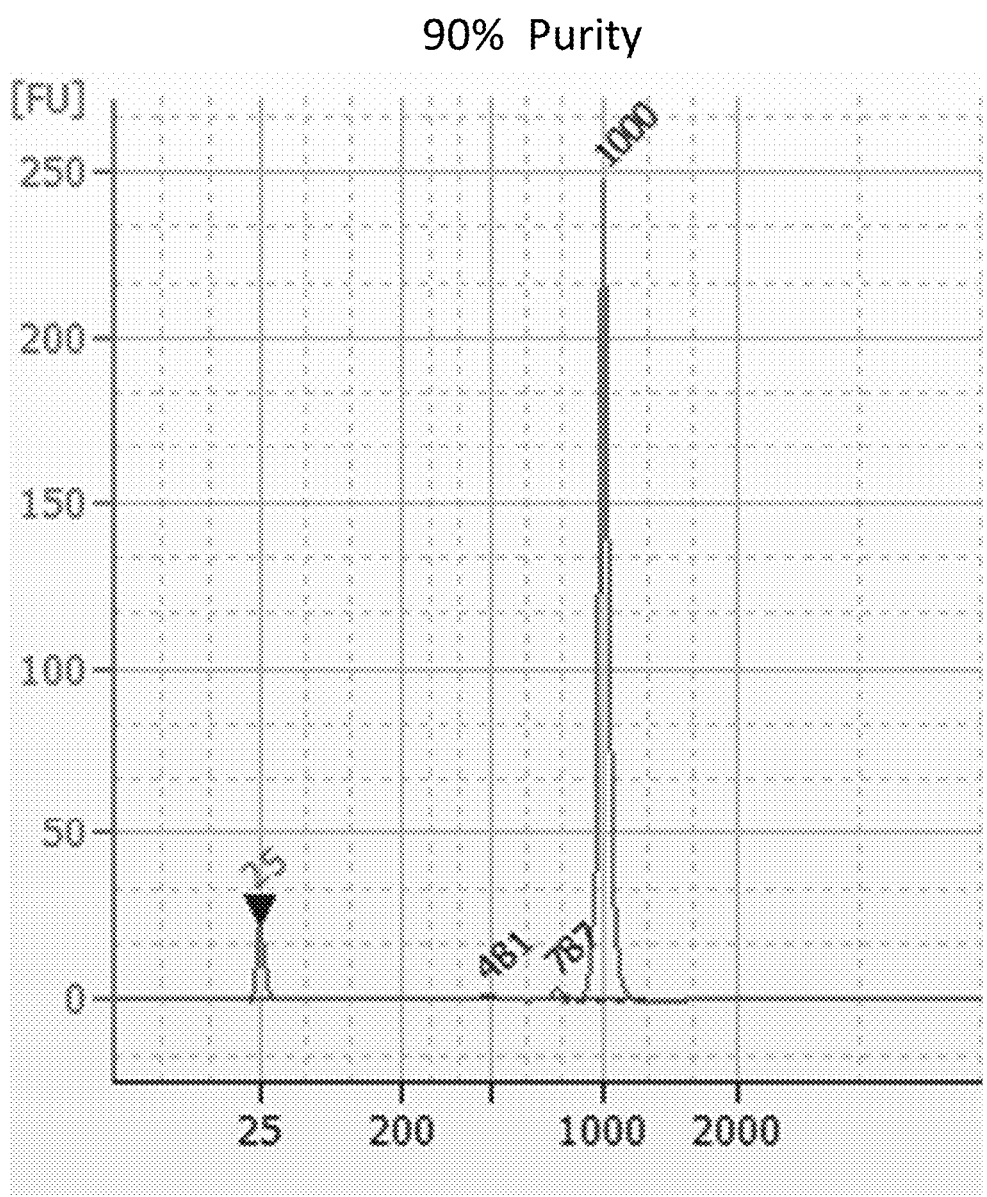
FIG. 9B shows 31° C. IVT reaction derived eGFP mRNA purity measured by bioanalyzer.

The in vitro transcription mixture and conditions were as set forth in Table 8. More specifically, a 1 Ox Buffer containing HEPES, or Tris buffer was prepared by adding magnesium acetate, spermidine, and DTT and stored at −20° C. for use. In the in vitro transcription reaction, the buffer, DNase free and RNase free water, NTPs, and cap analogue were added into a reaction tube, followed by adding DNA template, T7 polymerase, RNase inhibitor, and Inorganic pyrophosphatase. The reaction was kept at designated temperature ranging from 20-40° C. for 1 to 6 hours for transcription to take place. Then, DNA templates were removed by digestion with DNase1 RNase free enzyme.

eGFP mRNA thus prepared with promoter (SEQ ID NO: 15) was used for expression efficiency assay in A549 cells. Two batches of Cap [1], 100% N1-methyl-pesudoUTP modified, 100A tailed eGFP mRNA were prepared and named as in house (IH)1 and IH2. Cells only, which indicates cells were not treated with mRNA, served as a background control. For comparison, eGFP mRNA were also acquired from Company T (T) and Company A (A), in which Company T used co-transcriptional capping with promoter of SEQ ID NO: 12, Company A used traditional enzymatical in vitro transcription to prepare un-capped mRNA, then added cap analogues with Vaccinia virus capping enzyme and 2'-O-Methyltransferase, and poly A tail was added tail using polyA polymerase. eGFP mRNA samples were transfected into A549 cells in 96 well black well transparent bottom plates in triplicates, per 1 ug of mRNA was transfected with 0.5 uL of lipofectamine 2000 with OptiMEM into cells. The cells were incubated with mRNA overnight, then the expression efficiency was measured by relative fluorescence intensity of eGFP mRNA treated cells by plate reader, and normalized by relative cell number as tested by Cyquant XTT cell viability assay. FIG. 5 shows eGFP mRNA expression prepared by the methods of the present disclosure, i.e., IH1 and IH2, are higher than that prepared by the methods of Company T (T) and Company A (A). in which Company T used co-transcriptional capping with promoter of SEQ ID NO: 12, Company A used traditional enzymatical in vitro transcription to prepare un-capped mRNA, then added cap analogues with Vaccinia virus capping enzyme and 2'-O-Methyltransferase, and poly A tail was added tail using polyA polymerase. eGFP mRNA samples were transfected into A549 cells in 96 well black well transparent bottom plates in triplicates, per 1 ug of mRNA was transfected with 0.5 uL of lipofectamine 2000 with OptiMEM into cells. The cells were incubated with mRNA overnight, then the expression efficiency was measured by relative fluorescence intensity of eGFP mRNA treated cells by plate reader, and normalized by relative cell number as tested by Cyquant XTT cell viability assay. FIG. 5 shows eGFP mRNA expression prepared by the methods of the present disclosure, i.e., IH1 and IH2, are higher than that prepared by the methods of Company T (T) and Company A (A). FIG. 9 shows that eGFP mRNA prepared by in vitro transcription reaction at 31° C. has higher expression efficiency than from reaction at 37° C.

Figure 6:
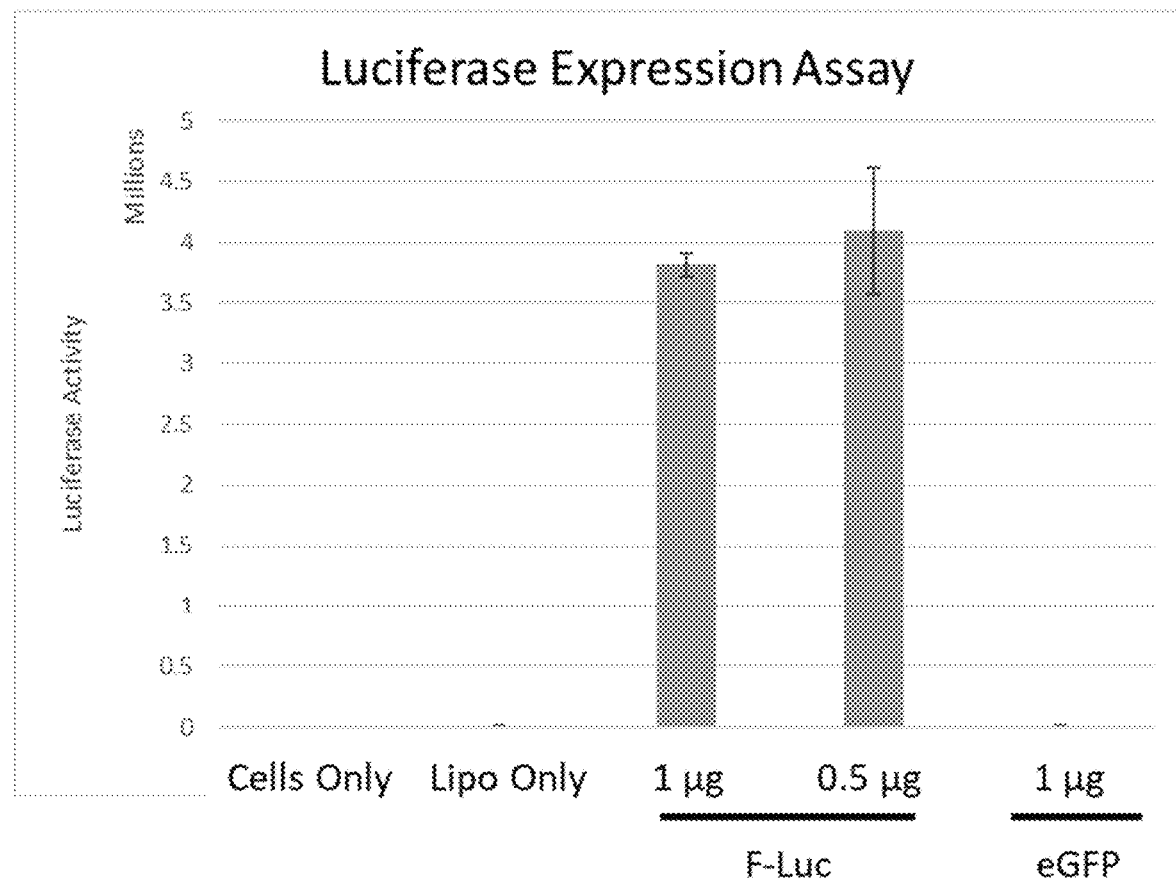
FIG. 6 shows expression levels of luciferase mRNA prepared by the methods in accordance with one embodiment of the present disclosure.

To determine the luciferase mRNA expression using the methods of the present disclosure, plasmid vector (F-Luc) containing T7 promoter (SEQ ID NO: 15), 5'-UTR (SEQ ID NO: 10), luciferase coding sequence, 3'-UTR (SEQ ID NO: 2), and poly A tail (100A) was used in in vitro transcription followed by lipofectamine (Lipo)-mediated transfection into A549 cells. FIG. 6 shows that luciferase mRNA are readily expressed and translated as compared with that of the controls, e.g., cells only, Lipo only, and eGFP transfected cells as negative controls.

Figure 7:
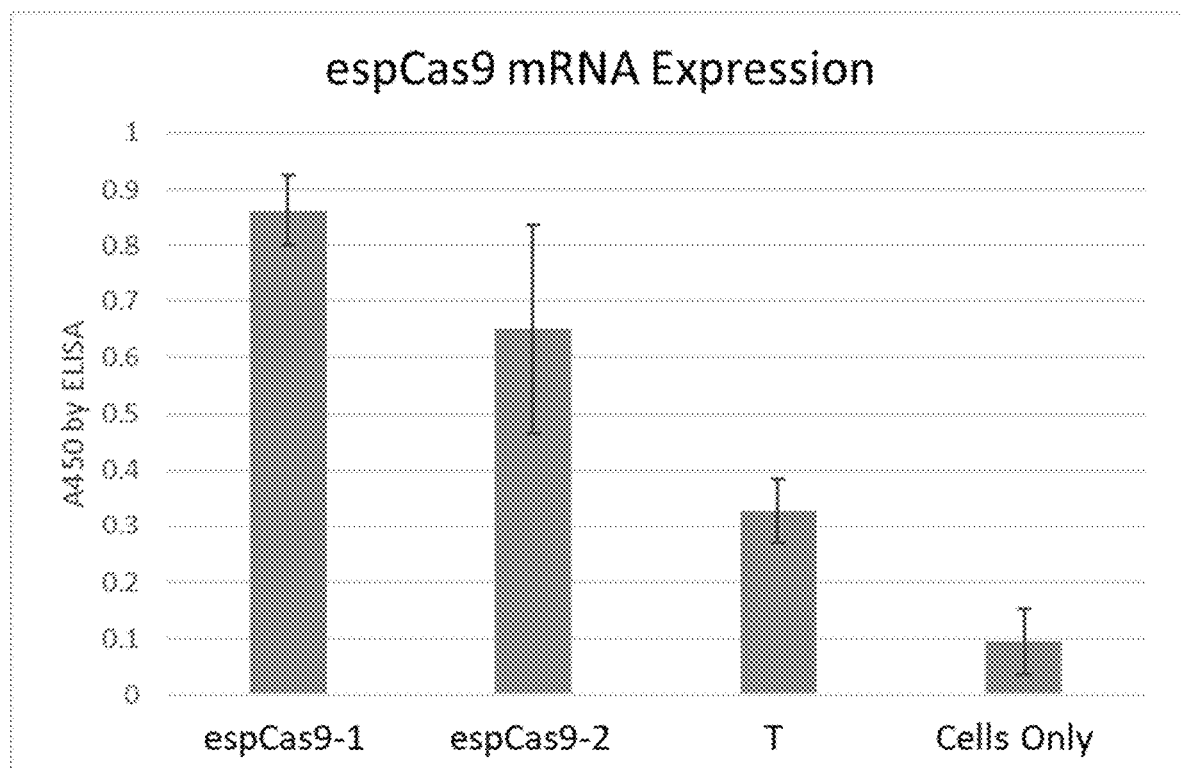
FIG. 7 shows comparison of expression levels of espCas9 mRNA prepared by various methods in accordance with one embodiment of the present disclosure.

To determine the espCas9 mRNA expression using the methods of the present disclosure, plasmid vector containing T7 promoter (SEQ ID NO: 12), 5'-UTR (SEQ ID NO: 9), espCas9 (espCas9-1) and espcas9-EGFP (espCas9-2) coding sequence, 3'-UTR (SEQ ID NO: 2), and poly A tail (100A) was used in in vitro transcription followed by transfection into A549 cells. FIG. 7 shows that the expression levels of espCas9-1 and espCas9-2 mRNA are higher than that prepared by the methods of Company T (T) and the cells only control.

Figure 8C:
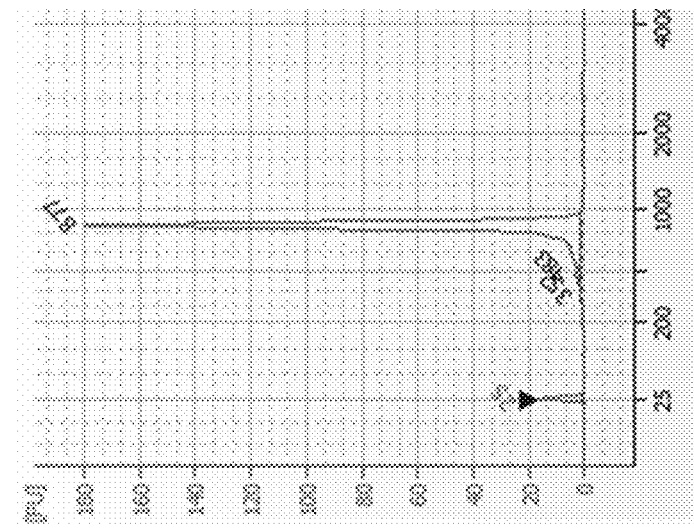
FIG. 8A-8C show purity of mRNA prepared by various methods in accordance with one embodiment of the present disclosure.
Figure 8B:
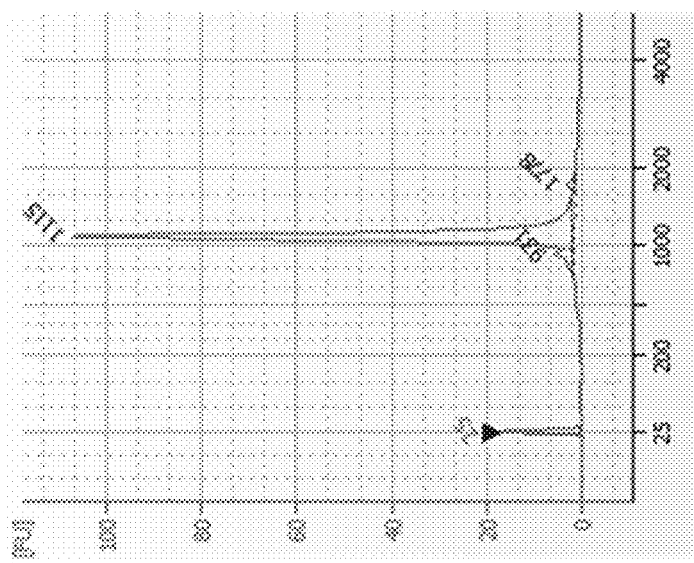
Figure 8A:
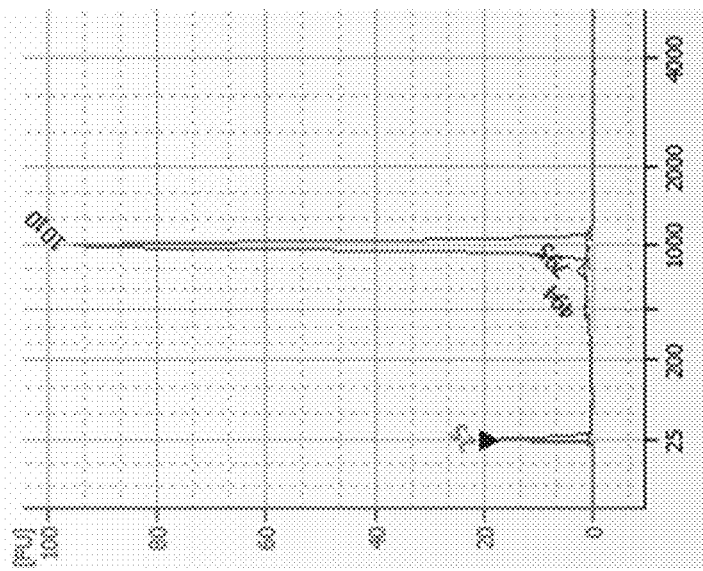
Figure 9C:
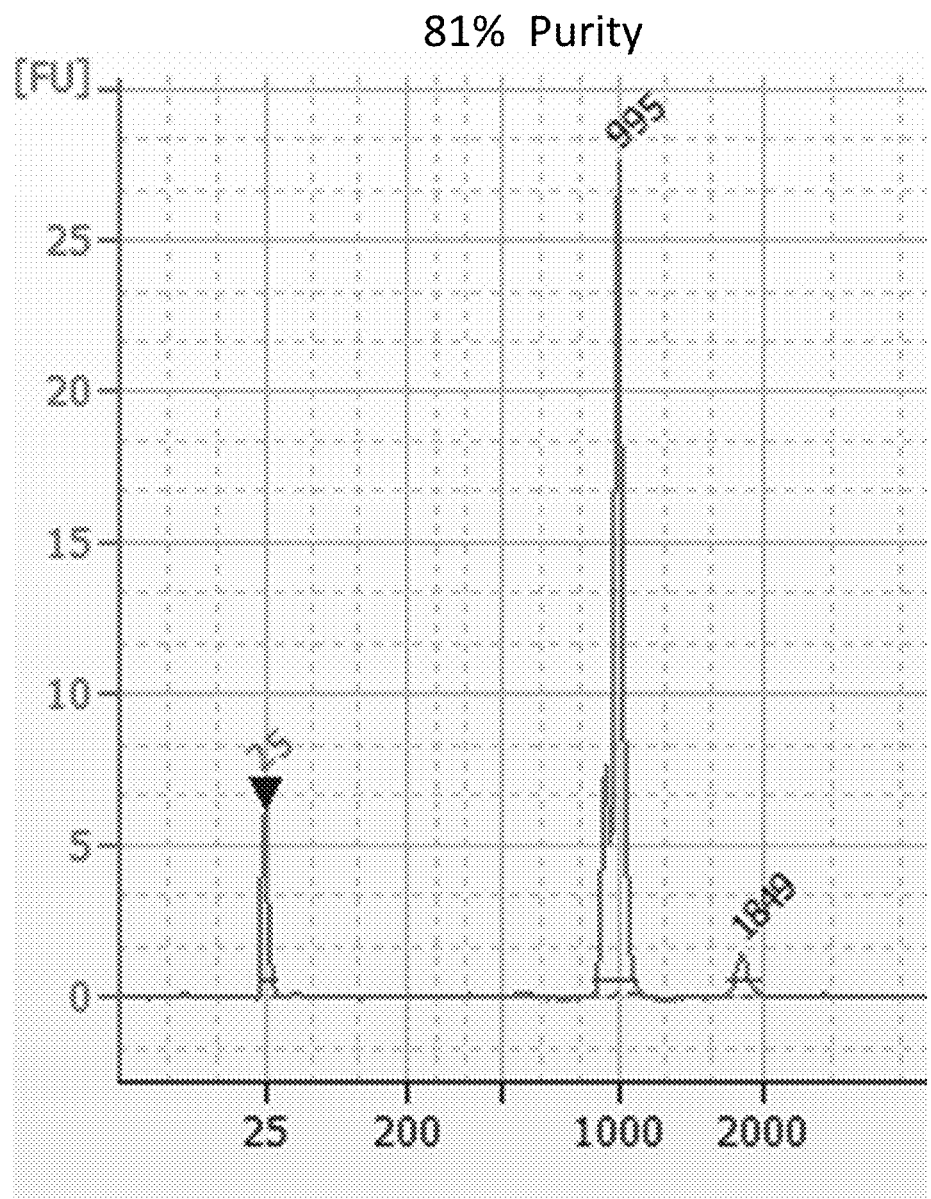
FIG. 9C shows 37° C. IVT reaction derived eGFP mRNA purity measured by bioanalyzer.

The integrity of mRNA prepared by the methods of the present disclosure were subjected to integrity analysis by Bioanalyzer to assess purity based on size. Agilent RNA Nano 6000 kit was used. The X axis indicates the mRNA length, and Y axis indicates fluorescence intensity of the tested mRNA in capillary electrophoresis. The purity of analyzed mRNA was analyzed through smear analysis to calculate the ratio of target length±10% mRNA populations. The results show that the purity of mRNA prepared by the methods of the present disclosure is about 85% (FIG. 8A, In House), which is higher than 68% prepared by the methods of Company T (FIG. 8B) and 79% prepared by the methods of Company T (FIG. 8C). The temperature for IVT reaction is one key factor affecting mRNA purity. For 1 kb mRNA eGFP, reaction at 31° C. yielded mRNA with higher purity of 90% (FIG. 9B) comparing to reaction at 37° C. yielded mRNA of 80% purity (FIG. 9C). For 10 kb mRNA, reaction at 25° C. yielded mRNA with higher purity (FIG. 11A) comparing to reaction at 31° C. (FIG. 11B).

Effects of Temperature on mRNA Integrity

Temperature may be an important factor for keeping high integrity of mRNA generated from in vitro transcription. For example, integrity of 10 kb mRNA generated from above mentioned co-transcriptional capping method was tested with bio-analyzer for the 10 kb mRNA prepared at either 31° C. or 25° C. Integrity was analysed with smear analysis function of the software for the main peak ratio. FIG. 11C shows that, for 10 kb mRNA, 25° C. for 3 hours IVT condition generated mRNA at 10 kb length with an integrity of 57%, while performing in vitro transcription at 31° C. for 3 hours generated mRNA with an integrity of 6%, as analyzed by bioanalyzer for the main peak smear analysis. FIG. 11D shows that, although the mRNA yield at 31° C. for 3 hours was higher than that at 25° C. for 3 hours, the mRNA yield at 25° C. for 4 hours was higher than that at 31° C. for 4 hours. These results suggest that mRNA prepared at 25° C. may have better integrity than that prepared at 31° C.

Effects of Reaction Time on mRNA Integrity

In vitro transcription reaction time may be another important factor that impacts mRNA integrity. Table 9 shows, for 10 kb mRNA, when perform IVT reaction at 25° C., the transcribed mRNA integrity dropped from 57% after 3 hours transcription to 52% by the time point of 4 hours. When perform IVT reaction at 31° C., the mRNA integrity dropped from 90% after 1 hour reaction to 6% after 1 hours reaction.

TABLE 9

Effects of IVT reaction time on 10Kb mRNA integrity

| | 1 hr | 2 hr | 2.5 hr | 3 hr | 3.5 hr | 4 hr | 4.5 hr |
|---|---|---|---|---|---|---|---|
| 25° C. | 51% | 53% | 57% | 57% | 52% | 52% | 52% |
| 31° C. | 90% | 6% | 6% | 6% | 6% | 6% | 6% |

Example 6 mRNA Purification mRNA obtained from Example 5 was further purified using a silica membrane column or magnetic beads. Briefly, mRNA from in vitro transcription was mixed with a buffer and ethanol, and added to silica membrane column, following by washing with 70% ethanol and eluting with water or other storage buffer for mRNA. For the product from each purification method, residual trimer caps were detected using HPLC. The residue of protein as tested with Nano Orange protein residue assay.

Example 7

Transcriptional Terminators Reduced polyA Tail Length Variation

Same GFP gene with different polyA tract (70 nt, 100 nt, and 120 nt) were ligated into either pUC57 (without terminator) vector or pUC57-terminator vector, in which rrnB-T1 terminator and rrnB-T2 terminator are located upstream from 17 promoter and lambda t terminator is located downstream from polyA tract, cut by NheI-XhoI. And the resulting plasmids were transformed into *E. coli* using standard methods and grown at 30° C. Then ten clones were randomly picked from the LB plates and subjected to Sanger sequencing for PolyA tract length validation. The lengths of polyA tails of these clones are shown in Table 10 and summarized in FIG. 13.

TABLE 10

| pUC57-70 | pUC57-terminator-70 | pUC57-100 | pUC57-terminator-100 | pUC57-120 | pUC57-terminator-120 |
|---|---|---|---|---|---|
| 73 | 70 | 106 | 104 | 113 | 120 |
| 64 | 68 | 95 | 101 | 126 | 119 |
| 62 | 69 | 89 | 99 | 112 | 118 |
| 65 | 69 | 102 | 98 | 100 | 121 |
| 57 | 71 | 86 | 99 | 107 | 120 |
| 71 | 70 | 82 | 95 | 97 | 110 |
| 65 | 70 | 88 | 97 | 89 | 109 |
| 66 | 66 | 85 | 105 | 104 | 114 |
| 54 | 69 | 89 | 100 | 73 | 118 |
| 63 | 68 | 105 | 101 | 93 | 116 |

Figure 13:
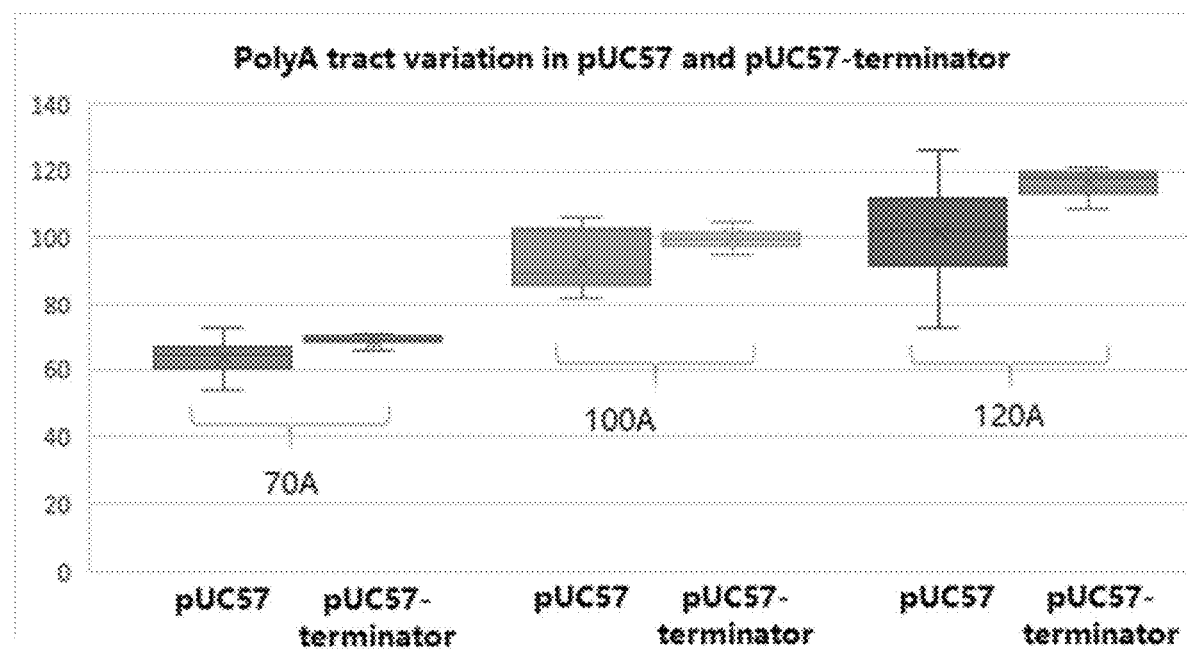
FIG. 13 shows that the variation of polyA tail lengths produced by in vitro transcription in accordance with one embodiment of the present disclosure.

FIG. 13 shows that the variation of polyA tail lengths produced by in vitro transcription using pUC57-terminator vector is smaller than that using pUC57 (without terminator) vector with different polyA tract (70 nt, 100 nt, and 120 nt).

Example 8

IVT Initiation at −1 Position Increases 5' End Homogeneity of RNA Products

To investigate the effect of IVT initiation at −1 or +1 position of DNA template on 5' end homogeneity of RNA products, IVT reactions were carried out the presence of Cap [I] using DNA template TAATACGACTCACTATAGGG (SEQ ID NO: 10), from which IVT initiation at −1 position, or TAATACGACTCACTATAAGG (SEQ ID NO: 12), from which IVT initiation at +1 position, followed by reverse transcription of RNA products into cDNA using NEBNext single cell/low input RNA library prep kit for Illumina. DNA library was prepared with NEB 7805, FS DNA library Prep kit with UMI, alignment graph was generated from Geneuous Prime software.

Figure 14:
FIG. 14 shows 5' end sequences of RNA products prepared by IVT starting from −1 position of DNA template in accordance with one embodiment of the present disclosure.
Figure 15:
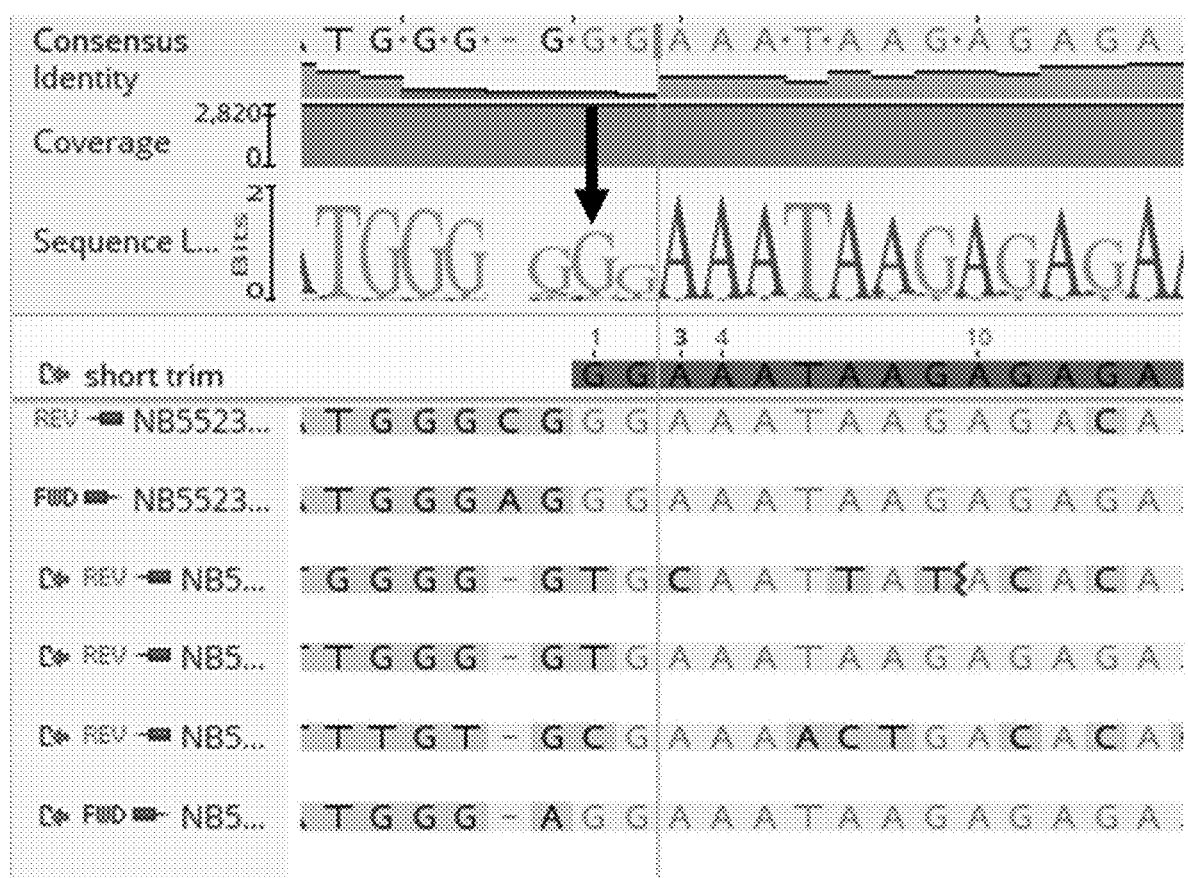
FIG. 15 shows 5' end sequences of RNA products prepared by IVT starting from +1 position of DNA template in accordance with one embodiment of the present disclosure.

Sequence alignments show that IVT starting from −1 position using TAATACGACTCACTATAGGG (SEQ ID NO: 10) (TATA-GGG) template has a lower error rate at the 5' end guanine (G) (indicated by an arrow), e.g., 0.09% (FIG. 14), than IVT starting from +1 position using TAATACGACTCACTATAAGG (SEQ ID NO: 12) (TATA-AGG) template at the 5' end guanine (G) (indicated by an arrow), e.g., 0.19% (FIG. 15). In other words, the 5' end sequence alignments from Next Generation Sequencing (NGS) show that IVT starting from −1 position has more homogenous 5' end of RNA products than IVT starting from +1 position.

Advantages of the present disclosure may include (1) in vitro transcription reaction mixtures and conditions that can increase yield, integrity, and purity of mRNAs and (2) DNA templates and cap analogues that bind to −1 and/or +1 nucleotides of promoters for in vitro transcription, thus producing more full length mRNAs, allowing for more flexibility on the choice of first mRNA base, and providing +2 position open for custom sequence.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

The invention claimed is:

1. A method for in vitro transcription of a DNA template into RNA, comprising
providing (1) a DNA template comprises a promoter operably linked to a nucleic acid comprising a 5' untranslated region (5' UTR), an open reading frame (ORF) encoding the RNA of interest, a 3' UTR, and a poly A region, and
(2) a cap analogue comprises the structure of

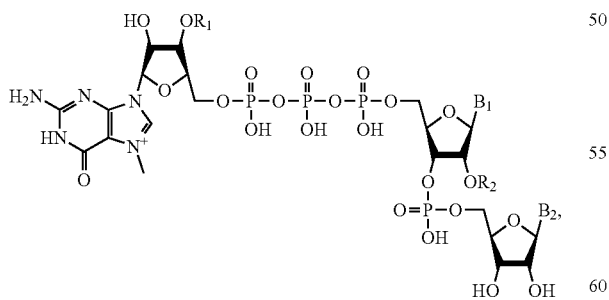

wherein $R_1$ and $R_2$ are each $CH_3$ or H; and $B_1$ and $B_2$ are each A, U, G, or C,
wherein the promoter comprises the sequence of TAATACGACTCACTATAX$_1$X$_2$X$_3$ (SEQ ID NO: 16),
wherein A at position 17 is −1 nucleotide and $X_1$ at position 18 is +1 nucleotide,
when $X_1$ is G, $X_2$ and $X_3$ are each A, T, G, or C, then $B_1$ is A and $B_2$ is G,
when $X_1$ is C, $X_2$ and $X_3$ are each A, T, G, or C, then $B_1$ is A and $B_2$ is C, and
when $X_1$ is T, $X_2$ and $X_3$ are each A, T, G, or C, then $B_1$ is A and $B_2$ is U,
wherein the cap analogue binds to −1 and +1 nucleotides of the promoter, and
incubating the DNA template and the cap analogue in a reaction mixture, wherein the incubating comprises incubating the reaction mixture at from about 15° C. to about 35° C. for from about 1 hour to about 12 hours, thereby producing the RNA, wherein
the 5' UTR consists of SEQ ID NO: 1 and the 3' UTR consists of SEQ ID NO: 4, or
the 5' UTR consists of SEQ ID NO: 1 and the 3' UTR consists of SEQ ID NO: 6, or
the 5' UTR consists of SEQ ID NO: 3 and the 3' UTR consists of SEQ ID NO: 4, or
the 5' UTR consists of SEQ ID NO: 3 and the 3' UTR consists of SEQ ID NO: 6, or
the 5' UTR consists of SEQ ID NO: 3 and the 3' UTR consists of SEQ ID NO: 8, or
the 5' UTR consists of SEQ ID NO: 5 and the 3' UTR consists of SEQ ID NO: 4, or
the 5' UTR consists of SEQ ID NO: 5 and the 3' UTR consists of SEQ ID NO: 6, or the 5' UTR consists of SEQ ID NO: 7 and the 3' UTR consists of SEQ ID NO: 4, or the 5' UTR consists of SEQ ID NO: 7 and the 3' UTR consists of SEQ ID NO: 6, or the 5' UTR consists of SEQ ID NO: 7 and the 3' UTR consists of SEQ ID NO: 8, or the 5' UTR consists of SEQ ID NO: 9 and the 3' UTR consists of SEQ ID NO: 4, or the 5' UTR consists of SEQ ID NO: 9 and the 3' UTR consists of SEQ ID NO: 6.

2. The method of claim 1, wherein the promoter comprises a sequence selected from SEQ ID NO: 10, 11, 13, and 14.

3. The method of claim 1, wherein the 5' UTR consists of SEQ ID NO: 1 and the 3' UTR consists of SEQ ID NO: 4.

4. The method of claim 1, wherein the cap analogue is selected from the group consisting of $m^7$GpppApC, $m^7$GpppApG, $m^7$GpppApU, $m^7G_{3'Ome}$pppApC, $m^7G_{3'Ome}$pppApG, $m^7G_{3'Ome}$pppApU, $m^7G_{3'Ome}$pppA$_{2'Ome}$pC, $m^7G_{3'Ome}$pppA$_{2'Ome}$pG, $m^7G_{3'Ome}$pppA$_{2'Ome}$pU, $m^7$GpppA$_{2'Ome}$pC, $m^7$GpppA$_{2'Ome}$pG, and $m^7$GpppA$_{2'Ome}$pU.

5. The method of claim 1, wherein the reaction mixture comprises
- a buffer substance in a concentration of from about 45 mM to about 55 mM,
- an RNase inhibitor in a concentration of from about 0.01 U/µl to about 0.03 U/µl,
- NTPs in a concentration of from about 3 mM to about 5 mM,
- the cap analogue in a concentration of from about 6 mM to about 8 mM,
- one or more magnesium salts in a concentration of from about 20 mM to about 30 mM,
- a polyamine in a concentration of from about 1.5 mM to about 2.5 mM,
- the DNA template in a concentration of from about 0.01 µg/µl to about 0.05 µg/µl,
- a pyrophosphatase in a concentration of from about 0.1 mU/µl to about 0.5 mU/µl, and
- an RNA polymerase in a concentration of from about 0.01 µg/µl to about 0.05 µg/µl.

6. The method of claim 5, wherein the RNA polymerase is selected from wild type T7 RNA polymerase or a variant thereof.

7. The method of claim 1, wherein the incubating comprises incubating the reaction mixture at from about 18° C. to about 31° C.

8. The method of claim 7, wherein the incubating comprises incubating the reaction mixture at about 30° C. for about 4 hours.

9. The method of claim 1, wherein the DNA template further comprises at least one transcriptional terminator located upstream and/or downstream of the open reading frame (ORF).

10. The method of claim 1, wherein $X_1$ is G, $X_2$ and $X_3$ are each A, T, G, or C, $B_1$ is A, and $B_2$ is G.

11. The method of claim 1, wherein $X_1$ is C, $X_2$ and $X_3$ are each A, T, G, or C, $B_1$ is A, and $B_2$ is C.

12. The method of claim 1, wherein $X_1$ is T, $X_2$ and $X_3$ are each A, T, G, or C, $B_1$ is A, and $B_2$ is U.

13. The method of claim 1, wherein the cap analogue in a concentration of from about 0.5 mM to about 50 mM.

14. The method of claim 1, wherein the incubating the reaction mixture is performed at about 25° C. for from about 1 hour to about 5 hours.

15. The method of claim 2, wherein the promoter comprises the sequence of SEQ ID NO: 10.

16. The method of claim 2, wherein the promoter comprises the sequence of SEQ ID NO: 11.

17. The method of claim 2, wherein the promoter comprises the sequence of SEQ ID NO: 13.

18. The method of claim 2, wherein the promoter comprises the sequence of SEQ ID NO: 14.

19. The method of claim 1, wherein the 5' UTR consists of SEQ ID NO: 1 and the 3' UTR consists of SEQ ID NO: 6.

20. The method of claim 1, wherein the 5' UTR consists of SEQ ID NO: 3 and the 3' UTR consists of SEQ ID NO: 4.

21. The method of claim 1, wherein the 5' UTR consists of SEQ ID NO: 3 and the 3' UTR consists of SEQ ID NO: 6.

22. The method of claim 1, wherein the 5' UTR consists of SEQ ID NO: 3 and the 3' UTR consists of SEQ ID NO: 8.

23. The method of claim 1, wherein the 5' UTR consists of SEQ ID NO: 5 and the 3' UTR consists of SEQ ID NO: 4.

24. The method of claim 1, wherein the 5' UTR consists of SEQ ID NO: 5 and the 3' UTR consists of SEQ ID NO: 6.

25. The method of claim 1, wherein the 5' UTR consists of SEQ ID NO: 7 and the 3' UTR consists of SEQ ID NO: 4.

26. The method of claim 1, wherein the 5' UTR consists of SEQ ID NO: 7 and the 3' UTR consists of SEQ ID NO: 6.

27. The method of claim 1, wherein the 5' UTR consists of SEQ ID NO: 7 and the 3' UTR consists of SEQ ID NO: 8.

28. The method of claim 1, wherein the 5' UTR consists of SEQ ID NO: 9 and the 3' UTR consists of SEQ ID NO: 4.

29. The method of claim 1, wherein the 5' UTR consists of SEQ ID NO: 9 and the 3' UTR consists of SEQ ID NO: 6.

\* \* \* \* \*